United States Patent [19]

Warrellow et al.

[11] Patent Number: 5,622,977
[45] Date of Patent: Apr. 22, 1997

[54] TRI-SUBSTITUTED (ARYL OR HETEROARYL) DERIVATIVES AND PHARMACEUTICAL COMPOSITIONS CONTAINING THE SAME

[75] Inventors: Graham J. Warrellow, Northwood; Ewan C. Boyd, Slough; Rikki P. Alexander, High Wycombe; John C. Head, Windor, all of United Kingdom

[73] Assignee: Celltech Therapeutics Limited, Slough, United Kingdom

[21] Appl. No.: 474,214

[22] Filed: Jun. 7, 1995

Related U.S. Application Data

[63] Continuation-in-part of Ser. No. 171,822, Dec. 22, 1993, abandoned.

[30] Foreign Application Priority Data

Dec. 23, 1992 [GB] United Kingdom ............... 9226831
Aug. 2, 1993 [GB] United Kingdom ............... 9315966

[51] Int. Cl.[6] .................. A61K 31/44; C07D 405/10; C07D 409/10; C07D 213/04
[52] U.S. Cl. .................. 514/336; 514/252; 514/255; 514/256; 514/277; 514/332; 514/340; 514/367; 514/383; 514/374; 514/394; 514/427; 514/438; 514/544; 544/242; 544/335; 546/266; 546/339; 546/269.1; 546/270.1; 546/271.7; 546/272.4; 546/271.1; 546/269.7; 546/271.4; 546/273.4; 546/272.7; 546/278.1; 546/288.4; 546/281.1; 546/283.4; 546/284.1; 548/268.6; 548/267.8; 548/179; 548/239; 548/310.1; 548/341.1; 548/562; 549/78; 560/104
[58] Field of Search .................. 544/242, 335, 544/410, 238; 546/266, 275, 283, 284, 339; 548/268.6, 267.8, 179, 239, 310, 341.1, 562; 549/78; 560/104; 514/252, 255, 256, 277, 332, 336, 360, 367, 383, 374, 394, 427, 438, 564

[56] References Cited

U.S. PATENT DOCUMENTS

| | | | |
|---|---|---|---|
| 4,012,495 | 3/1977 | Schmiechen et al. | 514/424 |
| 4,015,017 | 3/1977 | Gazave | 514/687 |
| 4,153,713 | 5/1979 | Huth et al. | 514/423 |
| 4,193,926 | 3/1989 | Schmiechen et al. | 548/517 |
| 4,303,649 | 12/1981 | Jones | 514/18 |
| 4,792,561 | 12/1988 | Walker et al. | 514/312 |
| 4,921,862 | 5/1990 | Walker et al. | 514/312 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |

FOREIGN PATENT DOCUMENTS 0393500  10/1990  European Pat. Off. .
0490823  6/1991  European Pat. Off. .
0470805  2/1992  European Pat. Off. .
0511865  11/1992  European Pat. Off. .
0537742  4/1993  European Pat. Off. .
2501443  of 0000  Germany .
1588639  4/1981  United Kingdom .
WO87/06576  11/1987  WIPO .
WO91/15451  10/1991  WIPO .
WO91/16892  11/1991  WIPO .
WO92/00968  1/1992  WIPO .
WO92/06963  4/1992  WIPO .
WO92/06085  4/1992  WIPO .
WO92/07567  5/1992  WIPO .
WO92/19594  11/1992  WIPO .
WO92/19602  11/1992  WIPO .
WO93/19748  10/1993  WIPO .
WO94/02465  2/1994  WIPO .
WO94/12461  6/1994  WIPO .

OTHER PUBLICATIONS

Ashton, "Selective Type IV Phosphodiesterase Inhibitors as Antiasthmatic Agents. The Syntheses and Biological Activities of 3–(Cyclopentyloxy)–4–methyoxybenzamides and Analogues" J. Med. Chem. 37: 1696–1703 (1994).

Buu–Hoi, N.P. et al., "Bromination of Some 1,2,2–Triarylethylenes" 1261–1263 (1958).

Buu–Hoi et al., "New Method for the Synthesis of ω,ω–Diarylacetophenones Aminated in the Aromatic Nucleus. Plynitration of Triarylethylenes" Chemical Abstracts 61: 16006h (1964).

Chemical Abstracts. Registry Handbook – Number Section. Printed Issues Columbus US *compounds with registry numbers 95992–21–5; 95971–60–1; 90053–37–5; 82668–18–6; 80395–25–1; 49610–49–3.

(List continued on next page.)

Primary Examiner—Ceila Chang
Attorney, Agent, or Firm—Woodcock Washburn Kurtz MacKieiwcz & Norris

[57] ABSTRACT

Compounds of the general formula (1)

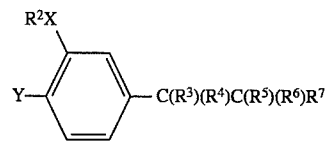

are described wherein Y is halogen or —$OR^1$, where $R^1$ is a substituted or unsubstituted alkyl; X is —O—, —S— or —$N(R^8)$—, where $R^8$ is hydrogen or alkyl; $R^2$ is substituted or unsubstituted alkyl, alkenyl, cycloalkyl or cycloalkenyl; $R^3$ is hydrogen, halogen or —$OR^9$, where $R^9$ is hydrogen or substituted or unsubstituted alkyl, alkenyl, alkoxyalkyl, or alkanoyl, or formyl, carboxamido or thiocarboxamido; $R^4$ and $R^5$, which may be the same or different, are each —$(CH_2)_n$Ar, where Ar is a monocyclic or bicyclic aryl group or monocyclic or bicyclic heteroaryl and n is integer of 0 to 3; $R^6$ is hydrogen or substituted or unsubstituted alkyl; $R^7$ is hydrogen or substituted or unsubstituted alkyl; and the salts, solvates, hydrates and N-oxides thereof. Compounds according to the invention are potent, selective and orally active PDE IV inhibitors and are useful in the prophylaxis and treatment of asthma and other diseases.

29 Claims, No Drawings

OTHER PUBLICATIONS

El-Wakil et al., "Study of the proton magnetic resonance of methoxytamoxifen towards ortho–substitiution" Chemical Abstracts 116: 255248t (1992).

Hirose et al., "Styrene Derivatives and Electrophotpgraphic Photoreceptor Containing Them" Chemical Abstracts 118: 136183z (1993).

Manhas et al., "Heterocyclic Compounds XII. Quinazoline Derivatives as Potential Antifertility Agents(1)" J. Het Chem: 711–715 (1979).

Mezheritskaya, "Synthesis and properties of carboxonium het=erocyclic systems. VII. Synthesis and properties of 2–benzyl-substituted 1,3–dioxolanium salts" Chem. Abs. 93: 95160j p. 635(1980).

O'Conner et al., "Voltammetry and Controlled Potential Oxidation of 3,4–dimethoxypropenylbenzene at a rotating platinum electrode in unbuffered acetonitrile and in acetonitrile–pyridine solution" Chemical Abstracts 60(8) #10203.4 (Apr. 13, 1964).

Ramalingam, Deshmukh and Sattur, "Synthesis and Pharmacology of 2,5–Disubstituted 1,3,4–Zxadiazoles" Indian Chem. Soc. vol.58(3) 269–271 (1981).

Reddy et al., "Inhibition of Breast Cancer Cell Growth in Vitro by a Tyrosine Kinase Inhibitor" Cancer Research 52: 3636–3641 (1992).

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" J. Med. Chem. 29: 1355–1362 (1986).

Seitz et al., "Fluorotamoxifen. A Caveat on the Generality of Electrophilic Destannylation" Chemical Abstracts 111: 57133k (1988).

Yoneda et al., "The Antiproliferative Effects of Tyrosine Kinase Inhibitors Tyrphostins on a Human Squamous Cell Carcinoma in Vitro and in Nude Mice" Cancer Research 51: 4430–4435 (1991).

TRI-SUBSTITUTED (ARYL OR HETEROARYL) DERIVATIVES AND PHARMACEUTICAL COMPOSITIONS CONTAINING THE SAME

CROSS-REFERENCE TO RELATED APPLICATION

This is a continuation-in-part of U.S. application Ser. No. 08/171,822, filed Dec. 22, 1993, now abandoned the disclosures of which are incorporated herein by reference, in their entirety.

FIELD OF THE INVENTION

This invention relates to a novel series of tri-substituted phenyl derivatives, to processes for their preparation, to pharmaceutical compositions containing them, and to their use in medicine.

BACKGROUND OF THE INVENTION

Many hormones and neurotransmitters modulate tissue function by elevating intracellular levels of adenosine 3', 5'-cyclic monophosphate (cAMP). The cellular levels of cAMP are regulated by mechanisms which control synthesis and breakdown. The synthesis of cAMP is controlled by adenylyl cyclase which may be directly activated by agents such as forskolin or indirectly activated by the binding of specific agonists to cell surface receptors which are coupled to adenylyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I–VI1) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155 and Nicholson et al (1991) TIPS, 12: 19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both anti-inflammatory and bronchodilator effects.

The design of PDE IV inhibitors has met with limited success to date, in that many of the potential PDE IV inhibitors which have been synthesized have lacked potency and/or have been capable of inhibiting more than one type of PDE isoenzyme in a nonselective manner. Lack of selective action has been a particular problem given the widespread role of cAMP in vivo and what is needed are potent selective PDE IV inhibitors with an inhibitory action against PDE IV and little or no action against other PDE isoenzymes.

We have now found a novel series of tri-substituted phenyl derivatives, members of which compared to known structurally similar compounds are potent inhibitors of PDE IV at concentrations at which they have little or no inhibitory action on other PDE isoenzymes. These compounds inhibit the isolated PDE IV enzyme and also elevate cAMP in isolated leukocytes. Certain compounds prevent inflammation in the lungs induced by carrageenan, platelet-activating factor (PAF), interleukin-5 (IL-5) or antigen challenge. These compounds also suppress the hyperresponsiveness of airway smooth muscle seen in inflamed lungs. Advantageously, compounds according to the invention have good oral activity and at orally effective doses exhibit little or none of the side-effects associated with known PDE IV inhibitors, such as rolipram. The compounds of the invention are therefore useful in medicine, especially in the prophylaxis and treatment of asthma.

Thus, according to one aspect of the invention, there is provided a compound of formula (1)

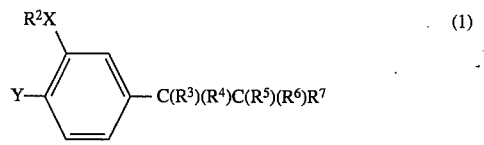

wherein

Y is halogen or —OR$^1$, where R$^1$ is substituted or unsubstituted alkyl;

X is —O—, —S— or —N(R$^8$)—, where R$^8$ is hydrogen or alkyl;

R$^2$ is substituted or unsubstituted alkyl, alkenyl, cycloalkyl or cycloalkenyl;

R$^3$ is hydrogen, halogen or —OR$^9$, where R$^9$ is hydrogen or substituted or unsubstituted alkyl, alkenyl, alkoxyalkyl or alkanoyl, or formyl, carboxamido or thiocarboxamido;

R$^4$ and R$^5$, which may be the same or different, is each independently —(CH$_2$)$_n$Ar, where Ar is substituted or unsubstituted, monocyclic or bicyclic aryl or substituted or unsubstituted, monocyclic or bicyclic heteroaryl, wherein said heteroatom is oxygen, sulphur or nitrogen and n is an integer of 0 to 3;

R$^6$ is hydrogen or substituted or unsubstituted alkyl; and

R$^7$ is hydrogen or substituted or unsubstituted alkyl; and the salts, solvates, hydrates and N-oxides thereof.

It will be appreciated that the compounds of formula (1) may have one or more chiral centers, depending on the nature of the groups R$^3$, R$^4$, R$^5$, R$^6$ and R$^7$. Where one or more chiral centers is present, enantiomers or diastereomers may exist, and the invention is to be understood to extend to all such enantiomers, diastereomers and mixtures thereof, including racemates.

In the compounds of formula (1), when Y is halogen, it may be, for example, fluorine, chlorine, bromine or iodine.

When Y in the compounds of formula (1) is —OR$^1$, R$^1$ may be, for example, substituted or unsubstituted, straight or branched alkyl, including, for example, C$_{1-6}$alkyl, such as methyl, ethyl, n-propyl or i-propyl. Optional substituents which may be present on the R$^1$ groups include one or more halogen atoms, for example, fluorine, or chlorine atoms. Exemplary substituted alkyl groups include, for example, —CH$_2$F, —CH$_2$Cl, —CHF$_2$, —CHCl$_2$, —CF$_3$ and —CCl$_3$ groups.

Alkyl groups represented by R$^2$, R$^6$ or R$^7$ in the compounds of formula (1) include substituted or unsubstituted, straight or branched C$_{1-6}$alkyl, including, for example, C$_{1-3}$alkyl, such as methyl or ethyl. Optional substituents on these alkyl groups include one, two or three substituents selected from halogen, for example, fluorine, chlorine, bromine or iodine, hydroxyl or C$_{1-6}$alkoxy, for example, C$_{1-3}$alkoxy, such as methoxy or ethoxy.

Alkenyl groups represented by R$^2$ in the compounds of formula (1) include substituted or unsubstituted, straight or branched $C_{2-6}$alkenyl, such as ethenyl, propen-1-yl and 2-methylpropen-1-yl. Optional substituents include those described above in connection with $R^2$, $R^6$ and $R^7$.

When $R^2$ in the compounds of formula (1) is substituted or unsubstituted cycloalkyl or cycloalkenyl, it may be, for example $C_{3-8}$cycloalkyl, such as cyclobutyl, cyclopentyl or cyclohexyl, or $C_{3-8}$cycloalkenyl containing, for example, one or two double bonds, such as 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl, each cycloalkyl or cycloalkenyl group being optionally substituted by one, two or three substituents selected from halogen, for example, fluorine, chlorine, bromine or iodine, straight or branched $C_{1-6}$alkyl, for example, $C_{1-3}$alkyl, such as methyl or ethyl, hydroxyl or $C_{1-6}$alkoxy, for example, $C_{1-3}$alkoxy, such as methoxy or ethoxy.

Alkyl groups represented by $R^8$ in the compounds of formula (1) include straight or branched $C_{1-6}$alkyl, for example, $C_{1-3}$alkyl, such as methyl or ethyl. When $R^3$ in the compounds of formula (1) is halogen, it may be, for example, fluorine, chlorine, bromine or iodine.

When $R^3$ in the compounds of formula (1) is —$OR^9$, it may be, for example, hydroxyl or —$OR^9$, where $R^9$ is substituted or unsubstituted, straight or branched $C_{1-6}$alkyl, for example, $C_{1-3}$alkyl, such as methyl or ethyl, $C_{2-6}$alkenyl, such as ethenyl or 2-propen-1-yl, $C_{1-3}$alkoxy$C_{1-3}$alkyl, such as methoxymethyl, ethoxymethyl or ethoxyethyl, $C_{1-6}$alkanoyl, for example, $C_{1-3}$alkanoyl, such as acetyl, or formyl [HC(=O)—], carboxamido (—$CONR^{11}R^{12}$) or thiocarboxamido (—$CSNR^{11}R^{12}$), where $R^{11}$ and $R^{12}$ in each instance may be the same or different and is each independently hydrogen or substituted or unsubstituted, straight or branched $C_{1-6}$alkyl, for example, $C_{1-3}$alkyl, such as methyl or ethyl. Optional substituents which may be present on $R^9$ include those described above in connection with the alkyl groups $R^2$, $R^6$ and $R^7$.

In the compounds of formula (1), $R^4$ and $R^5$ may each independently be —Ar, —$CH_2$Ar, —$(CH_2)_2$Ar or —$(CH_2)_3$Ar.

Monocyclic or bicyclic aryl groups represented by Ar in the compounds of formula (1) include, for example, substituted or unsubstituted $C_{6-12}$aryl, for example substituted or unsubstituted phenyl, 1- or 2-naphthyl, indenyl or isoindenyl.

When the monocyclic or bicyclic aryl group Ar contains one or more heteroatoms, it may be, for example, substituted or unsubstituted $C_{1-9}$heteroaryl containing, for example, one, two, three or four heteroatoms selected from oxygen, sulphur and nitrogen atoms. In general, Ar heteroaryl groups may be, for example, substituted or unsubstituted, monocyclic or bicyclic heteroaryl groups. Monocyclic heteroaryl groups include, for example, five- or six-membered heteroaryl groups containing one, two, three or four heteroatoms selected from oxygen, sulphur and nitrogen atoms.

Examples of heteroaryl groups represented by Ar include pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl.

The heteroaryl group represented by Ar may be attached to the remainder of the molecule of formula (1) through any ring carbon or heteroatom, as appropriate. Thus, for example, when Ar is pyridyl, it may be 2-pyridyl, 3-pyridyl or 4-pyridyl. When it is thienyl, it may be 2-thienyl or 3-thienyl, and, similarly, when it is furyl, it may be 2-furyl or 3-furyl.

When, in the compounds of formula (1), Ar is a nitrogen-containing heterocycle, it may be possible to form quaternary salts, for example, N-alkyl quaternary salts, and the invention is to be understood to extend to such salts. Thus, for example, when Ar is pyridyl, pyridinium salts may be formed, for example N-alkylpyridinium salts, such as N-methylpyridinium.

The aryl or heteroaryl groups represented by Ar in the compounds of formula (1) may each optionally be substituted by one, two, three or more substituents [$R^{10}$]. The substituent $R^{10}$ may be $R^{13}$ or —$Alk^1(R^{13})_m$, wherein $R^{13}$ is halogen, amino (—$NH_2$), substituted amino, nitro, cyano, hydroxyl (—OH), substituted hydroxyl, cycloalkoxy, formyl [HC(=O)—], carboxyl (—$CO_2H$), esterified carboxyl, thiol (—SH), substituted thiol, —$COAlk^1$, —$SO_3H$, —$SO_2Alk^1$, —$SO_2NH_2$, —$SO_2NHAlk^1$, —$SO_2N[Alk^1]_2$, —$CONH_2$, —$CONHAlk^1$, —$CON[Alk^1]_2$, —$NHSO_2H$, —$NHSO_2Alk^1$, —$N[SO_2Alk^1]_2$, —$NHSO_2NH_2$, —$NHSO_2NHAlk^1$, —$NHSO_2N[Alk^1]_2$, —$NHC(O)Alk^1$, or —$NHC(O)OAlk^1$; $Alk^1$ is straight or branched $C_{1-6}$alkylene, $C_{2-6}$alkenylene, or $C_{2-6}$alkynylene chain, optionally interrupted by one, two, or three —O— or —S— atoms, —$S(O)_p$— [where p is 1 or 2] or —$N(R^8)$—; and m is an integer of 0 to 3.

When m in —$Alk^1(R^{13})_m$ is 1, 2 or 3, it is to be understood that the substituent or substituents $R^{13}$ may be present on any suitable carbon atom in —$Alk^1$. Where more than one $R^{13}$ substituent is present, they may be the same or different and may be present on the same carbon atom or on different carbon atoms in $Alk^1$. Clearly, when m is zero and no substituent $R^{13}$ is present, or when $Alk^1$ forms pan of, for example, —$SO_2Alk^1$, the alkylene, alkenylene or alkynylene chain represented by $Alk^1$ becomes alkyl, alkenyl or alkynyl.

When $R^{13}$ is substituted amino, it may be —$NHAlk^1(R^{13a})_m$ [where $Alk^1$ and m are as defined above and $R^{13a}$ has the same definition as $R^{13}$ but is not substituted amino, substituted hydroxyl or substituted thiol] or —$N[Alk^1(R^{13a})_m]_2$, wherein each —$Alk^1(R^{13a})_m$ is the same or different.

When $R^{13}$ is halogen, it may be, for example, fluorine, chlorine, bromine, or iodine.

When $R^{13}$ is cycloalkoxy, it may be, for example, $C_{5-7}$cycloalkoxy, such as cyclopentyloxy or cyclohexyloxy.

When $R^{13}$ is substituted hydroxyl or substituted thiol, it may be —$OAlk^1(R^{13a})_m$ or —$SAlk^1(R^{13a})_m$, respectively, where $Alk^1$, $R^{13a}$ and m are as defined above.

Esterified carboxyl groups represented by $R^{13}$ include, for example, —$CO_2Alk^2$, wherein $Alk^2$ is substituted or unsubstituted, straight or branched $C_{1-8}$alkyl, such as methyl, ethyl, n-propyl, i-propyl, n-butyl, i-butyl, s-butyl or t-butyl; substituted or unsubstituted $C_{6-12}$aryl$C_{1-8}$alkyl, such as benzyl, phenylethyl, phenylpropyl, 1naphthylmethyl or 2-naphthylmethyl; substituted or unsubstituted $C_{6-12}$aryl, such as phenyl, 1-naphthyl or 2-naphthyl; substituted or unsubstituted $C_{6-12}$aryloxy$C_{1-8}$alkyl, such as phenyloxymethyl, phenyloxyethyl, 1-naphthyloxymethyl or 2-naphthyloxymethyl; substituted or unsubstituted $C_{1-8}$alkanoyloxy$C_{1-8}$alkyl, such as pivaloyloxymethyl, propionyloxyethyl or propionyloxypropyl; or substituted or unsubstituted $C_{6-12}$aroyloxy$C_{1-}$ salkyl, such as benzoyloxyethyl or benzoyloxypropyl. Optional substituents present on the $Alk^2$ group include the $R^{10}$ substituents described above.

When $Alk^1$ is present in, or as a substituent $R^{10}$, it may be, for example, a methylene, ethylene, n-propylene, i-propylene, n-butylene, i-butylene, s-butylene, t-butylene, ethenylene, 2-propenyl-ene, 2-butenylene, 3-butenylene, ethynylene, 2-propynylene, 2-butynylene or 3-butynylene chain, optionally interrupted by one, two, or three —O— or —S— atoms or —SO—, —SO$_2$— or —N(R$^8$)— groups.

Particularly useful atoms or groups represented by $R^{10}$ include fluorine, chlorine, bromine or iodine, $C_{1-6}$alkyl, for example, methyl or ethyl, $C_{1-6}$alkylamino, for example, methylamino or ethylamino, $C_{1-6}$hydroxyalkyl, for example, hydroxymethyl or hydroxyethyl, $C_{1-6}$alkylthiol, for example, methylthiol or ethylthiol, $C_{1-6}$alkoxy, for example, methoxy or ethoxy, $C_{5-7}$cycloalkoxy, for example, cyclopentyloxy, halo$C_{1-6}$alkyl, for example, trifluoromethyl, $C_{1-6}$alkylamino, for example, methylamino or ethylamino, amino (—NH$_2$), amino$C_{1-6}$alkyl, for example, aminomethyl or aminoethyl, $C_{1-6}$dialkylamino, for example, dimethylamino or diethylamino, nitro, cyano, hydroxyl (—OH), formyl [HC(=O)—], carboxyl (—CO$_2$H), —CO$_2$Alk$^2$ [where $Alk^2$ is as defined above], $C_{1-6}$alkanoyl, for example, acetyl, thiol (—SH), thio$C_{1-6}$alkyl, for example, thiomethyl or thioethyl, sulphonyl (—SO$_3$H), $C_{1-6}$alkylsulphonyl, for example, methylsulphonyl, aminosulphonyl (—SO$_2$NH$_2$), $C_{1-6}$alkylaminosulphonyl, for example, methylaminosulphonyl or ethylaminosulphonyl, $C_{1-6}$dialkylaminosulphonyl, for example, dimethylaminosulphonyl or diethylaminosulphonyl, carboxamido (—CONH$_2$), $C_{1-6}$alkylaminocarbonyl, for example, methylaminocarbonyl or ethyl-aminocarbonyl, $C_{1-6}$dialkylaminocarbonyl, for example, dimethylaminocarbonyl or diethylaminocarbonyl, sulphonylamino (—NHSO$_2$H), $C_{1-6}$alkylsulphonylamino, for example, methylsulphonylamino or ethylsulphonylamino, $C_{1-6}$dialkylsulphonylamino, for example, dimethylsulphonylamino or diethylsulphonylamino, aminosulphonylamino (—NHSO$_2$NH$_2$), $C_{1-6}$alkylaminosulphonylamino, for example, methylaminosulphonylamino or ethylaminosulphonylamino, $C_{1-6}$ dialkylaminosulphonylamino, for example, dimethylaminosulphonylamino or diethylaminosulphonylamino, $C_{1-6}$alkanoylamino, for example, acetylamino, $C_{1-6}$alkanoylamino$C_{1-6}$ alkyl, for example, acetylaminomethyl, or $C_{1-6}$alkoxycarbonylamino, for example, methoxycarbonylamino, ethoxycarbonylamino or t-butoxycarbonylamino.

Where desired, two $R^{10}$ substituents may be linked together to form a cyclic group, such as a cyclic ether, for example, $C_{2-6}$alkylenedioxy, such as ethylenedioxy.

It will be appreciated that where two or more $R^{10}$ substituents are present, their meanings in each instance is independent of the other, and they may be the same or different. The $R^{10}$ substituents may be present at any ring carbon atom away from that attached to the rest of the molecule of formula (1). Thus, for example, in phenyl groups represented by At, any substituent may be present at the 2-, 3-, 4-, 5- or 6position relative to the ring carbon atom attached to the remainder of the molecule.

In the compounds of formula (1), when an ester group is present, for example, —CO$_2$Alk$^2$, this may advantageously be a metabolically labile ester.

The presence of certain substituents in the compounds of formula (1) can enable salts of the present compounds to be formed. As known to those skilled in the art, it is generally preferred that, for biologically active materials to be useful as medicaments, they be available in a form which enables easy preparation of stable pharmaceutical formulations. For example, in certain cases, biologically active compounds contain at least one basic nitrogen atom and, therefore, are capable of existing in free base or salt form. However, the free base forms are often unsuitable for the ready preparation of stable pharmaceutical formulations and are often desirably converted to their corresponding salts. Thus, in the context of the present invention, suitable salts of the compounds described herein include pharmaceutically acceptable salts, for example, acid addition salts derived from inorganic or organic acids, and salts derived from inorganic and organic bases. It has been found that certain compounds of the present invention exhibit improved physical properties in salt form, and especially, acid addition salt form. Accordingly, these salts, which are discussed in detail below, comprise a preferred embodiment of the present invention.

Acid addition salts include, for example, hydrochlorides, hydrobromides, hydroiodides, alkylsulphonates, for example, methanesulphonates, ethanesulphonates or isethionates, arylsulphonates, for example, p-toluenesulphonates, besylates or napsylates, phosphates, sulphates, including hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts, such as sodium or potassium salts, alkaline earth metal salts, such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts. Preferred among the pharmaceutically acceptable acid addition salts are the sulphate salts, with hydrogen sulphate salts being particularly preferred. It has been found that hydrogen sulphate salts of the compounds of the present invention possess advantageous chemical and physical characteristics, relative, for example, to the free base and other salt forms. In particular, the hydrogen sulphate salts are characterized as being (1) highly crystalline; (2) thermally stable; (3) non-hygroscopic; and (4) soluble in aqueous solutions over a wide range of concentrations. In addition, hydrogen sulphate salts which are devoid of solvents and other impurities can be readily prepared. Due to these advantageous properties, the acid addition salts of the compounds of the present invention, and especially, the hydrogen sulfate salts, possess desirable preparation, handling, purity and stability characteristics.

In the compounds of formula (1), Y is preferably —OR$^1$, for example, where R$^1$ is substituted or unsubstituted methyl or ethyl, or, especially, substituted or unsubstituted methyl. Especially useful substituents which may be present on R$^1$ include one, two or three fluorine or chlorine atoms.

X in the compounds of formula (1) is preferably —O—.

A particularly useful class of compounds of formula (1) has the formula (2):

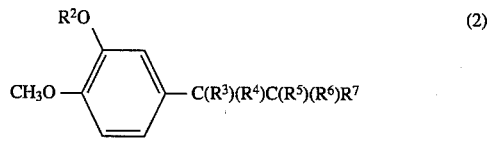

where R$^2$ is substituted or unsubstituted cycloalkyl; R$^3$, R$^4$, R$^5$, R$^6$ and R$^7$ are as defined for formula (1); and the salts, solvates, hydrates and N-oxides thereof.

In the compounds of formulae (1) or (2), R$^2$ is preferably substituted unsubstituted methyl or cyclopentyl. More preferably, R$^2$ is cyclopentyl.

$R^3$ in the compounds of formulae (1) or (2) is preferably hydrogen.

In the compounds of formulae (1) or (2), $R^6$ is preferably hydrogen or methyl, or especially hydrogen.

$R^7$ in the compounds of formulae (1) or (2) is preferably hydrogen or methyl, or especially hydrogen.

In one preference, each of $R^6$ and $R^7$ in the compounds of formula (1) is methyl. In another preference, one of $R^6$ and $R^7$ is methyl and the other is hydrogen. In general, however, $R^6$ and $R^7$ is each especially hydrogen.

$R^4$ and $R^5$ in the compounds of formulae (1) or (2) is each, independently, preferably —CH$_2$Ar or, especially, —Ar.

Particularly useful $R^4$ or $R^5$ groups in the compounds of formulae (1) or (2) include those $R^4$ or $R^5$ groups in which Ar is a monocyclic aryl group, optionally containing one or more heteroatoms selected from oxygen, sulphur, or, in particular, nitrogen atoms, and optionally substituted by one, two, three or more $R^{10}$ substituents. In these compounds, when Ar is heteroaryl, it is preferably nitrogen-containing monocyclic heteroaryl, especially six-membered nitrogen-containing heteroaryl. Thus, in one preferred example, $R_4$ and $R^5$ may each be six-membered nitrogen-containing heteroaryl. In another preferred example, $R^4$ may be monocyclic aryl or monocyclic heteroaryl containing an oxygen or sulphur atom and $R^5$ may be six-membered nitrogen-containing heteroaryl. In these examples, the six-membered nitrogen-containing heteroaryl group may be substituted or unsubstituted pyridyl, pyridazinyl, pyrimidinyl or pyrazinyl. Particular examples include substituted or unsubstituted 2-pyridyl, 3-pyridyl or, especially, 4-pyridyl, 3-pyridazinyl, 4-pyridazinyl, 5-pyridazinyl, 2-pyrimidinyl, 4-pyrimidinyl, 5-pyrimidinyl, 2-pyrazinyl or 3-pyrazinyl. The monocyclic aryl group may be phenyl or substituted phenyl, and the monocyclic heteroaryl group containing an oxygen or sulphur atom may be substituted or unsubstituted 2-furyl, 3-furyl, 2-thienyl or 3-thienyl.

One particularly useful class of compounds of formulae (1) or (2) is that wherein $R^4$ and $R^5$ is each pyridyl or, especially, monosubstituted pyridyl, or preferably disubstituted pyridyl, or $R^4$ is phenyl, thienyl or furyl, or substituted phenyl, thienyl or furyl, and $R^5$ is pyridyl or, especially monosubstituted pyridyl, or preferably disubstituted pyridyl.

In this particular class of compounds and also in general in compounds of formulae (1) or (2), when $R^4$ and/or $R^5$ is substituted phenyl, it may be, for example, a mono-, di- or trisubstituted phenyl group in which the substituent is $R^{10}$ as defined above. When $R^4$ and/or $R^5$ is monosubstituted phenyl, the substituent may be in the 2-, or preferably the 3-, or especially the 4-position relative to the ring carbon atom attached to the remainder of the molecule.

When in compounds of formulae (1) or (2), $R^4$ and/or $R^5$ is substituted pyridyl, it may be, for example, mono- or disubstituted pyridyl, such as mono- or disubstituted 2-pyridyl, 3-pyridyl or especially 4-pyridyl substituted by one or two $R^{10}$ substituents as defined above, and in particular one or two halogen atoms, such as fluorine or chlorine atoms, or methyl, methoxy, hydroxyl or nitro. Particularly useful pyridyl groups of these types are 3-monosubstituted-4-pyridyl or 3,5-disubstituted-4-pyridyl, or 2- or 4-monosubstituted-3-pyridyl or 2,4-disubstituted-3-pyridyl.

A particularly useful class of compounds according to the invention has the formula (2) wherein $R^3$, $R^6$ and $R^7$ is each hydrogen and $R^2$, $R^4$ and $R^5$ are as defined for formula (1); and the salts, solvates, hydrates and N-oxides thereof. Compounds of this type in which $R^2$ is cycloalkyl or substituted cycloalkyl, especially substituted cyclopentyl, or in particular, cyclopentyl, are particularly useful. In this class of compounds, $R^4$ is preferably monocyclic aryl, particularly phenyl or substituted phenyl, or $R^4$ is a six-membered nitrogen-containing monocyclic heteroaryl group, particularly pyridyl or substituted pyridyl and $R^5$ is a six-membered nitrogen-containing monocyclic heteroaryl group, especially pyridyl or substituted pyridyl, and in particular, substituted or unsubstituted 4-pyridyl.

Particularly useful compounds according to the invention are:

(±)-4-[2-(3-Cyclopentyloxy-4-methoxyphenyl)-2-(2-furyl)ethyl]pyridine;

(±)-4-[2-(3-Cyclopentyloxy-4-methoxyphenyl)-2-(2-thienyl)ethyl]pyridine;

(±)-4-[2-(3-Cyclopentyloxy-4-methoxyphenyl)-2-phenylethyl]-3-methylimidazole;

(±)-4-[2-(3-Cyclopentyloxy-4-methoxyphenyl)-2-phenylethyl]pyridine;

(±)-4-[1-(3-Cyclopentyloxy-4-methoxyphenyl)-2-(4-pyridyl)ethyl]pyridine;

(±)-4-[2-(3-Cyclopentyloxy-4-methoxyphenyl)-2-(4-fluorophenylethyl]pyridine;

(±)-4-[2-(3-Cyclopentyloxy-4-methoxyphenyl)-2-(4-trifluoromethylphenyl)ethyl]pyridine;

(±)-4-[2-(3-Cyclopentyloxy-4-methoxyphenyl)-2-(2-methoxyphenylethyl)]pyridine;

(±)-4-[2-(3-Cyclopentyloxy-4-methoxyphenyl)-2-(4-methoxyphenyl) ethyl]pyridine;

(±)-4-[2-(3-Cyclopentyloxy-4-methoxyphenyl)-2-(4-methylphenyl)ethyl]pyridine;

(±)-4-[2-(3-Cyclopentyloxy-4-methoxyphenyl)-2-(3-methylphenyl)ethyl]pyridine;

(±)-4-[2-(3-Cyclopentyloxy-4-methoxyphenyl)-2-(3-cyclopentyloxy-4-methoxyphenyl)-ethyl]pyridine;

(±)-4-[2-(3-Cyclopentyloxy-4-methoxyphenyl)-2-phenylethyl]-3, 5-dichloropyridine;

(±)-2-[2-(3-Cyclopentyloxy-4-methoxyphenyl)-2-phenylethyl]pyridine;

(±)-4-[1-(3-Cyclopentyloxy-4-methoxyphenyl)-2-(4-pyridyl)ethyl]aniline;

(±)-4-[1-(3-Cyclopentyloxy-4-methoxyphenyl)-2-(4-pyridyl)ethyl]benzoic acid;

(±)-Ethyl-N-{4-[1-(3-Cyclopentyloxy-4-methoxyphenyl)-2-(4pyridyl)ethyl]phenyl}-carbamate;

(±)-N-{4-[1-(3-Cyclopentyloxy-4-methoxyphenyl)-2-(4-pyridyl)ethyl]phenyl}-N'-ethylurea;

(±)-N-{4-[1-(3-Cyclopentyloxy-4-methoxyphenyl) ]-2-(4-pyridyl)ethyl}phenylacetamide;

(±)-3-[2-(3-Cyclopentyloxy-4-methoxyphenyl)-2-phenylethyl]pyridine;

(±)-4-[2-(3-Cyclopentyloxy-4-methoxyphenyl)-2-phenylethyl]pyrimidine;

(±)-4-[2-(3-Cyclopentyloxy-4-methoxyphenyl)-2-(4-hydroxymethylphenyl)ethyl]pyridine;

(±)-4-[1-(3-Cyclopentyloxy-4-methoxyphenyl)-2-(4-pyridyl)ethyl]benzamide;

(±)-Ethyl-4-[1-(3-Cyclopentyloxy-4-methoxyphenyl)-2-(4-phenylethyl]benzoate;

(±)-N-{4-[1-(3-Cyclopentyloxy-4-methoxyphenyl)-2-(4-pyridyl)ethyl)phenyl}methane-sulphonamide; or
the resolved enantiomers thereof; and the salts, solvates, hydrates and N-oxides thereof.

The above specifically mentioned compounds exist in two enantiomeric forms. Each enantiomer is useful, as are mixtures of both enantiomers.

Compounds according to the invention, including the compounds defined generically by formula (1), as well as the compounds specifically listed above, are selective and potent inhibitors of PDE IV. The ability of the compounds to act in this way may be simply determined by the tests described in the Examples hereinafter.

In certain preferred embodiments of the present invention, the compound of formula (1) comprises the racemic mixture (±)-4-[2-(3-cyclopentyloxy-4-methoxyphenyl)-2phenylethyl]-pyridine. An isomer contained in this mixture, (+)-4-[2-(3-cyclopentyloxy-4-methoxyphenyl)-2-phenylethyl]pyridine, is particularly preferred. The (+)-isomer of 4-[2-(3-cyclopentyloxy-4-methoxyphenyl)-2-phenylethyl]pyridine corresponds to the (R)-isomer and is, therefore, alternatively referred to herein as (R)-4-[2-(3-cyclopentyloxy-4-methoxyphenyl)-2-phenylethyl]pyridine.

As noted above, certain preferred embodiments of the present invention involve the salt forms, including the acid addition salt forms, such as the sulphate salts, with the hydrogen sulphate salt being particularly preferred. Especially preferred among the sulphate salts is (R)-4-[2-(3-cyclopentyloxy-4-methoxyphenyl)-2-phenylethyl]pyridine sulphate salt, with (R)-4-[2-(3-cyclopentyloxy-4-methoxyphenyl)-2-phenylethyl]pyridine hydrogen sulphate salt being particularly preferred.

The compounds according to the invention are thus of particular use in the prophylaxis and treatment of human diseases where an unwanted inflammatory response or muscular spasm including, for example, bladder or alimentary smooth muscle spasm, is present and where the elevation of cAMP levels may be expected to prevent or alleviate the inflammation and relax muscle.

Particular uses to which the compounds of the invention may be put include the prophylaxis and treatment of asthma, especially inflamed lung associated with asthma, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, allergic rhinitis, adult respiratory distress syndrome, diabetes insipidus, allergic conjunctivitis, vernal conjunctivitis, arterial restenosis and artherosclerosis.

The compounds of the present invention can also suppress neurogenic inflammation through elevation of cAMP in sensory neurones. Thus, the present compounds can act as analgesic, antitussive and anti-hyperalgesic agents for the treatment of irritation and pain associated with inflammatory diseases.

Compounds according to the invention may also elevate cAMP in lymphocytes and thereby suppress unwanted lymphocyte activation in immune-based diseases, such as rheumatoid arthritis, rheumatoid spondylitis, transplant rejection and graft versus host disease. The present compounds have also been found to reduce gastric acid secretion and therefore can be used to treat conditions associated with hypersecretion.

Compounds according to the invention suppresses cytokine synthesis by inflammatory cells in response to immune or infectious stimulation. The compounds are, therefore, useful in the treatment of bacterial, fungal or viral induced sepsis and septic shock in which cytokines, such as tumor necrosis factor (TNF), are key mediators. Also, the present compounds suppress inflammation and pyrexia due to cytokines and are thus useful in the treatment of inflammation and cytokine-mediated chronic tissue degeneration which occurs in diseases such as rheumatoid or osteoarthritis.

Over-production of cytokines, such as TNF, in bacterial, fungal or viral infections or in diseases such as cancer, leads to cachexia and muscle wasting. The compounds of the present invention are capable of ameliorating these symptoms with a consequent enhancement of quality of life.

Compounds of the invention also elevate cAMP in certain areas of the brain and thereby counteract depression and memory impairment.

The present compounds can also suppress cell proliferation in certain tumor cells and can be used, therefore, to prevent tumor growth and invasion of normal tissues.

For the prophylaxis or treatment of disease, the compounds according to the invention may be administered as pharmaceutical compositions, and according to a further aspect of the invention, there is provided a pharmaceutical composition which comprises a compound of formula (1), or a pharmaceutically-acceptable salt thereof, together with one or more pharmaceutically-acceptable carriers, excipients or diluents.

Pharmaceutical compositions according to the invention may take a form suitable for oral, buccal, parenteral, nasal, topical or rectal administration, or a form suitable for administration by inhalation or insufflation.

Advantageously, the pharmaceutical compositions may be prepared using conventional procedures. Thus, the invention further provides a process for the preparation of a pharmaceutical composition containing (R)-4-[2-(3-cyclopentyloxy-4-methoxyphenyl)-2-phenylethyl]pyridine hydrogen sulphate salt together with one or more pharmaceutically acceptable carriers, excipients or diluents which comprises the step or steps of combining (R)-4-[2-(3-cyclopentyloxy-4-methoxyphenyl)-2-phenylethyl]pyridine hydrogen sulphate salt with one or more pharmaceutically acceptable carriers, excipients or diluents.

For oral administration, the pharmaceutical compositions may take the form of, for example, tablets, lozenges or capsules prepared by conventional means with pharmaceutically acceptable excipients, such as binding agents, for example, pregelatinized maize starch, polyvinylpyrrolidone or hydroxypropyl methylcellulose; fillers, for example, lactose, microcrystalline cellulose or calcium hydrogen phosphate; lubricants, for example, magnesium stearate, talc or silica; disintegrants, for example, potato starch or sodium glycollate; or wetting agents, for example, sodium lauryl sulphate. The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives, such as suspending agents, emulsifying agents, non-aqueous vehicles and preservatives. The preparations may also contain buffer salts, flavoring, coloring and sweetening agents, as appropriate.

Preparations for oral administration may be suitably formulated to give controlled release of the active compound.

For buccal administration the compositions may take the form of tablets or lozenges, formulated in a conventional manner.

The compounds of formula (1) may be formulated for parenteral administration by injection, for example, bolus injection or infusion. Formulations for injection may be presented in unit dosage form, for example, in glass ampule or multi-dose containers, such as glass vials. The compositions for injection may take such forms as suspensions, solutions or emulsions in oily or aqueous vehicles, and may contain formulatory agents, such as suspending, stabilizing, preserving and/or dispersing agents. Alternatively, the active ingredient may be in powder form for constitution with a suitable vehicle, for example, sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurized packs or a nebulizer, with the use of a suitable propellant, for example, dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular inflammatory condition will vary depending, for example, on the compound chosen, and the condition of the patient to be treated. In general, however, daily dosages may range from about 100 ng/kg to about 100 mg/kg, for example, about 0.01 mg/kg to about 40 mg/kg body weight for oral or buccal administration, from about 10 ng/kg to about 50 mg/kg body weight for parenteral administration, and about 0.05 mg to about 1000 mg, for example, about 0.5 mg to about 1000 mg for nasal administration or administration by inhalation or insufflation.

The compounds according to the invention may be prepared by the following processes. The symbols Y, $R^2$, $R^3$, $R^4$, $R^5$, $R^6$, $R^7$ and X, when used in the formulae below, are to be understood to represent those groups described above in relation to formula (1), unless otherwise indicated. In the reactions described below, it may be necessary to protect reactive functional groups, for example, hydroxy, amino, thio, or carboxy groups, where these are desired in the final product, to avoid their unwanted participation in the involved reactions. Conventional protecting groups may be used in accordance with standard practice [see, for example, Green, T. W., "Protective Groups in Organic Synthesis John Wiley and Sons, 1981.] Deprotection can take place in the last step in the synthesis of compounds of formula (1). Thus, for example, compounds of formula (1), wherein $R^4$ and/or $R^5$ contains a carboxylic acid group, may be prepared by deprotecting the corresponding compound wherein $R^4$ and/or $R^5$ contains a protected carboxyl group, such as an oxazolinyl group, for example, 4,4-dimethyl-2-oxazolinyl, in the presence of a base, for example, sodium hydroxide, in an acid solvent, for example, aqueous hydrochloric acid, at an elevated temperature, for example, the reflux temperature.

Thus, according to a further aspect of the invention, a compound of formula (1) wherein $R^3$ and $R^7$ is each a hydrogen atom may be prepared by hydrogenation of a compound of formula (3):

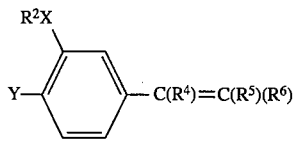

The hydrogenation may be performed using, for example, hydrogen in the presence of a catalyst. Suitable catalysts include metals, such as platinum or palladium, optionally supported on an inert carrier, such as carbon or calcium carbonate; nickel, for example, Raney nickel, or rhodium. The reaction may be performed in a suitable solvent, for example, an alcohol, such as methanol or ethanol, an ether, such as tetrahydrofuran or dioxane, or an ester, such as ethyl acetate, optionally in the presence of a base, for example, a tertiary organic base, such as triethylamine, at, for example, ambient temperature.

Alternatively, the reaction may be accomplished by transfer hydrogenation using an organic hydrogen donor and a transfer agent. Suitable hydrogen donors include, for example, acids, such as formic acid, formates, for example, ammonium formate, alcohols, such as benzyl alcohol or ethylene glycol, hydrazine, and cycloalkenes, such as cyclohexene or cyclohexadiene. The transfer agent may be, for example, a transition metal, for example, palladium or platinum, optionally supported on an inert carrier as discussed above, nickel, for example, Raney nickel, ruthenium, for example, tris(triphenylphosphine)ruthenium chloride, or copper. The reaction may generally be performed at an ambient or elevated temperature, optionally in the presence of a solvent, for example, an alcohol, such as ethanol, or an acid, such as acetic acid.

Intermediates of formula (3) may be prepared using a Horner-Wadsworth-Emmons approach by reaction of a ketone of formula (6) [described hereinafter] with phosphonate $R^5CH_2PO(OAlk)_2$, where Alk is $C_{1-4}$alkyl, such as methyl, in the presence of a base, such as sodium hydride. The phosphonates for use in this reaction may be prepared by conventional methods, for example, by reaction of a compound $R^5CH_2L$, where L is a leaving group, such as a chlorine atom, with a phosphine $P(OAlk)_3$.

In another process for the preparation of intermediates of formula (3), an alkene of formula (4):

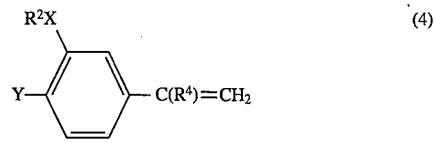

may be coupled in a Heck reaction with an organopalladium compound derived from a compound $R^5Hal$ [where Hal is a halogen atom, such as a bromine atom] and a palladium salt, such as palladium acetate, in the presence of a phosphine, such as tri-o-tolyl phosphine, and a base, such as triethylamine, at an elevated temperature and pressure.

Intermediate alkenes of formula (4) may be obtained by reaction of a corresponding ketone of formula (6) (described hereinafter) using a Wittig reaction employing a phosphonium salt, such as methyltriphenylphosphonium bromide, in the presence of a base, such as n-butyllithium, and an inert solvent, such as tetrahydrofuran, at, for example, about 0° C. to about ambient temperature.

Intermediates of formula (3) may also be prepared by dehydration of an alcohol of formula (5):

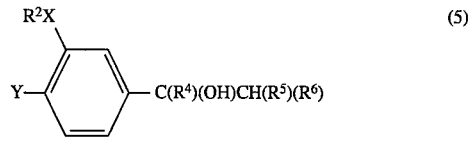

using an acid- or base-catalyzed elimination.

Suitable acids include, for example, phosphoric or sulphonic acids, for example, 4-toluenesulphonic acid. The reaction may be performed in an inert organic solvent, for example, a hydrocarbon solvent, such as toluene, at an elevated temperature, for example, about the reflux temperature. Base-catalyzed elimination may be performed using, for example, trifluoroacetic anhydride, in the presence of an organic base, such as triethylamine, at a low temperature, for example, from about 0° C. to about ambient temperature, in a solvent, such as dichloromethane or tetrahydrofuran.

In certain instances, the reaction conditions used may also cleave the group $R^2$ in the starting material of formula (4) to yield an intermediate of formula (3) where $R^2$ is hydrogen. Such compounds may be converted to the desired compound of formula (3) by reaction with a halide $R^2$Hal (where Hal is a halogen atom, such as a bromine or chlorine atom) as described hereinafter in connection with the preparation of compounds of formula (1) from the corresponding compounds where $R^2$ is hydrogen.

It will be appreciated that the alcohols of formula (5) are compounds of the invention in which $R^3$ is hydroxyl. Thus, according to a further aspect of the invention, a compound of formula (1), wherein $R^3$ is hydroxyl and $R^7$ is hydrogen, may be prepared by reaction of a ketone of formula (6):

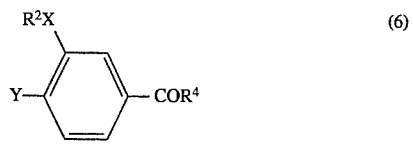

(6)

with an organometallic reagent $R^5R^6$CHZ, where Z is a metal atom.

Metal atoms represented by Z include, for example, lithium atoms.

The reaction may be performed in a solvent, such as an ether, for example, a cyclic ether, such as tetrahydrofuran, at a low temperature, for example, about −70° C. to about ambient temperature. This reaction is particularly suitable for the preparation of compounds of formula (1) wherein $R^5$ is an electron deficient group, such as a 2- or 4-pyridyl group.

Reagents $R^5R^6$CHZ are either known compounds or may be prepared, preferably in situ during the above process, by reaction of a compound AlkCH$_2$Z [where Alk is alkyl, such as n-propyl] with a compound $R^5R^6$CH$_2$, where necessary, in the presence of a base, such as an amine, for example, diisopropylamine, using the above-mentioned conditions.

Ketones of formula (6) may be prepared by oxidation of a corresponding alcohol of formula (7):

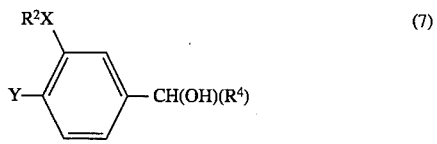

(7)

using an oxidizing agent, such as manganese dioxide, in a solvent, such as dichloromethane, at ambient temperature.

Alternatively, ketones of formula (6) may be prepared by reaction of a halide of formula (8):

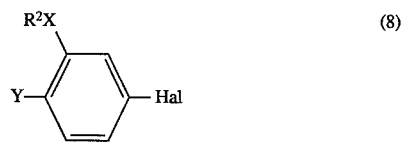

(8)

[where Hal is a halogen atom, such as a bromine or chlorine atom] by halogen-metal exchange with a base, such as n-butyllithium, followed by reaction with a nitrile $R^4$CN, an acid chloride $R^4$COCl or an ester $R^4$CO$_2$Alk (where Alk is alkyl, for example, methyl), in a solvent, such as tetrahydrofuran, at a low temperature, for example, about −70° C., and subsequent treatment with an acid, such as hydrochloric acid at, for example, about −20° C. to about ambient temperature.

Alcohols of formula (7) may be prepared by reaction of an aldehyde of formula (9):

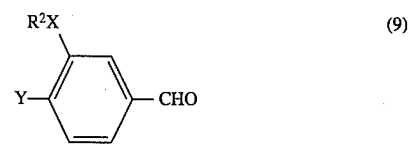

(9)

with an organometallic compound, such as an organolithium compound $R^4$Li, or a Grignard reagent $R^4$MgBr, in a solvent, such as tetrahydrofuran, at a low temperature, for example, about −55° C. to about 0° C.

Aldehydes of formula (9) may be prepared by alkylation of a corresponding compound of formula (10):

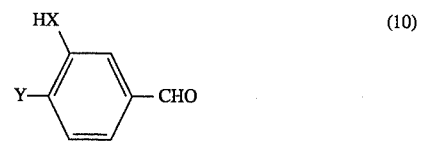

(10)

using a compound $R^2$Hal [where Hal is as previously defined] using the reagents and conditions described hereinafter for the alkylation of intermediates of formula (18).

Intermediates of formula (10) are either known compounds or may be prepared from known starting materials by methods analogous to those used for the preparation of the known compounds.

Halides of formula (8) may be prepared by alkylation of a compound of formula (11):

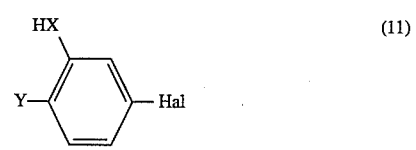

(11)

using the reagents and conditions discussed above in relation to the alkylation of aldehydes of formula (10).

Halides of formula (11), where X is —O—, may be prepared by oxidation of an aldehyde of formula (12):

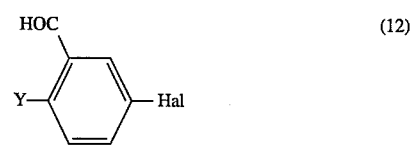

(12)

using an oxidizing agent, such as 3-chloroperoxybenzoic acid, in a halogenated hydrocarbon, such as chloroform, at a temperature of from about 0° C. to about room temperature.

Aldehydes of formula (12) and halides of formula (11), where X is —S— or —N($R^8$)—, are either known compounds or may be prepared from known starting materials by methods analogous to those used for the preparation of the known compounds.

In yet another process according to the invention, compounds of formula (1), wherein $R^3$, $R^6$ and $R^7$ is each a hydrogen atom, may be prepared by decarboxylation of an acid of formula (13):

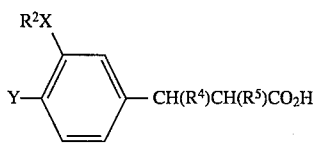

(13)

The reaction may be carried out by treatment of the compound of formula (13) with a base, for example, an inorganic base, such as a hydroxide, including sodium hydroxide, in a solvent, such as an alcohol, for example, ethanol, at an elevated temperature, for example, the reflux temperature, followed by acidification of the reaction mixture to a pH of about pH 4 to about pH 6 with an acid, such as an inorganic acid, for example, hydrochloric acid, at an elevated temperature, for example, the reflux temperature.

If desired, the acid of formula (13) may be generated in situ from the corresponding ester or nitrile using the above reaction conditions, or by initial treatment with an acid.

Intermediates of formula (13) may be prepared by reacting a compound of formula (14)

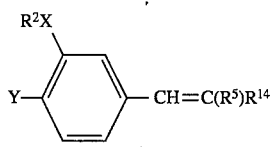

(14)

[where $R^{14}$ is an ester of an acid —$CO_2H$, for example, an alkyl ester, such as an ethyl ester, or —CN, with a Grignard reagent $R^4MgBr$, in the presence of a complexing agent, for example, a copper (I) bromide-dimethyl sulphide complex, or copper (I) chloride with an organolithium compound, for example, $R^4Li$, in a solvent, for example, tetrahydrofuran, at low temperature, for example, about –40° C., followed by treatment with a base or an acid to yield the acid of formula (13), where $R^{14}$ is —$CO_2H$. The Grignard and the lithium reagents are either known compounds or may be prepared in a manner similar to that used to synthesize the known compounds.

Compounds of formula (14) may be obtained by reacting an aldehyde of formula (9) with an ester or nitrile $R^5CH_2R^{14}$ in an acid solvent, such as acetic acid, at an elevated temperature, for example, the reflux temperature, in the presence of a base, such as ammonium acetate.

In a further process according to the invention, a compound of formula (1), wherein $R^3$, $R^6$ and $R^7$ is each hydrogen and $R^5$ is heteroaryl, may be generally prepared by cyclization of a compound of formula (15):

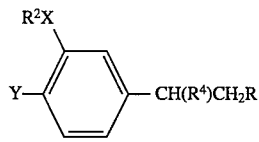

(15)

where R is carboxyl [—$CO_2H$] or a reactive derivative thereof, a nitrile [—CN] or an imine salt with a bifunctional reagent $W^1R^{5a}W^2$ and, where necessary, a compound $R^{5b}W^3$ [where $W^1$, $W^2$ and $W^3$, which may be the same or different, is each a reactive functional group or a protected derivative thereof, and $R^{5a}$ and $R^{5b}$ are components of the heteroaryl group $R^5$, such that when added together with $W^1$, $W^2$ and $W^3$ to the group R in compounds of formula (15), the resulting group —$RW^1R^{5a}W^2$ or —$RW^1R^{5a}W^2R^{5b}W^3$ constitutes the heteroaryl group $R^5$].

Reactive derivatives of carboxylic acids for use in this reaction include acid halides, for example, acid chlorides, amides, including thioamides, or esters, including thioesters. Imine salts include, for example salts of formula —C(OAlk)=$NH_2^+A^-$, where Alk is $C_{1-4}$alkyl and $A^-$ is a counterion, for example, a chloride ion.

In this general reaction, the reactive functional groups represented by $W^1$, $W^2$ or $W^3$ may be any suitable carbon, nitrogen, sulphur or oxygen nucleophiles. Particular examples include simple nucleophiles, such as carbanions, including those generated by the coupling of an alkyl group with an organometallic compound, and amino, thiol and hydroxyl.

In general, the cyclization reaction will initially be performed in a solvent, for example, an inert solvent, such as a halocarbon, for example, dichloromethane, an ether, for example, a cyclic ether, such as tetrahydrofuran, or a hydrocarbon, for example, an aromatic hydrocarbon, such as toluene, from a low temperature, for example, about –70° C. to about the reflux temperature, where necessary in the presence of a base or a thiation reagent, for example, Lawesson's reagent, followed, if necessary, by heating to an elevated temperature, for example, about the reflux temperature.

Thus, in one particular example, compounds of formula (1), wherein $R^3$, $R^6$ and $R^7$ is each hydrogen and $R^5$ is benzothiazolyl, benzoxazolyl or benzimidazolyl, may be prepared by reaction of a compound of formula (15), where R is an acid halide, for example, an acid chloride, with a reagent $W^1R^{5a}W^2$, which is 2-aminothiophenol, 2-hydroxyphenol, or 1,2diaminobenzene, respectively, in the presence of a base, for example, an organic amine, such as pyridine, in a solvent, for example, a halocarbon, such as dichloromethane, from about –70° C. to about the reflux temperature.

In another example of the general cyclization process, a compound of formula (15), where R is an acid halide: as described above, may be reacted with a compound $W^1R^{5a}W^2$, which is a monoalkylmalonate, for example, ethyl hydrogen malonate, followed by reaction with a compound $R^{5b}W^3$, which is hydrazine, to give a compound of formula (1), wherein $R^3$, $R^6$ and $R^7$ is each hydrogen and $R^5$ is 5-hydroxypyrazolyl.

In another variation of the cyclization process, the halide of formula (15) may be reacted with a compound $W^1R^{5a}W^2$, which is $BrMg(CH_2)_3[—O(CH_2)_2O—]$, followed by reaction in an acid solution with a compound $R^{5b}W^3$, which is methylamine, to yield a compound of formula (1), wherein $R^3$, $R^6$ and $R^7$ is each hydrogen and $R^5$ is N-methylpyrrole.

In a further example of the cyclization process, the halide of formula (15) may be reacted with a compound $W^1R^{5a}W^2$, which is $H_2NNHCSNH_2$, in an aromatic hydrocarbon, such as toluene, at an elevated temperature, for example, about 150° C., followed by treatment with a base, for example, an inorganic base, such as sodium bicarbonate, to give a compound of formula (1), wherein $R^3$, $R^6$ and $R^7$ is each hydrogen and $R^5$ is 1,2,4-triazolyl-5-thiolate.

Intermediate compounds of formula (15) are particularly useful and form a further aspect of the invention. Active derivatives of the acids of formula (15) and other compounds of formula (15), where R is a nitrile or an imine salt, may be prepared from the corresponding acids [where R is —$CO_2H$] using conventional procedures for converting carboxylic acids to such compounds, including, for example, as described in the Examples hereinafter.

Acids of formula (15) [where R is —CO$_2$H] may be prepared by hydrolyzing a diester of formula (16)

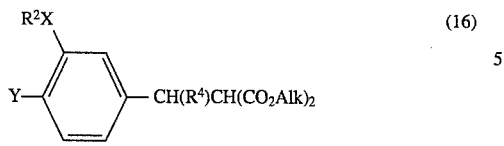
(16)

where Alk is C$_{1-4}$alkyl, for example, ethyl, with a base, for example, sodium hydroxide, in a solvent, for example, dioxane, at an elevated temperature, for example, about the reflux temperature, followed by acidification at an elevated temperature.

Diesters of formula (16) may be prepared by reacting a diester of formula (17)

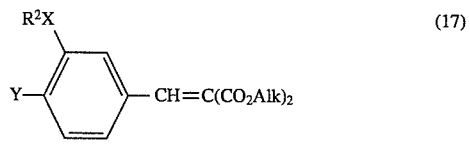
(17)

with an organometallic reagent, such as a Grignard reagent, using the conditions described above for the preparation of alcohols of formula (1).

In another process according to the invention, a compound of formula (1) may be prepared by alkylation of a compound of formula (18):

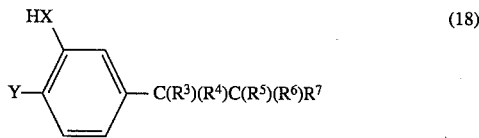
(18)

using a reagent R$^2$L, where L is a leaving group.

Leaving groups represented by L include halogen atoms, such as iodine or chlorine or bromine atoms, or sulphonyloxy groups, such as arylsulphonyloxy groups, for example, p-toluenesulphonyloxy.

The alkylation reaction may be carried out in the presence of a base, for example, an inorganic base, such as a carbonate, for example, caesium or potassium carbonate, an alkoxide, for example, potassium t-butoxide, or a hydride, for example, sodium hydride, in a dipolar aprotic solvent, such as an amide, for example, a substituted amide, such as dimethylformamide, or an ether, for example, a cyclic ether, such as tetrahydrofuran, at ambient temperature or above for example, about 40° C. to about 50° C.

Intermediates of formula (18) may be obtained from the corresponding protected compound of formula (19):

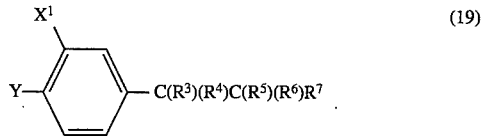
(19)

wherein X$^1$ is protected hydroxy, thio or amino using conventional procedures [see Green, T. W. ibid]. Thus, for example, where X is t-butyldimethylsilyloxy, the required hydroxyl group may be obtained by treatment of the protected intermediate with tetrabutylammonium fluoride. The protected intermediate of formula (18) may be prepared in an analogous manner to the compounds of formula (1) using the reactions described herein and appropriately protected intermediates.

Compounds of formula (17) may be prepared by condensing an aldehyde of formula (9) with a malonate, for example, diethylmalonate, if necessary in the presence of catalysts, for example, piperidine and acetic acid, in an inert solvent, for example, toluene, at elevated temperature, for example, about the reflux temperature.

Compounds of formula (1) may also be prepared by interconversion of other compounds of formula (1). Thus, for example, a group represented by R$^4$ or R$^5$ in the compounds of formula (1) may be substituted in the aryl or heteroaryl portions by any of the groups R$^{10}$ by an appropriate substitution reaction using the corresponding unsubstituted compound of formula (1) and a nucleophile or electrophile containing R$^{10}$.

In another example of an interconversion process, a compound of formula (1), wherein the aryl or heteroaryl group in R$^4$ and/or R$^5$ contains a —CH$_2$NH$_2$ substituent, may be prepared by the reduction of a corresponding compound, wherein R$^4$ and/or R$^5$ contains a nitrile group, using, for example, a complex metal hydride, such as lithium aluminum hydride, in a solvent, such as an ether, for example, diethylether.

In a further example, a compound of formula (1), wherein the aryl or heteroaryl group in R$^4$ and/or R$^5$ contains an alkanoylamino or alkanoylaminoalkyl substituent, may be prepared by acylation of a corresponding compound, wherein R$^4$ and/or R$^5$ contains —NH$_2$ or alkylamino, by reaction with an acyl halide in the presence of a base, such as a tertiary amine, for example, triethylamine, in a solvent, such as dichloromethane.

In yet another example of an interconversion process, compounds of formula (1), wherein R$^4$ and/or R$^5$ is substituted by an ester [CO$_2$Alk2], for example, an ethanoate, may be prepared by esterification of a corresponding compound wherein R$^4$ and/or R$^5$ contains a carboxylic acid, using an acid halide, such as an acid chloride, for example, acetyl chloride, in an alcohol, such as ethanol, at an elevated temperature, such as the reflux temperature.

Compounds of formula (1), wherein R$^4$ and/or R$^5$ is substituted with carboxyl (—CO$_2$H), may be prepared from the corresponding compound wherein R$^4$ and/or R$^5$ contains a formyl group which can be oxidized with an oxidizing agent, for example, potassium permanganate, in a solvent, such as an alcohol, for example, tert-butanol, at about ambient temperature.

In a further interconversion reaction, compounds of formula (1), wherein R$^4$ and/or R$^5$ is substituted by an aminoalkyl group, such as dimethylaminomethyl, may be prepared by reductive amination of a corresponding compound wherein R$^4$ and/or R$^5$ contains a formyl group, using an amine, for example, dimethylamine, in the presence of a reducing agent, for example, sodium cyanborohydride, if necessary in the presence of a catalyst, for example, ethanolic HCl, in a solvent, such as an alcohol, for example, methanol, at about ambient temperature.

In another example of an interconversion reaction, a compound of formula (1), wherein R$^4$ and/or R$^5$ is substituted by a formyl group, may be reduced to the corresponding alcohol, for example, where R$^4$ and/or R$^5$ contains a hydroxymethyl group, using a reducing agent, for example, sodium borohydride, in a solvent, such as an alcohol, for example, ethanol, at a temperature of from about 20° C. to about ambient temperature. The resulting alcohol may then be converted to the corresponding alkoxy derivative, for example, methoxymethyl, by reaction with an alkyl halide or alkyl sulphonate using the methods and reagents described above for the alkylation of intermediates of formula (18).

In a further example of an interconversion process, compounds of formula (1), wherein R$^4$ and/or R$^5$ contains a carboxamido (—CONHR$^{11}$) or an aminocarbonyl (—NH- COR$^{11}$) group, may be prepared by reaction of the corresponding compound wherein R$^4$ and/or R$^5$ contains —CO$_2$H or —NH$_2$, respectively, by reaction with a carbamate, such as isobutyl chloroformate or ethyl chloroformate, in the presence of a base, such as an amine, for example, triethylamine or N-methylmorpholine, in a solvent, such as dichloromethane, or a mixture of solvents, for example, tetrahydrofuran and dimethylformamide, at a temperature of from about −20° C. to about room temperature.

In a still further interconversion reaction, compounds of formula (1), wherein R$^4$ and/or R$^5$ is substituted by —NHCONHR$^{11}$, may be prepared by reacting a corresponding compound wherein R$^4$ and/or R$^5$ is substituted by amino (—NH$_2$), with an isocyanate, for example, ethyl isocyanate, in a solvent, for example, dichloromethane, at about ambient temperature.

In another example of an interconversion process, compounds of formula (1), wherein R$^7$ is alkyl, may be prepared by interconversion of a compound of formula (1), where R$^7$ is hydrogen, by reaction with a compound R$^7$L, where L is a leaving group, for example, a halogen atom, such as chlorine, in the presence of a base, for example, lithium diisopropylamide, in a solvent, such as tetrahydrofuran, at low temperature, such as about 0° C.

Compounds of formula (1), wherein R$^3$ corresponds to OR$^9$ where R$^9$ is alkyl, alkoxyalkyl, formyl or alkanoyl, may be prepared in another example of an interconversion process by reaction of a compound of formula (1), where R$^3$ is —OH, with a compound R$^9$L, where R$^9$ is as defined above and L is a leaving group as described above, in a solvent, such as dichloromethane or tetrahydrofuran, in the presence of base, for example, triethylamine or potassium tert-butoxide, at about room temperature.

In a further interconversion process, compounds of formula (1), wherein R$^9$ is carboxamido (—CONHR$^{11}$) .or thiocarboxamido (—CSNHR$^{11}$), may be prepared by reaction of a compound of formula (1), wherein R$^3$ is hydroxyl, with an isocyanate R$^{11}$NCO or an isothiocyanate R$^{11}$NCS, in a solvent, for example, chloroform, in the presence of a base, for example, diisopropylethylamine, at about ambient temperature. The isocyanate R$^{11}$NCO and isothiocyanate R$^{11}$NCS are known compounds and may be prepared in a conventional manner.

In a further example, a compound of formula (1), wherein R$^9$ is CONR$^{11}$R$^{12}$, may be prepared by reaction of a compound of formula (1), wherein R$^9$ is CONHR$^{11}$, with a reagent R$^{12}$L (where L is a leaving group as described above) in the presence of a base, for example, sodium hydride, in a solvent, such as tetrahydrofuran, at low temperature, for example, about 0° C.

In another example, an isothiocyanate of formula (1), where R$^9$ is —CSNR$^{11}$R$^{12}$, may be prepared by reacting a compound of formula (1), wherein R$^9$ is (—CONR$^{11}$R$^{1\,2}$), with a thiation reagent, such as Lawesson's Reagent, in an anhydrous solvent, for example, toluene, at elevated temperature, such as about the reflux temperature.

N-oxides of compounds of formula (1) may be prepared, for example, by oxidation of the corresponding nitrogen base using an oxidizing agent, such as hydrogen peroxide, in the presence of an acid, such as acetic acid, at an elevated temperature, for example, about 70° C. to about 80° C., or alternatively, by reaction with a peracid, such as peracetic acid, in a solvent, for example, dichloromethane, at about ambient temperature.

Salts of the compounds of formula (1) may be prepared by reaction of a compound of formula (1), as a salt or in the free acid or base form, or as a mixture of salt, free acid and/or free base forms, with a suitable acid or base, as appropriate, in a suitable solvent, for example, an organic solvent, including alcohols, such as ethanol or isopropyl alcohol, aromatic hydrocarbons, such as benzene and toluene, or ethers, such as diethyl ether and tetrahydrofuran, using conventional procedures. In general, the reaction for the preparation of a salt may be performed at about ambient temperature or at elevated temperatures, for example, up to about 50° C.

A particular enantiomer of a compound of formula (1) can be produced from a corresponding mixture of enantiomers using any suitable conventional procedure for resolving enantiomers.

Thus, for example, diastereomeric derivatives, for example, salts, may be produced by reaction of a mixture of enantiomers of formula (1), for example, a racemate, and an appropriate chiral compound, for example, a chiral acid or base. Suitable chiral acids include, for example, tartaric acid and other tartrates, such as dibenzoyl tartrates and ditoluoyl tartrates, sulphonates, such as camphor sulphonates, mandelic acid and other mandelates and phosphates, such as 1,1'-binaphthalene-2,2'-diyl hydrogen phosphate. The diastereomers may be separated by any convenient means, for example, by crystallization, and the desired enantiomer recovered, for example, by treatment with an acid or base when the diastereomer is a salt.

In another resolution process, a racemate of formula (1) may be separated using chiral High Performance Liquid Chromatography, for example, as described in the Examples hereinafter.

Alternatively, if desired a particular enantiomer may be obtained by using an appropriate chiral intermediate in one of the processes described above. Thus, for example, a particularly useful method for preparing the individual enantiomers of Examples 15 and 16 involves the initial reaction of an ester of formula (14) with a base, followed by reaction with thionyl chloride and a camphor derivative, such as (+)-exo-10,2-bornanesultam or (−)-endo-10,2-bornanesultam [Aldrich Chem. Co.], followed by reaction of the resulting acyl sultam with a Grignard reagent as described above for the conversion of intermediates of formula (14) to intermediates of formula (13). The resulting intermediate acyl sultam may then be cleaved to the corresponding thioester using a thiol, such as ethane thiol, in a base and the thioester then treated to yield the desired enantiomer of formula (1) using the reactions and conditions described above for the conversion of intermediates of formula (13) to compounds of the invention. This overall process is described in detail in copending U.S. application Ser. No. 08/361,439, filed Dec. 21, 1994 and United Kingdom patent application 9326173.3, filed Dec. 22, 1993, the disclosures of each of which are hereby incorporated by reference herein, in their entirety.

The following examples further illustrate the invention. In the following examples, "DMF" refers to dimethylformamide; "THF" refers to tetrahydrofuran; "DME" refers to dimethoxyethane; "EtOAc" refers to ethyl acetate; "Et$_2$O" refers to diethylether; "Et$_3$N" refers to triethylamine; "BuLi" refers to butyllithium; "LDA" refers to lithium diisopropylamide; "EtOH" refers to ethanol; and RT refers to room temperature.

All $^1$H nmr spectra were obtained at 300 MHz unless specified otherwise.

INTERMEDIATE 1

3-Cyclopentyloxy-4-methoxybenzaldehyde

Cs$_2$CO$_3$ (214 g, 0.66 mol) was added to a mixture of 3-hydroxy-4-methoxybenzaldehyde (100 g, 0.66 mol) and cyclopentyl bromide (98 g, 0.66 mol) in anhydrous DMF (500 ml). The reaction mixture was stirred at RT for 16 h, then treated with a further portion of cyclopentyl bromide (98 g, 0.66 mol) and $Cs_2CO_3$ (214 g, 0.66 mol). After a further 6h at RT, the mixture was filtered and concentrated in vacuo. The residue was dissolved in $CH_2Cl_2$ (300 ml) and washed with NaOH solution (10%, 2×150 ml). The organic layer was dried ($MgSO_4$), concentrated in vacuo, and distilled (150° C., $10^{-2}$ mbar) to afford the title compound (130 g) as a viscous colorless oil. $\delta_H$ ($CDCl_3$) 1.5–2.0 (8H, br m, $CH_2)_4$), 3.87 (3H, s, $OCH_3$), 4.80 (1H, br m, $OCHCH_2$), 6.90 (1H, d, J 8.7 Hz, ArH ortho to OMe), 7.30–7.45 (2H, m, 2×ArH meta to OMe), and 9.77 (1H, s, ArCHO).

INTERMEDIATE 2

(3-Cyclopentyloxy-4-methoxyphenyl)phenylketone

Phenyllithium (1.5M in ether-cyclohexane, 33.5 ml, 50 mmol) was added dropwise to a solution of Intermediate 1 (10.0 g, 45.4 mmol) in THF (50 ml) at about −55° C. The reaction mixture was allowed to warm to RT overnight, then diluted with water (100 ml) and extracted with $Et_2O$ (3×50 ml). The organic extract was washed with aqueous HCl (1%, 70 ml), brine (100 ml), then dried ($MgSO_4$), and concentrated in vacuo to afford 1-(3-cyclopentyloxy-4-methoxyphenyl)-1-phenylmethanol (13.4 g) as a white solid. m.p. 82.5°–83° C.; δH ($CDCl_3$) 1.5–2.0 (8H, br, m, $(CH_2)_4$), 2.30 (1H, br, s, OH), 3.77 (3H, s, OMe), 4.68 (1H, br, m, $OCHCH_2$), 5.77 (1H, s, CHOH), 6.75–6.85 (3H, m, ArH ortho to OMe+2×ArH meta to OMe), and 7.15–7.4 (5H, m, $C_6H_5$); m/z 298 ($M^+$20%), 230 (50), 151 (30), 125 (100), 124 (33), 105 (38), and 92 (22).

The alcohol (prepared above) (13.4 g, 44.8 mmol) was dissolved in $CH_2Cl_2$ (150 ml) and treated with $MnO_2$ (22 g). The reaction mixture was vigorously stirred at RT for 18 h, then treated with a further portion of $MnO_2$ (20 g). More $MnO_2$ (20 g) was added after 10h and the mixture stirred for 18 h, then filtered through Celite® and concentrated in vacuo. The residue was recrystallized from EtOH to afford the title compound (11.27 g; two crops) as a white crystalline solid m.p. 59°–75° C.; δH ($CDCl_3$) 1.5–2.1 (8H,br, m, $(CH_2)_4$), 3.88 (3H, s, OMe), 4.80 (1H, br m, $OCHCH_2$), 6.83 (1H, d, J 8.5 Hz, ArH ortho to OMe), and 7.25–7.8 (7H, m, 2×ArH meta to OMe+$C_6H_5$); m/z 296 ($M^+$11%), 229 (17), 228 (95), 152 (12), 151 (100), 105 (30), 77 (21), and 41 (10).

INTERMEDIATE 3

5-Bromo-2-methoxyphenol

A solution of 5-bromo-2-methoxybenzaldehyde (100 g, 0.46 mol) in $CHCl_3$ (250 ml) was cooled with an ice bath and 3-chloroperoxybenzoic acid (50–60% purity) (146 g, 0.51 mol) in $CHCl_3$ (1000 ml) added. The reaction mixture was allowed to warm slowly to room temperature and stirred for 72h. The white solid was filtered off and the filtrate concentrated in vacuo. The residue was dissolved in $Et_2O$ (200 ml) and washed with 1M sodium sulphite solution (2×200 ml) then $NaHCO_3$ [half saturated] (3×200 ml). The ether layer was washed with 10% aqueous NaOH (3×100 ml) and the combined basic extract was acidified with concentrated hydrochloric acid and extracted with $Et_2O$ (3×100 ml). The combined organic extract was dried ($MgSO_4$) and florisil (10 g) filtered and the solvent removed under reduced pressure to give the title compound (90 g) as a pate brown solid.

INTERMEDIATE 4

4-Bromo-2-cyclopentyloxyanisole

Intermediate 3 (90 g) was dissolved in DMF (300 ml), and treated with $Cs_2CO_3$ (158 g, 490 mmol), and cyclopentyl bromide (73 g, 52.5 ml, 490 mmol). After stirring overnight, further $Cs_2CO_3$ (35 g, 107 mmol) and cyclopentylbromide (12 ml, 16.7 g, 112 mmol) were added and stirring continued for 2 h. Further portions of cyclopentylbromide (10 ml) and $Cs_2CO_3$ were then added (14 g). After stirring for 1 h, the DMF was evaporated in vacuo and the residue diluted with water (200 ml) and extracted with $Et_2O$ (3×100 ml). The combined organic extract was washed with NaOH solution (5%, 2×100 ml), water (100 ml), then dried ($MgSO_4$) and the solvent evaporated in vacuo to give a red oil which was distilled (140° C., 0.3mbar) to afford the title compound (101 g) as a colorless oil (Found: C, 53.11; H, 5.53. $C_{12}H_{15}BrO_2$ requires C, 53.15; H, 5.58%).

INTERMEDIATE 5

(3-Cyclopentyloxy-4-methoxyphenyl)(4-pyridyl)ketone n-BuLi (1.45M in hexanes; 19.6 ml, 28.4 mmol) was added dropwise at −70° C. to a solution of Intermediate 4 (7.0 g, 25.8 mmol) in THF (50 ml). After stirring for 0.25 h, a solution of 4-cyanopyridine (3.08 g, 29.7 mmol) in THF (15 ml) was added and maintained at −70° C. for 0.75 h. The reaction mixture was then allowed to warm to −10° C. and quenched with aqueous HCl (10%; 60 ml). The mixture was stirred for 0.5 h, basified with aqueous NAOH (10%, 70 ml), and extracted with $Et_2O$ (3×70 ml). The extract was washed with brine (100 ml), dried ($MgSO_4$), and concentrated in vacuo. The residue was subjected to chromatography ($SiO_2$; EtOAc/hexane, 4:1) to afford the title compound (6.34 g) as a white powder. δH ($CDCl_3$) 1.5–1.9 (8H, br m, $(CH_2)_4$), 3.90 (3H, s, OMe), 4.82 (1H, br m, $OCHCH_2$), 6.84 (1H, d, J 8.4 Hz, ArH ortho to OMe) 7.29 (1H, dd, J 8.4, 2.0 Hz, ArH para to cyclopentyloxy), 7.4–7.55 (3H, m, ArH ortho to cyclopentyloxy+pyridine $H_3$, $H_5$), and 8.73 (2H, dd, J 4.4 Hz, 1.5 Hz, pyridine $H_2$, $H_6$).

INTERMEDIATE 6

(E) and (Z) Isomers of 4-[1-(3-Hydroxy-4-methoxyphenyl)-2-(4-pyridyl)ethenyl]pyridine A solution of the alcohol of Example 2 (0.72 g, 1.85 mmol) in toluene (120 ml) containing 4-toluenesulphonic acid (0.88 g, 4.6 mmol) was heated to reflux in a Dean-Stark apparatus for 18 h. The cooled reaction mixture was treated with aqueous NaOH (10%) then taken to pH 7 with concentrated hydrochloric acid. The mixture was extracted with $CH_2Cl_2$ (3×40 ml), the extract washed with saturated $NaHCO_3$ (100 ml), and $Na_2CO_3$ (10%;2×60 ml), then dried ($MgSO_4$), and concentrated in vacuo to afford the title compound (0.4 g) as a yellow foam; δH ($CDCl_3$) (major isomer) 3.88 (3H, s, OMe), 6.6–6.9 (6H, m, ArH ortho to OMe+2×ArH meta to OMe+C=CH+pyridine $H_3$, $H_5$), 7.08 (2H, dd, J 4.6, 1.6 Hz, pyridine $H_3$, $H_5$), 8.30 (2H, dd, J 4.5, 1.6 Hz, pyridine $H_2$, $H_6$), and 8.51 (2H, dd, J 4.4, 1.6 Hz, pyridine $H_2$, $H_6$), [the minor isomer displays a signal at δ3.90 (3H, s, OMe)].

INTERMEDIATE 7 a) (E) and (Z) isomers of 4-[2-(3-Cyclopentyloxy-4-methoxyphenyl)-2-phenylethenyl]pyridine The alcohol of Example 1a (3.13 g, 8.05 mmol) was dissolved in toluene (70 ml) containing 4-toluenesulphonic acid monohydrate (1.91 g, 10.05 mmol) and the mixture heated to reflux for 1 h. The reaction mixture was poured into aqueous NaOH (10%; 100 ml) and stirred for 5 min. The mixture was extracted with $Et_2O$ (3×70 ml) and the organic extract washed with water (80 ml), and brine (80 ml), then dried ($MgSO_4$), and concentrated in vacuo to afford a mixture of the title compounds (3.0 g) as a viscous pale yellow oil. $\delta H$ ($CDCl_3$) 1.5–2.1 (8H, br m, $(CH_2)_4$), 3.82 (major) and 3.84 (minor) (3H, s, OMe), 4.8 (1H, br m, $OCHCH_2$), 6.6–7.4 (11H, m, ArH ortho to OMe+2×ArH meta to OMe+$C_6H_5$+pyridine $H_3$, $H_6$), and 8.2–8.35 (2H, m, pyridine $H_2$, $H_6$); m/z 372 ($M^+$+1, 12%), 371 (M+, 40), 304 (21), 303 (100), 302 (72) and 274 (22).

The following compounds were prepared using a similar procedure:

b) (E) and (Z) isomers of 2-[2-(3-Cyclopentyloxy-4-methoxyphenyl)-2-phenylethenyl]pyrazine From the alcohol of Example 1b (570 mg, 1.5 mmol) and 4-toluenesulphonic acid (about 20 mg). Upon completion, the reaction mixture was concentrated in vacuo, then subjected to chromatography ($SiO_2$; $Et_2O$) to afford the title compound (520 mg) as a colorless oil. $\delta H$ ($CDCl_3$) 1.5–2.0 (8H, br m, $(CH_2)_4$), 3.84 and 3.86 (3H, s, OMe), 4.58 and 4.72 (1H, br m, OCH), 6.65–7.5 (9H, m, $C_6H_5$+C=CH+ArH ortho to OMe+2×ArH meta to OMe), 7.90 and 8.04 (1H, d, J 1.5Hz, pyrazine $H_3$), 8.18 and 8.21 (1H, d, J 2.5 Hz, pyrazine $H_6$), and 8.45 and 8.48 (1H, m, pyrazine $H_5$).

c) (E) and (Z) isomers of 3-[2-(3-Cyclopentyloxy-4-methoxyphenyl)-2-phenylethenyl]-2-methoxypyrazine From the compound of Example 7a (2.94 g, 7.0 mmol) and 4-toluenesulphonic acid (about 20mg) as described for Intermediate 7b to afford the title compound (2.67 g) as a yellow oil. $\delta H$ ($CDCl_3$) 1.5–2.0 (8H, br m, $(CH_2)_4$), 3.80, 3.81, 3.83, 3.86 (2×3H, s, 2×OMe), 4.50, 4.70 (1H, br m, OCH), 6.60–7.5 (9H, m, $C_6H_5$+C=CH+ArH ortho to OMe+2×ArH meta to OMe) and 7.7–7.95 (2H, m, pyrazine $H_5$, $H_6$).

d)(i) (E) 4-2-(3-Cyclopentyloxy-4-methoxyphenyl)-2-phenylethenyl]-3.5-dichloropyridine

(ii) (Z) 4-[2-(3-Cyclopentyloxy-4-methoxyphenyl)-2-phenylethenyl]-3,5-dichloropyridine From the compound of Example 1c (1.60 g, 3.58 mmol) and 4-toluenesulphonic acid (0.85 g). Purification by column chromatography ($SiO_2$; $CH_2I_2$) afforded:

i) (E) title compound (960 mg) as an off-white solid m.p. 138.5°–140° C. $\delta H$ ($CDCl_3$) 1.5–2.0 (8H, br m, $(CH_2)_4$), 3.88 (3H, s, OMe), 4.72 (1H, br m, OCH), 6.59 (1H, s, C=CH), 6.85 (1H, d, J 8.4Hz, ArH ortho to OMe), 6.90 (1H, d, J 2.0Hz, ArH ortho to cyclopentyloxy), 6.95 (1H, dd, J 8.4, 2.0Hz, ArH para to cyclopentyloxy), 7.0–7.1 (2H, m, $H_2$, $H_6$ of $C_6H_5$), 7.15–7.3 (3H, m, $H_3$, $H_4$, $H_5$ of $C_6H_5$), and 8.35 (2H, s, pyridine $H_2$, $H_6$).

and ii) (Z) title compound (240 mg) as an off-white solid. m.p. 155°–156.5° C. $\delta H$ ($CDCl_3$) 1.4–1.8 (8H, br m $(CH_2)_4$), 3.80 (3H, s, OMe), 4.42 (1H, br m OCH), 6.52 (1H, d, J 2.0 Hz,m ArH ortho to cyclopentyloxy), 6.56 (1H, s, C=CH), 6.57 (1H, dd, J 8.4, 2.0 Hz, ArH para to cyclopentyloxy), 6.68 (1H, d, J 8.4 Hz, ArH ortho to OMe), 7.3–7.45 (5H,m, $C_6H_5$), and 8.37 (2H, s, pyridine $H_2$, $H_6$).

e) (E) and (Z) isomers of 3-[2-(3-Cyclopentyloxy-4-methoxyphenyl)-2-phenylethenyl]pyridazine From a compound of Example 7b (4.0 g). Purification by chromatography ($SiO_2$; $Et_2O$) afforded the title compound (2.07 g) as a pale yellow solid (Found: C, 77.59; H, 6.49; N, 7.24. $C_{24}H_{24}N_2O_2$ requires C, 77.39; H, 6.50; N, 7.52%); $\delta H$ ($CDCl_3$) 1.5–1.9 (8H, br m, $(CH_2)_4$), 3.88,3.90 (3H, s, OMe), 4.58, 4.70 (1H, br m, OCH), 6.6–7.5 (11H, M, $C_6H_5$+$C_6H_3$+C=CH+pyridazine $H_4$, $H_{5+}$), and 8.85–8.90 (1H, m, pyridazine $H_6$) ($^1$H nmr indicates a 3:2 E/Z ratio); m/z (ESI) 396 ($M+_+1$+Na, 57%), 395 ($M^+$+Na, 100), 374 (66), 373 (78), and 305 (16).

f) (E) and (Z) isomers of 2-[2-(3-Cyclopentyloxy-4-methoxyphenyl)-2-phenylethenyl]-4-methylpyridine From a compound of Example 7c (1.15 g, 2.85 mmol). Purification by chromatography ($SiO_2$; EtOAc) afforded the title compound (1.2 g) as a pale yellow solid; $\delta H$ ($CDCl_3$) 1.4–1.9 (8H, br m, $(CH_2)_4$), 2.04 (major), 2.09 (minor) (3H, pyridine Me), 3.85 (major), 3.88 (minor) (31t, s, OMe), 4.58 (minor, 4.72 (major) (1H, br m, OCH), 6.4–7.5 (11H, m, $C_6H_5$+$C_6H_3$+pyridine $H_3$, $H_5$+C=CH), 8.5–8.55 (1H, m, pyridine $H_6$). $^1$H nmr indicates a 2:1 E/Z ratio.

g) (E) and (Z) isomers of 4-[2-(3-Cyclopentyloxy-4-methoxyphenyl)-2-phenylethenyl]pyrimidine From a compound of Example 7d (2.55 g). Purification by chromatography ($SiO_2$; $Et_2O$) afforded the title compound (1.20 g) as a pale yellow foam; $\delta H$ ($CDCl_3$) 1.5–2.0 (8H, br m, $(CH_2)_4$), 3.88, 3.90 (3H, s, OMe), 4.60, 4.70 (1H, br m, OCH), 6.44, 6.64 (1H, d, J 5.2Hz, pyrimidine $H_5$), 6.65–7.0 (3H, m, $C_6H_3$), 7.2–7.45 (6H, m, $C_6H_5$+C=CH), 8.26, 8.32 (1H, d, J 5.2Hz, pyrimidine $H_6$), and 9.10, 9.12 (1H, ca s, pyrimidine $H_2$).

INTERMEDIATE 8

(E) and (Z) isomers of 4-[1-(3-Cyclopentyloxy-4-methoxyphenyl)-2-(4-pyridyl)ethenyl]pyridine A mixture of Intermediate 6 (0.48 g, 1.58 mmol), $Cs_2CO_3$ (0.56 g, 1.73 mmol), and cyclopentyl bromide (0.26 g, 1.743 mmol) in DMF (20 ml) was stirred at RT overnight. A further portion of $Cs_2CO_3$ (0.20 g,0.61 mmol) and cyclopentyl bromide (0.28 g, 1.86 mmol) was added, the mixture stirred for 1.5h then concentrated in vacuo. The residue was subjected to chromatography ($SiO_2$; EtOAc/$CH_3OH$/$Et_3N$, 100:1:0.4)to afford the title compound (0.42 g) as a white solid. m.p. 136°–138° C. (cyclohexane); $\delta H$ ($CDCl_3$) 1.5–2.0 (8H, m $(CH_2)_4$), 3.84 (3H, s, OMe), 4.65 (1H, br m $OC_HCH_2$), 6.7–6.9 (6H, m, ArH ortho to OMe+2×ArH meta to OME+C=CH+pyridine $H_3$,$H_5$), 7.08 (2H, dd, J 4.5, 1.5 Hz, pyridine pyridine $H_3'$, $H_5'$), 8.32 (2H, dm, J 5.0 Hz pyridine $H_2$, $H_6$), and 8.55 (2H, dd, J 4.5, 1.5Hz, pyridine $H_2'$, $H_6'$); m/z 372 ($M^+$28%), 305 (37), 304 (100), 303 (95), 275 (18), and 41 (18).

INTERMEDIATE 9

1-(3-Cyclopentyloxy-4-methoxyphenyl)-1-phenylethene

To a cold suspension (0° C.) of methyl triphenylphosphonium bromide (53.6 g; 0.15 mol) in THF (500 ml) under a nitrogen atmosphere was added n-BuLi (1.6M in hexanes; 94 ml, 0.15 mol) dropwise and the reaction mixture stirred at 0° C. for 1 h. A solution of Intermediate 2 (29.6 g, 0.1 mol) in THF (100 ml) was added dropwise and the stirred reaction mixture allowed to warm to RT over 3 h. The mixture was poured into 10% $NH_4Cl$ solution (600 ml) and extracted with $CH_2Cl_2$ (2×500 ml). The combined organic layer was dried ($MgSO_4$), filtered and concentrated in vacuo. The residual slurry was triturated with hot hexane. (500 ml), the precipitated phosphine oxide filtered off and the filtrate evaporated in vacuo to yield the title compound (28.85 g) as a yellow oil. $\delta H$ ($CDCl_3$) 1.5–2.0 (8H, br m, $(CH_2)_4$), 3.85 (3H, s, OMe), 4.71 (1H, br m, OCH), 5.38 (2H, dd, J 10.5, 1.3 Hz, C=$CH_2$), 6.75–6.9 (3H, m, $C_6H_3$), and 7.3–7.5 (5H, m, $C_6H_5$).

INTERMEDIATE 10 a) (E) and (Z) isomers of 4-[2-(3-Cyclopentyloxy-4-methoxyphenyl)-2-phenylethenyl]phenol A mixture of Intermediate 9 (2.94 g, 10 mmol), 4-bromophenol (2.16 g, 12.5 mmol), $Et_3N$ (2.52 g, 25 mmol), tri-o-tolyl phosphine (0.06 g, 0.2 mmol) and palladium acetate (0.022 g, 0.1 mmol) was heated in a bomb at 140° C. for 16 h. Upon cooling, the reaction mixture was diluted with $NH_4Cl$ (10%; 50 ml) and $CH_2Cl_2$ (50 ml). The organic layer was separated and the aqueous layer extracted with $CH_2Cl_2$ (50 ml). The combined organic layer was dried ($MgSO_4$), filtered and concentrated. Purification by column chromatography ($SiO_2$; hexane/$Et_2O$,1:1) yielded the title compound (1:1 mixture of isomers) (0.8 g) as a yellow foam. 5H ($CDCl_3$) 1.2–1.9 (BH, br m, $(CH_2)_4)_4$), 3.81, 3.83 (3H, s, OMe), 4.59, 4.69 (1H, br m, OCH), 5.5, 5.63 (1H, br s, OH), 6.55–7.0 (8H, M, $C_6H_3$+$C_6H_4$+C=CH), and 7.15–7.35 (5H, m, $C_6H_5$) [N.B. $^1H$ nmr ca 1:1 E/Z mixture of isomers); 410 ($M^+$+1+Na, 18%), 409 ($M^+$+Na, 100) 387 ($M^+$+1, 62), 319 (38), 318 (22), 301 (19), 236 (22), and 135 (20).

The following compounds were prepared using a similar procedure:

b) (E) and (Z) isomers of 3-[2-(3-Cyclopentyloxy-4-methoxyphenyl)-2-phenylethenyl]benzoic acid From Intermediate 9 (2.94 g, 10 mmol) and 3-bromobenzoic acid (5.03 g, 25 mmol). Purification by column chromatography [$SiO_2$;10%, $CH_3OH$/$CH_2Cl_2$] furnished the title compounds (2 g) as a viscous yellow oil. $\delta H$ ($CDCl_3$) 1.45–2.0 (8H, br m, $(CH_2)_4$), 3.86, 3.87 (3H, s, OMe), 4.55, 4.7 (1H, br m, OCH), 6.65–8.25 (13H, m, $C_6H_5$+$C_6H_4$+$C_6H_3$+C=CH), ($CO_2H$ not observed) [N.B. $^1H$ nmr indicates ca 1:1 E/Z mixture of isomers]; m/z (ESI) 437 ($M^+$+23, 60%), 301 (67), 281 (100), and 259 (52).

c) (E) and (Z) isomers of 4-[2-(3-Cyclopentyloxy-4-methoxyphenyl)-2-phenylethenyl]anisole From Intermediate 9 (1.19 g, 4.04 mmol) and 4-bromoanisole (0.757 g, 4.05 mmol). Purification by column chromatography [$SiO_2$; hexane/$Et_2O$, 4:1] furnished the title compounds (0.78 g) as a yellow oil. $\delta H$ ($CDCl_3$) 1.5–2.0 (8H, br m, $(CH_2)_4$), 3.72, 3.73 (3H, s, OMe), 3.82, 3.86 (3H, s, OMe), 4.58, 4.67 (1H, br m, OCH), 6.6–6.9 (6H, M, $C_6H_3$+2×ArH ortho to OMe+C=CH), 6.93, 7.00 (2H, d, J 8.5Hz, 2×ArH meta to OMe) and 7.15–7.35 (5H, m, $C_6H_5$) [N.B. $^1H$ nmr indicates ca 1:1 E/Z mixture of isomers]; m/z (ESI) 424 ($M^+$+1+Na, 20%), 423 ($M^+$+Na, 100%), 374 (12), 281 (20), 198 (12), 132 (12) and 86 (12).

d) (E) and (Z) isomers of Methyl 4-[2-(3-Cyclopentyloxy-4-methoxyphenyl)-2-phenylethenyl]benzoate From Intermediate 9 (2.94 g, 10 mmol) and methyl 4-bromobenzoate (2.69 g, 12.5 mmol) to afford the title compounds (3.35 g) as a yellow gum; $\delta H$ ($CDCl_3$) 1.4–2.0 (8H, br m, $(CH_2)_4$), 3.86, 3.87 (6H, s, OMe+$CO_2Me$), 4.54, 4.67 (1H, br m, OCH), 6.6–7.4 (11H, m, $C_6H_5$+$C_6H_3$+C=CH+2×ArH meta to $CO_2Me$), and 7.75–7.85 (2H, m, 2×ArH ortho to $CO_2Me$) [N.B. $^1H$ nmr indicates ca 1:1 E/Z mixture of isomers]; m/z (ESI) 429 ($M^+$+1+Na, 28%), 362 (18), 361 (28), 330 (70), and 329 (68).

e) (E) and (Z) isomers of 3-[2-(3-Cyclopentyloxy-4-methoxyphenyl)-2-phenylethenyl]pyridine From Intermediate 9 (1.00 g, 3.4 mmol) and 3-bromopyridine (1.28 g, 8.1 mmol). Purification by chromatorgaphy ($SiO_2$; $Et_2O$) afforded the title compound (0.50 g) as a pale yellow gum; $\delta H$ ($CDCl_3$) 1.45–2.0 (8H, br m, $(CH_2)_4$), 3.85 (major), 3.87 (minor) (3H, s, OMe), 4.55 (minor), 4.69 (major) (1H, br m, OCH), 6.65–7.5 (11H, m, $C_6H^5$+$C_6H_3$+ pyridine $H_4$, $H_5$+C=C), and 8.2–8.45 (2H, m, pyridine $H_2$,$H_6$).

INTERMEDIATE 11

(E) and (Z) isomers of 4-[2-(3-Cyclopentyloxy-4-methoxyphenyl)-2-phenylethenyl]acetoxybenzene To a stirred solution of Intermediate 10a (0.2 g, 0.52 mmol) in $CH_2Cl_2$ (5 ml), under a nitrogen atmosphere, was added $Et_3N$ (0.101 g, 0.14 ml, 1 mmol) followed by acetyl chloride (0.0785 g, 0.071 ml, 1 mmol). The reaction mixture was stirred at RT for 4h then poured into saturated $NaHCO_3$ (10 ml). The organic layer was separated and the aqueous layer extracted with $CH_2Cl_2$. The combined organic layer was dried ($MgSO_4$), filtered, and the solvent removed in vacuo to furnish the title compounds (0.222 g) as a colorless oil. 5H ($CDCl_3$) 1.5–1.9 (8H, br m, $(CH_2)_4$), 2.23, 2.24 (3H, s, OCOMe), 3.83, 3.86 (3H, s, OMe), 4.56, 4.67 (1H, br m, OCH), and 6.7–7.4 (13H, m, $C_6H_5$+$C_6H_4$+$C_6H_3$+C=CH) [N.B. $^1H$ nmr indicates ca 1:1 E/Z mixture of isomers]; m/z (ESI) ($M^+$+Na, 100%), 319 (20), 281 (29), 191 (48), 127 (50) and 55 (54).

INTERMEDIATE 12

(E) and (Z) isomers of Methyl 3-[2-(3-cyclopentyloxy-4-methoxyphenyl)-2-phenylethenyl]benzoate To a cold (0° C.) solution of Intermediate 10b (0.25 g, 0.6 mmol) in $CH_3OH$ (20 ml) was added $SOCl_2$ (0.357 g, 0.22 ml, 3 mmol) dropwise and the reaction mixture was stirred at RT for 3 h. The solvent was evaporated in vacuo, the residue dissolved in $CH_2Cl_2$ (20 ml) and washed with saturated $NaHCO_3$ (20 ml). The organic phase was separated and the aqueous phase extracted with $CH_2Cl_2$ (20 ml). The combined organic layer was dried ($MgSO_4$), filtered and the solvent evaporated in vacuo to yield the title compound (0.215 g) as a yellow oil. δH (CDCl$_3$) 1.4–2.0 (8H, br m, (CH$_2$)$_4$), 3.82, 3.83, 3.84, 3.85 (6H, s, OMe+CO$_2$Me), 4.54, 4.69 (1H, br m, OCH), and 6.65–7.85 (13H, m, C$_6$H$_5$+ C$_6$H$_4$+C$_6$H$_3$+C=CH) [N.B. $^1$H nmr indicates ca 1:1 E/Z mixture of isomers]; m/z (ESI)$_{429}$ (M$^+$+1, 25%), 361 (22), 329 (100), 159 (12), 102 (15), and 60 (75).

INTERMEDIATE 13

Ethyl (E)-(3-Cyclopentyloxy-4-methoxyphenyl)-2-(4-pyridyl)propenoate

A mixture of Intermediate 1 (26.62 g, 0.12 mol), ethyl 4-pyridylacetate (19.92 g, 0.12 mol, 1 eq) and ammonium acetate (18.63 g, 0.24 g, 2eq) in glacial acetic acid (200 ml) was stirred at 120° C. under nitrogen for 20 h. The solution was cooled to RT and the acid removed in vacuo. The orangy/brown residue was taken up in saturated NaHCO$_3$ solution to pH 8.5 and the aqueous layer extracted several times with EtOAc. The combined organic layer was washed (brine), dried (MgSO$_4$) and evaporated to dryness to give a yellow solid. Recrystallisation from toluene/hexane (1st crop) then toluene (2nd crop) followed by column chromatography (hexane-EtOAc/hexane, 7:3) gave the title compound as a white crystalline solid. m.p. 109°–110° C. δH (CDCl$_3$) 1.27(3H, t, J 7.1Hz, CH$_2$CH$_3$), 1.45–1.8 (8H, br m, cyclopentyl H's), 3.81 (3H, s, OMe), 4.16 (1H, br m, OCH), 4.25 (2H,q, J 7.1 Hz, CH$_2$CH$_3$), 6.43 (1H, d J 2.0 Hz, ArH ortho to cyclopentyloxy), 6.73 (1H, d, J 8.4 Hz, ArH ortho to OMe), 6.80 (1H, dd, J 2.0, 8.4 Hz, ArH para to cyclopentyloxy), 7.22 (2H, dd, J 1.6, 4.5Hz, pyridine H$_3$, H$_5$,), 7.83 (1H, s, HC=C) and 8.64 (2H, dd, J 1.6, 4.5 Hz, pyridine H$_2$, H$_6$).

INTERMEDIATE 14

Ethyl 3-(3-Cyclopentyloxy-4-methoxyphenyl)-3-;(4-fluorophenyl)-2-(4-pyridyl)propanoate 4-Fluorophenylmagnesium bromide (2M in Et$_2$O; 20.4 ml, 40.8 mmol) was added dropwise at –40° C. over 20 min to a suspension of copper (I) bromide-dimethyl sulphide complex (4.17 g, 20.4 mmol) in THF (50 ml). The reaction mixture was warmed to –10° C. over 15 min and a solution of Intermediate 13 (5 g, 13.6 mmol) in THF (25 ml) was added dropwise over 15 min. The reaction mixture was allowed to warm slowly (about 2h) to RT, and quenched with saturated aqueous NH$_4$Cl (30 ml). The organic phase was extracted and evaporated. The concentrate was partitioned between EtOAc (150 ml) and water (50 ml) and filtered through Celite®. The organic extract was washed with 10% NH$_4$OH (2×100 ml) and brine (100 ml), dried (MgSO$_4$) and evaporated to give a pale yellow gummy solid. Trituration with hot Et$_2$O provided a white solid which was filtered off and washed with cold Et$_2$O. Purification by column chromatography (SiO$_2$; EtOAc/hexane, 1:1) furnished the title compound (2.2 g) as a single isomer. δH (CDCl$_3$) 1.05 (3H, t, COCH$_2$CH$_3$), 1.6–2.0 (8H, br m, (CH$_2$)$_4$), 3.80 (3H, s, OCH$_3$), 4.0 (2H, m, COCH$_2$), 4.30 (1H, d, CHAr), 4.60 (1H, d, CHCO$_2$Et), 4.80 (1H, m, OCHCH$_2$), 6.75–7.0 (7H, m, At), 7.25 C$_2$H, d, Ar), 8.45 (2H, d, Ar).

INTERMEDIATE 15

3,5-Dichloro-4-methylpyridine 3,5-Dichloropyridine (2.04 g, 13.5 mmol) in THF (5 ml) was added dropwise to a solution of LDA [prepared from diisopropylamine (1.9 ml, 13.5 mmol) and $_n$-BuLi (1.6M; 8.4 ml, 13.5 mmol)] in THF (25 ml) at –70° C. After stirring at this temperature for 5 min, iodomethane (0.85 ml, 13.5 mmol) was added and the reaction mixture stirred for a further 1.5h at –70° C. Saturated NaHCO$_3$ (20 ml) and CH$_2$Cl$_2$ (20 ml) were added, the organic phase separated, dried (MgSO$_4$), and concentrated in vacuo. The residue was subjected to chromatography (SiO$_2$; Et$_2$O/hexane, 1.:3) to afford the title compound (1.16 g) as a pale yellow solid. δH (CDCl$_3$) 2.46 (3H, s, Me), and 8.36 (2H, s, pyridine H$_2$, H$_6$).

INTERMEDIATE 16

Ethyl 3-(3-Cyclopentyloxy-4-methoxyphenyl)-2-ethoxycarbonylpropenoate

A mixture of Intermediate 1 (109.8 g, 499.1 mmol), diethyl malonate (79.96 g, 499.1 mmol), piperidine (2.5 ml) and CH$_3$CO$_2$H (12 ml) in toluene (700 ml) was heated to reflux in a Dean-Stark apparatus for 20 h. Further portions of diethyl malonate (9.6 g, 59.9 mmol), piperidine (2.5 ml), and CH$_3$CO$_2$H (12 ml) were added and heating continued as before for 15 h. The reaction mixture was concentrated in vacuo to afford the title compound (217 g) as a brown oil. δH (CDCl$_3$) 1.33 (6H, t, J 7.1 Hz, 2×CO$_2$CH$_2$Me), 1.5–2.05 (8H, br m, (CH$_2$)$_4$), 3.88(3H, s, OMe), 4.30 (2H, q, J Hz, CO$_2$CH$_2$Me), 4.36 (2H, q, J 7.1 Hz, CO$_2$CH$_2$,Me), 4.73 (1H, br m, OCH), 6.85 (1H, d, J 8.1 Hz, ArH ortho to OMe), 7.0–7.1 (2H, m, 2×ArH meta to OMe), and 7.63 (1H, s, HC=CCO$_2$Et).

INTERMEDIATE 17

Diethyl 2-[(3-Cyclopentyloxy-4-methoxyphenyl)phenylmethy]propan-1-3-dioate

Phenylmagnesium bromide (1.0M in THF; 340 ml, 340 mmol, 1.29 eq) was added over 1.5 h to a solution of Intermediate 16 (95.6 g, 264 mmol) in THF (200 ml) at –60° C. and stirred at this temperature for a further 5 h. The reaction mixture was allowed to warm to –20° C., quenched with 10% aqueous NH$_4$Cl (200 ml), then extracted with EtOAc (3×100 ml). The extract was dried (MgSO$_4$), concentrated in vacuo, the residual brown oil dissolved in EtOH and allowed to crystallise overnight to afford the title compound (74.9 g) as a white solid. m.p. 97°–98° C. δH (CDCl$_3$) 1.01 (6H, t, J 7.1 Hz, CO$_2$CH$_2$Me), 1.05 (3H, t, J 7.1 Hz, CO$_2$CH$_2$Me), 1.5–2.0 (8H, br M, (CH$_2$)$_4$), 3.77 (3H, s, OMe), 3.9–4.1 (4H, m, 2×CO$_2$CH$_2$Me), 4.26 (1H, d, J, 12.1 Hz, CHCHCO$_2$Et), 4.67 (1H, d, J 12.1 Hz, CHCHCO$_2$Et), 4.71 (1H, br m, OCH), 6.7–6.85 (3H, m, C$_6$H$_3$), and 7.15–7.35 (5H, M, C$_6$H$_5$).

INTERMEDIATE 18

3-(3-Cyclopentyloxy-4-methoxyphenyl)-3-phenyl-propanoic acid

A mechanically stirred solution of Intermediate 17 (70.3 g, 0.160 mol) in NaOH solution (8M; 600 ml) and dioxane (600 ml) was heated to reflux for 7 h. The reaction mixture was cooled, concentrated hydrochloric acid (about 400 ml) was added dropwise to pH 4 and heating carried overnight to give a homogenous solution. The dioxane was removed in vacuo and the mixture partitioned between CH$_2$Cl$_2$ (500 ml) and H$_2$O (500 ml). The organic layer was separated and combined with further CH$_2$Cl$_2$ extracts (3×150 ml). The extract was dried (MgSO$_4$) and concentrated in vacuo to give the title compound (55 g) as a yellow solid. δH (CDCl$_3$)

1.5–2.0 (8H, br m, (CH$_2$)$_4$), 3.04 (2H, d, J 7.9Hz, CHCH$_2$CO$_2$H), 3.80 (3H, s, OMe), 4.45 (1H, t, J 7.9Hz CHCH$_2$CO$_2$H), 4.70 (1H, br m, OCH), 6.7–6.8 (3H, m, C$_6$H$_3$), and 7.15–7.35 (5H, m, C$_6$H$_5$). (N.B. CO$_2$H not observed).

INTERMEDIATE 19

3-(3-Cyclopentyloxy-4-methoxyphenyl)-3-phenyl-propanoyl chloride

SOCl$_2$ (14.8 ml, 24.1 g, 3 eq) was added to a solution of Intermediate 18 (23.0 g, 67.5 mmol) in CH$_2$Cl$_2$ (250 ml) and then heated to reflux for 6 h. The reaction mixture was allowed to stir at RT overnight then concentrated in vacuo to afford the title compound (23.7 g) as a dark brown oil. δH (CDCl$_3$) 1.5–2.0 (8H, br m, (CH$_2$)$_4$), 3.62 (2H, d, J 8.0 Hz, CHCH$_2$COCl), 3.82 (3H, s, OMe), 4.56 (1H, t, J 8.0Hz, CHCH$_2$COCl), 4.73 (1H, br m, OCH), 6.7–6.85 (3H, m, C$_6$H$_3$), and 7.15–7.4 (5H, M, C$_6$H$_5$)

INTERMEDIATE 20

5-(3-Cyclopentyloxy-4-methoxyphenyl)-1-[2-(1,3-dioxolanyl)]-5-phenyl-3-pentanone A solution of the Grignard reagent (1.0M in THF, 29 ml, 29.0 mmol, 1.2 eq) [prepared from 2-(2-bromoethyl)-1,3-dioxolane (5.25 g, 29.0 mmol) and magnesium (10.8 g, 33 mmol)] was added dropwise at −70° C. to a solution of Intermediate 19 (8.7 g, 24.3 mmol) in THF (200 ml). The reaction mixture was stirred at −70° C. for 0.5 h, allowed to warm to RT over 1.75 h then partitioned between Et$_2$O (200 ml) and aqueous NaOH (1M; 100 ml). The organic layer was separated and combined with a further Et$_2$O extract (150 ml). The extract was washed with brine (50 ml), dried (MgSO$_4$) and concentrated in vacuo. Purification by column chromatography (SiO$_2$; 20% EtOAC/hexane) furnished the title compound (3.95 g) as an off-white waxy solid. m.p. 60°–62° C. δH (CDCl$_3$) 1.5–2.0 (10H, br m, (CH$_2$)$_4$+ CH$_2$CH$_2$CO), 2.46 (2H, t, J 7.5Hz, CH$_2$CH$_2$CO), 3.13 (2H, d, J 7.6 Hz, CHCH$_2$CO), 3.7–4.0 (4H, m, O(CH$_2$)$_2$O, 3.78 (3H, s, OMe), 4.53 (1H, t, J 7.6 Hz, CHCH$_2$CO), 4.68 (1H, m, ArOCH), 4.80 (1H, t, J 4.3 Hz, OCHO), 6.65–6.8 (3H, m, C$_6$H$_3$), and 7.1–7.3 (5H,m, C$_6$H$_5$).

INTERMEDIATE 21

6-(3-Cyclopentyloxy-4-methoxyphenyl-4-oxo-6-phenyl-1-hexanal

A solution of Intermediate 20 (800 mg) in a mixture of aqueous HCl (2M; 5 ml) and THF (15 ml) was heated at about 45° C. for 1.5 h. The reaction mixture was concentrated to low volume (about 5 ml) and partitioned between Et$_2$O (50 ml) and H$_2$O (10 ml). The organic layer was separated and combined with a further Et$_2$O extract (30 ml). The extract was washed with saturated NaHCO$_3$ (40 ml), then brine (10 ml), dried (MgSO$_4$) and concentrated in vacuo. The residual orange oil was subjected to chromatography (SiO$_2$; Et$_2$O-hexane) to afford the title compound (450 mg) as a pale yellow oil. δH (CDCl$_3$) 1.5–2.0 (8H, br m, (CH$_2$)$_4$), 2.6–2.7 (4H, m, CH$_2$CH$_2$CHO), 3.19 (2H, d, J 7.6Hz, CHCH$_2$CO), 3.79 (3H, s, OMe), 4.52 (1H, t, J 7.6Hz, CHCH$_2$CO), 4.70 (1H, br m, OCH), 6.7–6.8 (3H, m, ArH ortho to OMe+2×ArH meta to OMe), 7.1–7.3 (5H, m, C$_6$H$_5$), and 9.71 (1H, s, CH$_2$CHO).

INTERMEDIATE 22

Ethyl 5-(3-Cyclopentyloxy-4-methoxyphenyl)-3-oxo-5-phenylpentanoate n-BuLi (1.6M in hexanes; 29.3 ml, 46.9 mmol, 4.2 eq) was added dropwise at −50° C. to a solution of potassium ethyl malonate (2.95 g, 22.3 mmol, 2.1 eq) in; THF (60 ml). The reaction mixture was allowed to warm to −10° C., stirred for 10 min, then recooled to −65° C. and treated dropwise with a precooled solution of Intermediate 19 (4.0 g, 11.1 mmol) in THF (20 ml). The reaction mixture was stirred at −65° C. for 20 min, then poured into a stirred mixture of Et$_2$O (100 ml) and aqueous HCl (1M; 150 ml). After 0.5 h, the organic phase was separated and combined with further Et$_2$O extracts (2×75 ml). The extract was dried (MgSO$_4$), concentrated in vacuo, and the residual oil subjected to chromatography (SiO$_2$; 40% Et$_2$O-hexane) to afford a colorless oil (3.4 g) which crystallised on standing to give the title compound as a white solid. m.p. 56°–58° C. (EtOH). δH (CDCl$_3$) 1.24 (3H, t, J 7 Hz, CO$_2$CH$_2$Me), 1.5–1.9 (8H, br m, (CH$_2$)$_4$), 3.27 (2H, d J 7.5Hz, CHCH$_2$CO), 3.33 (2H, s, CH$_2$CO$_2$Et), 3.79 (3H, s, OMe), 4.14 (2H, q, J 7 Hz, CO$_2$CH$_2$Me), 4.52 (1H, t, J 7.5Hz, CHCH$_2$CO), 4.69 (1H, m, OCH), 6.7–6.8 (3H, M, C$_6$H$_3$), and 7.1–7.35 (5H, M, C$_6$H$_5$).

INTERMEDIATE 23

(±) 4-[2-(3-Hydroxy-4-methoxyphenyl)phenylethyl] pyridine

The compound of Example 3a (430 mg) in dioxane/water (20 ml:10 ml) containing concentrated H$_2$SO$_4$ (10 ml) was heated at 90° C. for 1 h. The reaction mixture was cooled, neutralised with aqueous NaHCO$_3$ then concentrated in vacuo. The residue was partitioned between EtOAc (25 ml) and H$_2$O (15 ml), and the organic phase separated. The extract was washed with brine (25 ml), dried (MgSO$_4$) and concentrated in vacuo. The residue was recrystallised (EtOH) to afford the title compound (240 mg) as an off-white crystalline solid m.p. 195°–197° C. (Found: C, 78.66; H, 627; N, 4.59. C$_{20}$H$_{19}$NO$_2$ requires C, 78.64; H, 6.18; N, 4.42%); δH (CDCl$_3$) 3.30 (2H, d, J 8 Hz, CHCH$_2$), 3.86 (3H, s, OMe), 4.13 (1H, t, J 8Hz, CHCH$_2$), 5.7 (1H, br s, OH), 6.63 (1H, dd, J 8.3 Hz, ArH para to OH), 6.71 (1H, d, J 8.3Hz, ArH ortho to OMe), 6.80 (1H, d, J 2.2Hz, ArH ortho to OH), 6.93 (2H, dd, J 4.5, 1.5Hz, pyridine H$_3$, H$_5$), 7.1–7.3 (5H, m, C$_6$H$_5$), and 8.37 (2H, dd, J 4.5,1.5 Hz, pyridine H$_5$-,H$_6$).

INTERMEDIATE 24

(2S*,3S*) and (2S*,3R*) Ethyl 3-(3-Cyclopentyloxy)-4-methoxyphenyl)-3-[4-(1,3-dioxolanyl)phenyl]-2-pyridyl]propanoate 2-(4-bromophenyl)-1,3-dioxolane (3.25 g, 14.2 mml) in THF (10 ml) was added dropwise to a stirred suspension of magnesium turnings (358 mg, 14.8 mmol) in THF (5 ml) at 40°–45° C. The resulting green solution was allowed to cool to RT and copper (I) chloride (28 mg, 0.28 mmol) was added. The reaction mixture was cooled to −30° C., Intermediate 13 (4.34 g, 11.8 mmol) in THF (15 ml) added at −25° C. to −30° C., then stirred for 1 h at −20° C. and allowed to warm to RT over 2 h. Saturated aqueous NH$_4$Cl (20 ml) was added, THF removed in vacuo and the concentrate partitioned between Et$_2$O (50 ml) and water (50 ml).

The organic layer was separated, washed with brine (20 ml), dried (MgSO$_4$), and concentrated in vacuo. The residue was subjected to chromatography (SiO$_2$; Et$_2$O to Et$_2$O-EtOAc, 1:1) to afford i) (2S*,3R*)-title compound (1.45 g) as a colorless gum; δH (CDCl$_3$) 1.02 (3H, t, J 7.1 Hz, CO$_2$CH$_2$Me), 1.5.–2.0 (8H, br m, (CH$_2$)$_4$), 3.70 (3H, s, OMe), 3.8–4.2 (6H, complex m, O(CH$_2$)O+CO$_2$CH$_2$Me), 4.35 (1H, d, J 8.0 Hz, CHCHCO$_2$Et), 4.55 (1H, br m, OCH), 4.60 (1H, d, J 8.0Hz, CHCHCO$_2$Et), 5.78 (1H, s, OCHO), 6.5–6.65 (3H, m, C$_6$H$_3$), 7.22 (2H, d, J 6.0 Hz, pyridine H$_3$, H$_5$), 7.35–7.5 (4H, m, C$_6$H$_4$), and 8.45 (2H, d, J 6.0Hz, pyridine H$_2$,H$_6$) and ii) (2S*,3S*)-title compound (1.45 g) as a white solid; δH (CDCl$_3$) 1.03 (3H, t, J 7.1Hz, CO$_2$CH$_2$Me), 1.5–2.0 (8H, br m, (CH$_2$)$_4$), 3.80 (3H, s, OMe), 3.9–4.1 (6H, complex m, O(CH$_2$)O+CO$_2$CH$_2$Me), 4.36 (1H, d, J 8.0 Hz, CHCHCO$_2$Et), 4.60 (1H, d, J 8.0Hz, CHCHCO$_2$Et), 4.78 (1H, br m, OCH), 5.66 (1H, s, OCHO), 6.78 (1H, d, J 8.2Hz, ArH of C$_6$H$_3$), 6.85–6.95 (2H, m, 2×ArH of C$_6$H$_3$), 7.08 (2H, d, J 6.0 Hz, 2×ArH of CH$_6$H$_4$), 7.15–7.3 (4H, m, 2×ArH of C$_6$H$_4$+pyridine H$_3$, H$_5$), and 8.42 (2H, ca, J 6.0 Hz, pyridine H$_2$,H$_6$).

INTERMEDIATE 25

(S*,R*) and (S*,S*) Ethyl 3-(3-Cyclopentyloxy-4-methoxyphenyl)-3-(4-trifluoromethylphenyl)-2-(4-pyridyl)propanoate 4-Bromo(trifluoromethyl)benzene (3.43 ml, 24.5 mmol) was added dropwise to a suspension of magnesium turnings (614 mg, 25.3 mmol) in Et$_2$O (15 ml). A crystal of iodine was added and the mixture gently warmed to initiate the reaction. The dark brown solution was then added dropwise via a syringe to a suspension of copper bromide-dimethyl sulphide complex (2.48 g, 12.24 mmol) in THF (30 ml) at −40° C. The red-brown suspension was allowed to warm to −20° C. over 0.5h then re-cooled to −40° C. and treated with a solution of Intermediate 13 (3.00 g, 8.16 mmol) in THF (15 ml) over 5 min. The reaction mixture was allowed to warm to RT over 2 h, stirred overnight at RT, then heated at 40° C. for 3 h. The reaction mixture was quenched with NH$_4$Cl solution (20 ml), concentrated in vacuo and the residue partitioned between EtOAc (50 ml) and water (25 ml). The mixture was filtered through Celite® and the organic layer was separated, washed with aqueous NH$_4$OH (10%; 25 ml), and brine (25 ml), dried (MgSO$_4$), and concentrated in vacuo to give a red-brown oily residue which was subjected to chromatography (SiO$_2$; Et$_2$O-hexane) to afford the title compound (ca 1:1) (2.05 g) as a pale yellow gum; δH (CDCl$_3$) 1.10–1.15 (3H, m, CO$_2$CH$_2$Me), 1.5–2.0 (8H, br m, (CH$_2$)$_4$), 3.73, 3.84 (3H, s, OMe), 3.9–4.15 (2H, M, CO$_2$CH$_2$Me), 4.40 (1H, d, J 8.0 Hz, CHCHCO$_2$Et), 4.58, 4.80 (1H; br m, OCH), 4.6– 4.75 (1H, m, CHCHCO$_2$Et), 6.5–6.7, 6.8–7.05 (3H, m, C$_6$H$_3$), 7.1.–7.7 (6H, m, C$_6$H$_4$+ pyridine H$_3$, H$_5$), and 8.48 (2H, br s, pyridine H$_2$H$_6$).

INTERMEDIATE 26

(E) and (Z) isomers of 4-[2-(4-Aminophenyl)-2.-(3-cyclopentyloxy-4-methoxyphenyl)ethenyl]pyridine Water (15 ml) and trifluoroacetic acid (10 ml) were added to Intermediate 13 (6.1 g) in CH$_2$Cl$_2$ (15 ml) at 0° C. and the mixture allowed to warm to RT. After 6 h, the reaction mixture was concentrated in vacuo and the residue partitioned between 10% hydrochloric acid (50 ml) and EtOAc (50 ml). The aqueous layer was separated, basified to pH 14 with 20% sodium hydroxide solution, and extracted with CH$_2$Cl$_2$ (3×50 ml). The extract was dried (MgSO$_4$) and concentrated in vacuo to give the crude title compound (4.2 g). A portion (0.40 g) was subjected to chromatography (SiO$_2$); EtOAc) to afford the title compound (0.29 g); δH (CDCl$_3$) 1.45–2.0 (8H, br m, (CH$_2$)$_4$), 3.80 (2H, br s, NH$_2$), 3.87, 3.90 (3H, s, OMe), 4.58, 4.70 (1H, br m, OCH), 6.6–7.2 (10H, CH$_6$H$_4$+C$_6$H$_3$+pyridine H$_3$, H$_5$+C=CH), and 8.3–8.4 (2H, m, pyridine H$_2$,H$_6$); m/z (ESI) 388 (M$^+$+1, 100%).

INTERMEDIATE 27

(4-Bromophenyl)(3-cyclopentyloxy-4-methoxyphenyl)ketone

A solution of Intermediate 4 (8.00 g, 29.5 mmol) in THF (50 ml) at −70° C. was treated with n-BuLi (19.4 ml, 31.0 mmol, 1.6M solution in hexanes). The slightly yellow solution was stirred at −70° C. for 0 5h then a solution of 4-bromobenzaldehyde (5.46 g, 29.5 mmol) in THF (50 ml) was added via cannula. The reaction was allowed to warm to RT over 2h then quenched with water (25 ml) and extracted with Et$_2$O (2×50 ml). The extract was dried (MgSO$_4$) and concentrated in vacuo to give a pale yellow oil which was dissolved in CH$_2$Cl$_2$ (150 ml) and treated with manganese dioxide (19.24 g, 0.22 mol). The mixture was stirred vigorously for 20h at RT then filtered through Celite® and the residue washed with CH$_2$Cl$_2$ (5×50 ml). The filtrate was concentrated in vacuo to give an off-white solid which was triturated with hexane to give the title compound (7.50 g) as a white solid; δH (CDCl$_3$) 1.55–2.05 (8H, m., (CH$_2$)$_4$), 3.92 (3H, s, OMe), 4.83 (1H, m, OCH), 6.89 (1H, d, J 8.4Hz, ArH ortho to OMe), 7.33 (1H, dd, J 8.4, 2.0Hz, ArH para to OMe), 7.42 (1H, d, J 2.0Hz, ArH ortho to cyclopentyloxy), and 7.55–7.7 (4H, m, C$_6$H$_4$); vmax. (CDCl$_3$) 2248, 1652, 1590, and 1270 cm$^{-1}$; m/z (ESI) 399 (M$^+$+2+Na, 100%), 397 (M$^+$+Na, 90), 296 (16), and 236 (10).

INTERMEDIATE 28 a) (E) and (Z) isomers of 4-[2-(4-Bromophenyl)-2-(3-cyclopentyloxy-4-methoxyphenyl)-ethenyl]pyridine A solution of the compound of Example 1d (7.52 g, 16.0 mmol) and triethylamine (4.05 g, 5.60 ml, 40.0 mmol) in CH$_2$Cl$_2$ (100 ml) was cooled to 0° C. and trifluoroacetic anhydride (3.70 g, 2.50 ml, 17.6 mmol) was added dropwise. The orange-red solution was allowed to warm to RT over 20h then water (25 ml) was added. The mixture was extracted with CH$_2$Cl$_2$ and the extract was dried (MgSO$_4$), concentrated in vacuo and subjected to chromatography to give the title compound (4.73 g) as a white amorphous powder. (Found: C, 66.66; H, 5.27; N, 2.99. C$_{25}$H$_{24}$BrNO$_2$ requires C, 66.67; H, 5.37; N, 3.11%); δH (CDCl$_3$) 1.45–1.95 (8H, br, m, (CH$_2$)$_4$), 3.86, 3.88 (3H, s OMe), 4.55, 4.70 (1H, br m, OCH), 6.6–6.95 (6H, m, C$_6$H$_3$+pyridine H$_3$,H$_5$+C=CH), 7.06, 7.21 (2H, d, J 8.4Hz, ArH of C$_6$H$_4$), 7.4–7.5 (2H, m, ArH of CH$_6$H$_4$), and 8.36 (2H, ca d, J 6.0Hz, pyridine H$_2$, H$_6$) ($^1$H nmr indicates a 1:1 E/Z mixture); v$_{max}$ (CDCl$_3$) 1597, 1514, and 1251 cm$^{-1}$; m/z (ESI) 452 (M$^+$+ 2+Na, 100%), 450 (M$^+$+Na, 88), 384 (30) and 382 (28).

The following intermediates were prepared in a manner similar to Intermediate 28a.

b) (E) and (Z) isomers of 4-{2-(3-Cyclopentyloxy-4-methoxyphenyl)-2-[4-(4,4-dimethyl-2-oxazolinyl)phenyl]ethenyl}pyridine From the alcohol of Example 1e (4.75 g, 9.8 mmol), trifluoroacetic anhydride (2.47 g, 1.66 ml, 11.8 mmol) and triethylamine (0.99 g, 1.36 ml, 11.8 mmol). A portion of the residue (100 mg) was subjected to chromatography (SiO$_2$; EtOAc) to give the title compound (68 mg) as a yellow foam. δH (CDCl$_3$) 1.39, 1.41 (6H, s, CMe$_2$), 1.5–1.95 (8H, m, CH$_2$)$_4$, 3.85, 3.88 (3H, s, OMe), 4.11, 4.14 (2H, s, oxazoline CH$_2$), 4.55, 4.69 (1H, m, OCH), 6.6–6.7 (1H, m, ArH), 6.8–6.85 (3H, m, ArH), 6.91 (1H, d, J 6.2 Hz, pyridine H$_3$, H$_5$), 7.23, 7.38 (2H, d, J 8.2Hz, ArH), 7.9–8.0 (2H, m, ArH), and 8.3–8.45 (2H, m, pyridine H$_2$, H$_6$); ν$_{max}$ (CDCl$_3$) 1735, 1646, 1597 and 1318 cm$^{-1}$; m/z (ESI) 469 (M+, 100%).

c) (Z)-4-[2-(3-Cyclopentyloxy-4-methoxyphenyl)-2-(2-furyl)ethenyl]pyridine

From the compound of Example 34 (1.0 g, 2.64 mmol) in CH$_2$Cl$_2$ (30 ml), triethylamine (0.4 g, 0.55 ml, 3.96 mmol) and trifluoroacetic anhydride (0.61 g, 0.41 ml, 2.91 mmol). Work up [includes treatment with 10% NaOH solution (25 ml)] and chromatography (SiO$_2$; EtOAc/hexane, 7:3) afforded the title compound (0.78 g) as a pale pink solid m.p. 122°–123° C.; (Found: C, 76.37; H, 6.46; N, 3.85. C$_{23}$H$_{43}$NO$_3$ requires C, 76.43; H, 6.41; N, 3.88%); δH (CDCl$_3$) 1.45–1.9 (8H, br m, (CHH$^2$)$_4$), 3.90 (3H, s, OMe), 4.65 (1H, br m, OCH), 6.07 (1H, d, J 3.3 Hz, furan H$_3$), 6.41 (1H, dd, J 3.3, 1.8 Hz, furan H$_4$), 6.75–6.9 (5H, m, C$_6$H$_3$+ pyridine H$_3$, H$_5$), 7.03 (1H, s, C=CH), 7.49 (1H, d, J 1.6Hz, furan H$_5$), and 8.33 (2H, ca. d, J 4.6Hz, pyridine H$_2$, H$_6$); m/z (ESI) 362 (M$^+$+1, 100%), 294 (45).

INTERMEDIATE 29

[4-(4,4-dimethyl-2-oxazolinyl) phenyl-3'-cyclopentyloxy-4'-methoxyphenyl)ketone

A solution of 2-(4-bromophenyl)-4,4-dimethyloxazoline (A. J. Meyers., D. L. Temple, D. Haidukewych and E. D. Milhelich, *J. Org. Chem.*, 22, 2787 (1974) (53.25 g, 0.21 mol) in THF (200 ml) was added dropwise to magnesium turnings (6.0 g, 0.25g atoms). The reaction was stirred for 2h at RT, then a solution of Intermediate 1 (46.0 g, 0.21 mol) in THF (200 ml) was added dropwise. The reaction was stirred for 16h then heated to reflux for i h, cooled to RT and quenched with NH$_4$Cl solution (200 ml). The layers were separated and the aqueous layer extracted with EtOAc (2×250 ml). The organic layer was washed with brine (250 ml), dried (MgSO$_4$), then concentrated in vacuo to give an orange oil. The crude oil was dissolved in CH$_2$Cl$_2$ (350 ml) and treated with manganese dioxide (137 g, 1.58 mol) then stirred vigorously for 72 h. The mixture was filtered through Celite® and the residue washed with CH$_2$Cl$_2$ (300 ml). The filtrate was concentrated in vacuo and the residue triturated with Et$_2$O to give the rifle compound (59.4 g) as an off white amorphous powder m.p. 159° C. δH (CDCl$_3$) 1.41 (6H, s, CMe$_2$), 1.5–2.1 (8H, m, (CH$_2$)$_4$), 3.92 (3H, s, OMe), 4.15 (2H, s, oxazoline CH$_2$,), 4.84 (1H, m, OCH), 6.89 (1H, d, J 8.4HZ, ArH ortho to OMe), 7.35 (1H, dd, J 2.0, 8.4Hz, ArH para to OMe), 7.43 (1H, d, J 2.0Hz, ArH ortho to cyclopentyloxy), 7.78 (2H, d, J 8.5 Hz, ArH), and 8.03 (2H, d, J 8.5Hz, ArH); ν$_{max}$ (CDCl$_3$) 1648 and 1271 cm$^{-1}$; m/z (ESI) 394 (M$^+$+1, 100%).

INTERMEDIATE 30

(E) and (Z) isomers of 4-[1-(3-Cyclopentyloxy-4-methoxyphenyl)-2-(4-pyridyl)ethenyl]benzoic acid hydrochloride A solution of intermediate 28b (4.25 g, 8.8 mmol) in 10% aqueous HCl (15 ml) was heated to reflux for 20 min. Aqueous NaOH solution (5M; 20 ml) and EtOH (15 ml) were then added and heating continued for a further 2 h. The reaction was cooled to RT and acidified to pH 1 with 10% aqueous HCl. The mixture was extracted with CHCl$_3$ (10× 100 ml), the organic extract was dried (MgSO$_4$) and concentrated in vacuo to give the title compound (2.83 g) as a yellow solid; δH (d$_4$-MeOH) 1.45–1.8 (8H, m, (CH$_2$)$_4$), 3.86, 3.88 (3H, s, OMe), 4.66, 4.74 (1H, br m, OCH), 6.65–7.65 (8H, m, C=CH+C$_6$H$_3$+pyridine H$_3$, H$_5$+ArH meta to CO$_2$H), 8.05, 8.13 (2H, d, J ca. 8Hz, ArH ortho to CO$_2$H), and 8.46, 8.55 (2H, d, J ca. 6Hz, pyridine H$_2$, H$_6$) (N.B. CO$_2$H and HCl not observed); ν$_{max}$ (Nujol) 1710, and 1633 cm$^{-1}$; m/z (ESI) 416 (M$^+$+1, 100%).

INTERMEDIATE 31

Ethyl 3-(3-Cyclopentyloxy-4-methoxyphenyl)-3-phenyl-2-(4-pyridyl)propanoate

Phenyl magnesium bromide (3M in THF) (2.3 ml, 6.8 mmol) was added to a slurry of copper (I) chloride (54 mg, 0.55 mmol) in THF (20 ml) at −70° C. The yellow turbid solution was stirred at −78° C. for 0.25 h, then Intermediate 13 (1.00 g, 2.7 mmol) in THF (10 ml) was added via cannula. The reaction was stirred for 2h whilst allowing to warm to RT. The mixture was quenched with saturated NH$_4$Cl solution (5 ml) and water (20 ml) then extracted with EtOAc (2×20 ml). The extract was dried (MgSO$_4$), and concentrated in vacuo to give a yellow oil which was subjected to chromatography (SiO$_2$; EtOAc/hexane, 1:1) to give the title compound (0.29 g) as a white solid m.p. 165°–166° C. (Found: C, 75.48; H, 7.01; N, 3.14. C$_{28}$H$_{31}$NO$_4$ requires C, 75.76; H, 7.00; N, 3.14%); δH (CDCl$_3$) 1.03 (3H, t, J 7.1Hz, COCH$_2$Me), 1.5–2.0 (8H, br m, (CH$_2$)$_4$), 3.80 (3H, s, OMe), 3.9–4.0 (2H, complex m, COCH$_2$CH$_3$), 4.35 (1H, d, J 12.3 Hz, CHCH), 4.57 (1H, d, I 12.3Hz, CHCH), 4.78 (1H, m, OCH), 6.75–7.1 (8H, m, aromatic C$_6$H$_5$+C$_6$H$_3$), 7.22 (2H, dd, J 4.6, 1.6Hz pyridine H$_3$, H$_5$), and 8.41 (2H, dd, J 4.6, 1.6Hz, pyridine H$_2$,H$_6$). ν$_{max}$ (CDCl$_3$) 1734, 1602, and 1516 cm$^{-1}$; m/z (ESI) 468 (M$^+$+Na, 20%), 446 (M$^+$+1, 20%), 282 (22), 281 (100), and 213 (12).

INTERMEDIATE 32

(E) and (Z) isomers of t-Butyl N-{4-[1-(3-cyclopentyloxy-4-methoxyphenyl)-2-(4-pyridyl)ethenyl] phenyl}carbamate A mixture of diphenyl phosphoryl azide (0.6 1 g, 0.48 ml, 2.2 mmol), Intermediate 29 (1.00 g, 2.2 mmol), triethylamine (0.49, 0.68 ml, 4.9 mmol) and t-butanol (25 ml) was heated to reflux for 20 h. The mixture was concentrated in vacuo and the resulting brown oil partitioned between CH$_2$Cl$_2$ (30 ml) and 5% citric acid solution (30 ml). The organic layer was separated, washed with water (20 ml), NaHCO$_3$ solution (20 ml), and brine (20 ml), then dried (MgSO$_4$) and concentrated in vacuo to give a red oil which was subjected to chromatography (SiO$_2$; 5% MeOH/ CH$_2$Cl$_2$) to give the title compound (0.60 g) as a yellow foamy solid. δH (CDCl$_3$) 1.52, 1.54 (9H, s, CMe$_3$), 1.65–1.9 (8H, br m, (CH$_2$)$_4$), 3.86, 3.89 (3H, s, OMe), 4.56, 4.70 (1H, m, OCH), 6.6–7.4 (11H, m, ArH+C=CH+NCO), and 8.34 (2H, d, J 5.2Hz, pyridine H$_2$, H$_6$). ($^1$H nmr indicates ca. 1:1 mixture of isomers); ν$_{max}$ (CHCl$_3$)3441, 1730, 1596, 1518 and 1157 cm$^{-1}$; m/z (ESI) 487 (M$^+$+1, 75%), 472 (12), and 431 (100).

INTERMEDIATE 33

(S*,R*) and (S*,S*) Ethyl 3-(3-Cyclopentyloxy-4-methoxyphenyl)-2-(4-pyridyl)-3-(thienyl)propanate A solution of 2-bromothiophene (0.49 g, 3.0 mmol) in Et$_2$O (5 ml) was added to Mg (0.08 g, 3.3 mmol) in Et$_2$O (2 ml) at RT. The mixture was stirred at RT for 0.3h then heated to reflux for 0.25h before adding a solution of Intermediate 13 (1.0 g, 2.72 mmol) in Et$_2$O-toluene (2:1; 15 ml) dropwise over 10 min at RT. The reaction mixture was stirred at RT for 18 h then quenched with 10% NH$_4$Cl solution (60 ml) and extracted with EtOAc (3×50 ml). The extract was washed with brine (80 ml), dried (MgSO$_4$), and concentrated in vacuo. The residual brown oil was subjected to chromatography (SiO$_2$; Et$_2$O/hexane, 9:1 to Et$_2$O) to afford (i) Intermediate 13 (205 mg); and (ii) title compound (132 mg) after recrystallisation from Et$_2$O-hexane, 1:1) as a white solid m.p. 124°–126° C.; δH (CDCl$_3$) 0.99 (3H, t, J 7.1Hz, OCH$_2$Me), 1.55–2.0 (8H, br m, (CH$_2$)$_4$), 3.82 (3H, s, OMe), 3.85–4.05 (2H, m, OCH$_2$Me), 4.26 (1H, d, J 11.9 Hz, CHCHCO$_2$Et), 4.81 (1H, d, J 11.9 Hz, CHCHCO$_2$Et), 4.85 (1H, br m, OCH), 6.51 (1H, d, J 3.5 Hz, thiophene H$_3$), 6.69 (1H, dd, J 5.1, 3.5 Hz, thiophene H$_4$), 6.81 (1H, d, J 8.8 Hz, ArH ortho to OMe), 6.95–7.0 (3H, m, thiophene H$_5$+2×ArH to OMe), 7.30 (2H, ca d, J 4.6Hz, pyridine H$_3$, H$_5$), and 8.48 (2H, ca. d, J 4.6Hz, pyridine H$_2$, H$_6$); m/z (ESI) 474 (M$^+$+Na, 28%), 452 (M$^+$+1, 12), 368 (25), 289 (12), 288 (38), 287 (100), and 219 (22).

EXAMPLE 1 a) (±)-4-[2-(3-Cyclopentyloxy-4-methoxyphenyl)-2-hydroxy-2-phenylethyl]pyridine n-BuLi (1.4M in hexanes; 2.7 ml, 3.7 mmol) was added dropwise at −70° C. to a solution of 4-methylpyridine (0.35 g, 3.72 mmol) in THF (20 ml). After 0.5 h, a solution of Intermediate 2 (1.00 g, 3.38 mmol) in THF (4 ml) was added over 5 min at −70° C., the mixture stirred for 1 h at this temperature then allowed to warm to RT over 2 h. The reaction mixture was partitioned between Et$_2$O (50 ml) and water (50 ml) and the organic layer was separated. The aqueous layer was further extracted with Et$_2$O (2×40 ml) and the combined organic extract was dried (MgSO$_4$) and concentrated in vacuo. The residue was subjected to chromatography (SiO$_2$; EtOAc/hexane) to afford, first, Intermediate 2 (300mg) then the title compound (738 mg) as a white solid. m.p. 148°–149° C. (toluene-hexane) (Found: C, 77.32; H, 7.04; N, 3.50. C$_{25}$H$_{27}$O$_3$ requires C, 77.09; H, 6.99; N, 3.60%); δH (CDCl$_3$) 1.4–1.9 (8H, br, m, (CH$_2$)$_4$), 2.3 (1H, OH exchanges with D$_2$O), 3.51 (2H, s, CH$_2$ pyridine), 3.78 (3H, s, OMe), 4.60 (1H, br, m, OCHCH$_2$), 6.65–6.9 (5H, m) and 7.15–7.4 (5H, m) (ArH ortho to OMe+2×ArH meta to OMe+CH$_6$H$_5$+pyridine H$_3$,H$_5$), and 8.22 (2H, dm, J 4.5Hz, pyridine H$_2$, H$_6$); m/z 389 (M$^+$3%), 298 (15), 297 (69), 229 (27), 228 (37), 151 (43), 105 (100), 93 (52), 77 (24), and 41 (14).

The following compounds were prepared in a manner similar to the compound of Example 1a.

b) (±)-2-[2-(3-Cyclopentyloxy-4-methoxyphenyl)-2-hydroxy-2-phenylethyl]pyrazine

From 2-methylpyrazine (1.0 ml, 110 mmol) and Intermediate 2 (3.24 g, 11.0 mmol). Trituration with Et$_2$O gave the title compound (0.885 g) as a white solid. δH (CDCl$_3$) 1.45–1.9 (8H, br, m, (CH$_2$)$_4$), 3.73 (2H, s, CH$_2$, pyrazine), 3.80 (3H, s, OMe), 4.68 (1H, br, m, OCH), 6.22 (1H, br s, OH), 6.73 (1H, d, J 8.4Hz, ArH ortho to OMe), 6.89 (1H, dd, J 8.4, 2.0 Hz, ArH para to cyclopentyloxy), 7.0 (1H, d, J 2.0 Hz, ArH ortho to cyclopentyloxy, 7.1–7.5 (5H, m, C$_6$H$_5$), and 8.37 (3H, s, pyrazine H$_3$, H$_5$ H$_6$).

c) (±)-4-[2-(3-Cyclopentyloxy-4-methoxyphenyl)-2-hydroxy-phenylethyl]-3,5-dichloropyridine From Intermediate 15 (2.0 g, 12.3 mmol) and Intermediate 2 (3.65 g, 12.3 mmol). Purification by column chromatography (SiO$_2$; 0–2% MeOH/CH$_2$Cl$_2$) afforded the title compound (1.74 g) as a white solid. m.p. 129°–130° C. δH (CDCl$_3$) 1.5–1.9 (8H, br, m, (CH$_2$)$_4$), 2.65 (1H, br s, OH, 3.85 (3H, s, OMe), 3.92 (1H, d, J 14Hz, CH$_A$H$_B$ pyridine), 3.98 (1H, d, J 14 Hz, CH$_A$H$_B$ pyridine), 4.57 (1H, br, m, OCH), 6.7–6.9 (3H, m, ArH ortho+2×ArH meta to OMe), 7.2–7.4 (5H, m, C$_6$H$_5$), and 8.36 (2H, s, pyridine H$_2$, H$_6$).

d) ±-4-[2-(4-Bromophenyl)-2-(3-cyclopentyloxy-4-methoxyphenyl)-2-hydroxyethyl]pyridine From 4-picoline (2.0 ml, 1.90 g, 20.4 mmol) and Intermediate 26 (7.30 g, 19.5 mmol). Purification by column chromatography (SiO$_2$; gradient elution 50–75%, EtOAc/hexane) gave the title compound (7.77 g) as a pale yellow foamy solid. Found: C, 63.82; H, 5.58; N, 2.96. C$_{25}$H$_{26}$BrNO$_3$ requires C, 64.11; H, 5.60; N, 2.99%. δH (CDCl$_3$) 1.5–1.9 (8H, br, m, CH$_2$)$_4$), 2.7 (1H, br s, OH), 3.46 (1H, d, J 13.1 Hz, CH$_A$H$_B$ pyridine), 3.54 (1H, d, J 13.1 Hz, CH$_A$H$_B$ pyridine), 3.82 (3H, s, OMe), 4.64 (1H, br m, OCH), 6.75–6.9 (5H, m, C$_6$H$_3$+pyridine H$_3$, H$_5$), 7.21 (2H, ca. d, J 8.7Hz, ArH of C$_6$H$_4$), and 8.29 (2H, ca. d, J 6.0Hz, pyridine H$_2$, H$_5$); ν$_{max}$. (CDCl$_3$) 3604, 1605, 1513, and 1256 cm$^{-1}$; m-/z (ESI) 470 (M$^+$+2, 20%), 468 (M$^+$, 18), 377 (52), 375 (55), 95 (13), and 94 (100).

e) (+)-4-{2-(3-Cyclopentyloxy-4-methoxyphenyl)-2-[4-(4, 4-dimethyl-2-oxazolinyl)phenyl]-2-hydroxyethyl}pyridine From 4-methylpyridine (1.45 g, 1.52 ml, 15.6 mmol) and Intermediate 29 (5.82 g, 14.9 mmol). Trituration with Et$_2$O gave the title compound (6.61 g) as an off-white solid. δH (CDCl$_3$) 1.37 (6H, s, CMe), 1.55–1.8 (8H, m, (CH$_2$)$_4$), 2.7 (1H, br s, OH) 3.56 (2H, br s, CH$_2$ pyridine), 3.82 (3H, s, OMe), 4.10 (2H, s, oxazoline CH$_2$), 4.63 (1H, M, OCH), 6.75–6.9 (5H, m, ArH), 7.37 (2H, d, J 8.6 Hz, pyridine H$_3$, H$_5$), 7.85 (2H, d, J 7.3Hz ArH ortho to oxazoline) and 8.29 (2H, br s, pyridine H$_2$, H$_6$); ν$_{max}$ (CDCl$_3$) 3603, 1649, 1512, and 1257 cm$^{-1}$; m/z (ESI) 487 (M$^+$+1, 100%), and 394 (61).

EXAMPLE 2

(±)-4-[1-(3-Cyclopentyloxy-4-methoxyphenyl)-1-hydroxy-2-(4-pyridyl) ethyl]pyridine n-BuLi (1.45M in hexanes; 5.1 ml, 7.41 mmol) was added dropwise at −70° C. to a solution of 4-methylpyridine (0.69 g, 7.41 mmol) in THF (20 ml). After 0.5h a solution of Intermediate 5 (2.0 g, 6.73 mmol) in THF (10 ml) was added dropwise over 5 min. The reaction mixture was stirred for 0.5 h at −70° C. then at RT for 0.5 h. Water (50 ml) was added and the mixture extracted with EtOAc (3×60 ml). The extract was washed with brine (80 ml), dried (MgSO$_4$), and concentrated. The residue was subjected to chromatography (SiO$_2$; EtOAc to EtOAc/CH$_3$OH, 9:1) to afford the title compound (2.33 g) as a white amorphous solid m.p. 99°–103° C.; δH (CDCl$_3$) 1.5–2.0 (9H, br, m, (CH$_2$)$_4$+OH), 3.49 (2H, d, J 2.3 Hz, CH$_2$ COH), 4.65 (1H, br m, OCHCH$_2$), 6.7–6.9 (5H, m, ArH ortho to OMe+2×ArH meta to OMe+pyridine H$_3$, H$_5$), 7.20 (2H, dd, J 4.6, 1.6 Hz, pyridine H$_3$, H$_5$), 8.22 (2H, dd, J 4.6, 1.6 Hz, pyridine H$_2$, H$_6$) and 8.40 (2H, dd, J. 4.6, 1.6 Hz, pyridine H$_2$, H$_6$); m/z 390 (M$^+$3%), 298 (21), 297 (14), 230 (21), 229 (91), 151 (100), 106 (22), 93 (27), 78 (12), and 41 (23).

EXAMPLE 3 a) (±)-4-[2-(3-Cyclopentyloxy-4-methoxyphenyl)-2-phenylethyl]pyridine

Intermediate 7a (3.0 g, 8.09 mmol) in THF (50 ml) was treated with 10% Pd/C (about 500 mg) and hydrogenated over 38 h at RT. The reaction mixture was filtered through Celite® and the filtrate concentrated in vacuo. The residue was subjected to chromatography (SiO$_2$; EtOAc/hexane 1:1) to afford the title compound (1.87 g) as a clear oil which slowly crystallised on standing (Found: C, 79.87; H, 7.26; N, 3.69. C$_{25}$H$_{27}$NO$_2$ requires C, 80.40; H, 7.29; N, 3.75%); δH (CDCl$_3$) 1.5–2.1 (8H, br, m, (CH$_2$)$_4$), 3.27 (2H, d, J 8.0Hz, CH$_2$, pyridine), 3.75 (3H, s, OMe), 4.12 (1H, t, J 8.0 Hz, PhCHCH$_2$), 4.61 (1H, br m, OCHCH$_2$), 6.5–6.7 (3H, m, ArH ortho to OMe+2×ArH meta to OMe), 6.87 (2H, dm, J 4.5Hz, pyridine H$_3$, H$_5$), 7.05–7.2 (5H, m, C$_6$H$_5$) and 8.32 (2H, dm, J 4.5 Hz, pyridine H$_2$, H$_6$); m/z 373 (M$^+$7%), 281 (38), 214 (16), 213 (100), 181 (10), and 152 (11).

Treatment of the free base (1.08 g, 2.90 mmol) in Et$_2$O (10 ml) with ethereal HCl gave, after decantation, the title compound hydrochloride (1.182 g) as a white solid. $^1$H (CDCl$_3$) 1.5–1.7 (2H, br s, cyclopentyl H), 1.75–1.95 (6H, br s, cyclopentyl H), 3.58 (2H, d, J 7.8Hz, CH$_2$ pyridine), 3.80 (3H, s, OMe), 4.18 (1H, t, J 7.8 Hz, CHCH$_2$pyridine), 4.67 (1H, br m, OCH), 6.67 (2H, br m, ArH), 6.76 (1H, m, ArH), 7.1–7.35 (5H, m, C$_6$H$_5$), 7.45 (2H, d, J 6.5 Hz, pyridine H$_3$, H$_5$) and 8.50 (2H, d, J 6.5 Hz, pyridine H$_2$, H$_6$).

The following compounds were prepared in a similar manner to the compound of Example 3a.

b) (±)-4-[2-(3-Cyclopentyloxy-4-methoxyphenyl)-2-phenylethyl]phenol

From Intermediate 10a (0.46 g, 1.19 mmol) in CH$_3$OH (40 ml). Removal of the solvent in vacuo gave the title compound (0.45 g) as a yellow oil; δH (CDCl$_3$) 1.4–1.9 (8H, br, M, (CH$_2$)$_4$), 3.20–3.23 (2H, m, PhCHCH$_2$), 3.70 (3H, s, OMe), 4.07 (1H, t, J 8.0 Hz, PhCHCH$_2$), 4.64 (1H, br m, OCH), 5.88 (1H, br s, OH), 6.59 (2H, ca. d, J 8.6 Hz, ArH ortho to OH), 6.65–6.75 (3H, m, C$_6$H$_3$), 6.81 (2H, ca. d. J 8.6Hz, ArH meta to OH), and 7.1–7.25 (5H, m, C$_6$H$_5$); m/z (ESI) 411 (M$^+$+Na, 100%), 215 (15), and 197 (50).

c) (±)-4-[2-(3-Cyclopentyloxy-4-methoxylphenyl)-2-phenylethyl]anisole

From Intermediate 10c (0.47 g, 1.18 mmol) in CH$_3$OH/ dioxane (1:1, 50 ml). Removal of the solvent in vacuo gave the title compound (0.45 g) as a colorless oil; δH (CDCl$_3$) 1.5–1.9 (8H, br, m, (CH$_2$)$_4$), 3.24 (2H, ca d, J 8.0Hz, PhCHCH$_2$), 3.68 (3H, s, OMe), 3.74 (3H, s, OMe), 4.09 (1H, t, J 8.0 Hz, PhCHCH$_2$), 4.63 (1H, br m, OCH), 6.65–6.75 (5H, M, C$_6$H$_3$+2×ArH ortho to OMe), 6.89 (2H, ca, J 8.5Hz, 2×ArH meta to OMe), and 7.1–7.25 (5H, m, C$_6$H$_5$); m/z (ESI) 426 (M$^+$+1 +Na, 25%), 425 (M$^+$+Na, 100), 279 (24), 236 (48), 211 (30), 183 (25), 151 (36), 119 (48), 87 (78), and 65 (25).

d) (±)-4-[2-(3-Cyclopentyloxy-4-methoxyphenyl)-2-phenylethyl]acetoxybenzene

From Intermediate 11 (0.14 g, 0.33 mmol) in CH$_3$OH/ dioxane (1:1, 40 ml). Removal of the solvent in vacuo gave the title compound (0.13 g) as a colorless oil; δH (CDCl$_3$) 1.5–1.9 (8H, br, m, (CH$_2$)$_4$), 2.24 (3H, s, COMe), 3.30 (2H, d, J 7.7Hz, PhCHCH$_2$), 3.78 (3H, s, OMe), 4.11 (1H, t, J 7.7 Hz, PhCHCH$_2$), 4.65 (1H, br m, OCH), 6.65–6.8 (3H, M, C$_6$H$_3$), 6.88 (2H, d, J 8.5Hz, 2×ArH of C$_6$H$_4$), 6.98 (2H, d, J 8.5 Hz, 2×ArH of C$_6$H$_4$), and 7.2–7.3 (5H, m, C$_6$H$_5$); m/Z (ESI) 453 (M$^+$+Na, 100%).

e) (±)-2-[2-(3-Cyclopentyloxy-4-methoxyphenyl)-2-phenylethyl]pyrazine

From Intermediate 7b (520 mg) in THF/EtOH (12 ml, 1:5). Purification by column chromatography (SiO$_2$; Et$_2$O) gave the title compound (114 mg) as a white solid. m.p. 71.5°–72° C. δH (CDCl$_3$) 1.4–1.9 (8H, br, m, (CH$_2$)$_4$), 3.50 (2H, d, J 8.0 Hz, CH$_2$CH), 3.78 (3H, s,.OMe), 4.51 (1H, t, J 8.0 Hz, CHCH$_2$), (1H, br m, OCH), 6.7–6.75 (3H, m, ArH ortho to OMe+2×ArH meta to OMe), 7.15–7.3 (5H, m, C$_6$H$_5$H), 8.17 (1H, d, J 1.5Hz, pyrazine H$_2$), 8.31 (1H, d, J 2.5Hz, pyrazine H$_5$(1H, m, pyrazine H$_6$).

f) (+)-3-[2-(3-Cyclopentyloxy-4-methoxyphenyl)-2-phenylethyl]-2-methoxypyrazine

From Intermediate 7c (2.67 g, 6.6 mmol) in THF/EtOH (21 ml, 1:20). Purification by column chromatography (SiO$_2$; CH$_2$Cl$_2$) furnished the title compound (2.55 g) as a colorless oil; δH (CDCl$_3$) 1.5–1.9 (8H, br m (CH$_2$)$_4$), 3.42–3.60 (2H, m, CHCH$_2$), 3.77 (3H, s, OMe), 3.89 (3H, s, OMe), 4.67 (1H, t, J 8.0 Hz, CHCH$_2$), 4.67 (1H, br m, OCH), 6.7–6.8 (3H, m, ArH orth to OMe+2×ArH meta to OMe), 7.1–7.3 (5H, m, C$_6$-H$_5$), 7.85 (1H, d, J 2.5 Hz, pyrazine H), and 7.96 (1H, d, J 2.5 Hz, pyrazine H).

g) (±) Methyl 4-[2-(3-Cyclopentyloxy-4-methoxyphenyl)-2-phenylethyl]benzoate

From Intermediate 10 d (3.00 g, 7.0 mmol) in CH$_3$OH/ THF (1:1, 100 ml) to afford the title compound (2.87 g) as a colorless gum; δH (CDCl$_3$) 1.5–1.9 (8H br, m (CH$_2$)$_4$), 3.34–3.37 (2H, m, PhCHCH$_2$), 3.78 (3H, s, OMe), 3.87 (3H, s, OMe), 4.15 (1H, t, J. 8.0 Hz, PhCHCH$_2$), 4.63 (1H, br m, OCH), 6.65 (1H, dd, J 7.8, 2.0Hz, ArH para to cyclopentyloxy), 6.69 (1H, d, J 2.0Hz, ArH ortho to cyclopentyloxy), 6.73 (1H, d, J 7.8Hz, ArH ortho to OMe), 7.05 (2H, ca. d, J 8.5Hz, 2×ArH meta to CO$_2$Me), 7.15–7.3 (5H, m, C$_6$H$_5$), and 7.83 (2H, ca. d, J 8.5Hz 2×ArH ortho to CO$_2$Me); m/z (ESI) 454 (M$^+$+1+Na, 40%), 453 (M$^+$+Na, 100), 301 (12), 239 (10), and 213 (17).

h) (±) Methyl 3-[2-(3-Cyclopentyloxy-4-methoxyphenyl)-2-phenylethyl]benzoate

From Intermediate 12 (140 mg, 0.33 mmol) in CH$_3$OH/ THF (1:1, 20 ml) to afford the title compound (137 mg) as a colorless gum. δH (CDCl$_3$) 1.5–1.9 (8H, br m, (CH$_2$)$_4$), 3.34–3.37 (2H, m, PhCHCH$_2$), 3.78 (3H, s, OMe), 3.88 (3H, s, OMe), 4.17 (1H, t, J 8.0 Hz, PhCHCH$_5$), 4.64 (1H, br m, OCH), 6.65–6.75 (3H, m, C$_6$H$_3$), 7.1–7.3 (7H, m, C$_6$H$_5$+ 2×ArH meta and para to CO$_2$Me), and 7.75–7.85 (2H, m, 2×ArH ortho to CO$_2$Me); m/z (ESI) 453 (M$^+$+Na, 100%).

i) (±)-3-[2-(3-Cyclopentyloxy-4-methoxyphenyl)-2-phenylethyl]pyridazine

From Intermediate 7e (1.87 g). Purification by chromatography (SiO$_2$; Et$_2$O-EtOAc) afforded the title compound (0.91 g) as a pale yellow oil; δH (CDCl$_3$) 1.5–1.9 (8H, br m, (CH$_2$)$_4$), 3.6–3.7 (2H, m, CHCH$_2$), 3.80 (3H, s, OMe), 4.55 (1H, t, J 8.0Hz, CHCH$_2$), 4.65 (1H, br m, OCH), 6.7–6.8 (3H, m, C$_6$H$_3$), 6.93 (1H, dd, J 8.5, 0.8Hz, pyridazine H$_4$), 7.1–7.3 (6H, m, C$_6$H$_5$+pyridazine H$_5$), and 8.97 (1H, dd, J 5.5, 0.8Hz, pyridazine H$_6$); m/z (ESI) 397 (M$^+$+23, 70%), 375 (M$^+$+1, 72), and 281 (100).

j) (±)-3-[2-(3-Cyclopentyloxy-4-methoxyphenyl)-2-phenylethyl]benzoic acid

From Intermediate 10b (1.75 g, 4.23 mmol) in CH$_3$OH-THF (75 ml, 2:1) to afford the title compound (1.56 g) as a pale orange gum; δH (CDCl$_3$) 1.5–2.0 (8H, br m, (CH$_2$)$_4$), 3.2–3.6 (1H, v.br.s), 3.38 (2H, d, J 8.0 Hz, PhCHCH$_2$), 3.79 (3H, s, OMe), 4.18 (1H, t, J 8.0Hz, PhCHCH$_2$), 4.65 (1H, br m, OCH), and 6.6–8.2 (12H, m, CH$_6$H$_5$+C$_6$H$_4$+C$_6$H$_3$).

k) (±)-2-[2-(3-Cyclopentyloxy-4-methoxyphenyl)-2-phenylethyl]-4-methylpyridine From Intermediate 7f (1.03 g). Purification by chromatography (SiO$_2$; Et$_2$O) afforded the title compound (354 mg) as a colorless oil; δH (CDCl$_3$) 1.5–1.9 (8H, br m, (CH$_2$)$_4$), 2.19 (3H, s, pyridine M0. 3.43 (2H, dd, J 8.2, 1.6Hz, PhCHCH$_2$), 3.78 (3H, s, OMe), 4.55 (1H, t, J 8.2Hz, PhCHCH$_2$), 4.65 (1H, br m, OCH), 6.7–6.75 (4H, m, C$_6$H$_3$+pyridine H$_3$), 6.85–6.9 (1H, m, pyridine H$_5$), 7.1–7.3 (5H, m, C$_6$H$_5$), and 8.38 (1H, ca d, J 5.1Hz, pyridine H$_6$).

l) (±)-4-[2-(3-Cyclopentyloxy-4-methoxyphenyl)-2-phenylethyl]pyrimidine

From Intermediate 7g (1.10 g). Purification by chromatography (SiO$_2$; Et$_2$O) afforded the title compound (299 mg) as a colorless oil which slowly crystallised on standing (Found: C, 76.82; H, 6.85; N, 7.35. C$_{24}$H$_{26}$N$_2$O$_2$ requires C, 76.98; H, 7.00; N, 7.48%); δH (CDCl$_3$) 1.5–2.0 (8H, br m, (CH$_2$)$_4$), 3.45 (2H, d, J 8.0 Hz, CHCH$_2$), 3.78 (3H, s, OMe), 4.52 (1H, t, J 8.0 Hz, CHCH$_2$), 4.65 (1H, br m, OCH), 6.7–6.8 (3H, M, C$_6$H$_3$), 6.89(1H, dd, J 5.1, 1.2Hz, pyrimidine H$_5$), 7.15–7.4 (5H, m, C$_6$H$_5$), 8.44 (1H, d, J 5.1Hz, pyrimidine H$_6$), and 9.11 (1H, d, J 1.2Hz, pyrimidine H$_2$.

EXAMPLE 4

(±)-4-[1-(3-Cyclopentyloxy-4-methoxyphenyl)-2-(4-pyridyl)ethyl]pyridine

A solution of Intermediate 8 (0.20 g, 0.54 mmol) in EtOH (10 ml) containing Et$_3$N (0.5 ml) was hydrogenated over 10% Pd/C (54 mg) for 18 h. The reaction mixture was filtered through Celite® and concentrated in vacuo. The residue was subjected to chromatography (SiO$_2$; EtOAc/CH$_3$OH, 19:1) to afford the title compound (170 mg) as a colorless oil. δH (CDCl$_3$) 1.5–1.9 (8H, br, m, (CH$_2$)$_4$), 3.27 (2H, d, J 8.0 Hz, CH$_2$ pyridine), 3.77 (3H, s, OMe), 4.10 (1H, t, J 8.0 Hz, CH$_2$CH pyridine), 4.62, (1H, br m, OCHCH$_2$), 6.5–6.8 (3H, m, ArH ortho to OMe+2×ArH meta to OMe), 6.88 (2H, dd, J 4.5, 1.5 Hz, pyridine H$_3$, H$_5$), 7.06 (2H, dd, J 4.5, 1.5 Hz, pyridine H$_3$, H$_5$), 8.35 (2H, dd, J 4.5, 1.5 Hz, pyridine H$_2$, H$_6$), and 8.43 (2H, dd, J 4.5, 1.5 Hz, pyridine H$_2$, H$_6$); m/z 374 (M$^+$17%), 306 (32), 282 (12), 215 (16), 214 (100), 154 (11), 129 (14), 93 (12), 57 (15), and 41 (18). Treatment of the title compound with ethereal solution furnished the title compound dihydrochloride. m.p. 230°–233° C. (dec).

EXAMPLE 5 a) (±)-4-[2-(3-(Cyclopentyloxy-4-methoxyphenyl)-2-(4-fluorophenylethyl]pyridine hydrochloride To Intermediate 14 (2.19 g, 4.72 mmol) in EtOH (50 ml) was added NaOH (1.0 g, 25 mmol) in water (20 ml). The reaction mixture was heated to reflux until complete hydrolysis (about 1 h) and the pH adjusted to pH 6 with concentrated hydrochloric acid (about 2 ml). The reaction mixture was then heated to reflux until complete decarboxylation occurred (about 7 h). Upon cooling, the yellow solution was half-concentrated and partitioned between 0.5N NaOH (100 ml) and Et$_2$O (100 ml). The organic layer was washed with brine, dried (MgSO$_4$) and evaporated. The residual yellow tinged gum (1.81 g) was taken up in Et$_2$O (50 ml) and 2.5M hydrochloric acid in EtOH (about 2 ml) was added to pH 2. The solvent was evaporated and the yellow foam obtained redissolved in EtOH (20 ml). Et$_2$O was added until the solution became slightly cloudy and the mixture cooled to 0° C. to give an off-white solid. The mother liquor was decanted off, the solid washed with Et$_2$O and dried in vacuo to give the title compound (1.85 g) as an off-white solid. m.p. 147°–150° C. δH (CD$_3$OD) 1.50–1.90 (8H, m, (CH$_2$)$_4$), 3.70 (2H, d, CH$_2$Ar), 3.75 (3H, s, OCH$_3$), 4.45 (1H, t, CHAr), 4.75, (1H, m, OCHCH$_2$), 6.80 (3H, m, At), 7.05 (2H, m, At) 7.35 (2H, m, At), 7.90 (2H, d, Ar), 8.65 (2H, d, Ar); m/z (ESI) 393 (M$^+$+2, 12%), 392 (M$^+$+1, 38), 300 (29), and 299 (100).

The following compound was prepared in a similar manner to the compound of Example 5a.

b) (+)-4-[2-(3-Cyclopentyloxy-4-methoxyphenyl)-2-(4-trifluoromethylphenyl)ethyl]-pyridine hydrochloride From intermediate 25 (2.05 g, 3.99 mmol) and NaOH (0.80 g, 20 mmol) to afford the free base (1.70 g) as a pale yellow gum; δH (CDCl$_3$) 1.5–1.9 (8H, br m, CH$_2$)$_4$), 3.36 (2H, d, J 7.6, 0.8Hz, CHCH$_2$ pyridine), 3.80 (3H, s, OMe), 4.23 (1H, t, J 7.6Hz, CHCH$_2$ pyridine), 4.67 (1H, br m, OCH), 6.65 (1H, d, J 2.0Hz, ArH ortho to cyclopentyloxy), 6.70 (1H, dd, J 7.8, 2.0Hz, ArH para to OMe), 6.79 (1H, d, J 7.8Hz, ArH ortho to OMe), 6.94 (2H, d, J 5.2Hz, pyridine H$_3$, H$_5$), 7.30 (2H, d, J 8.3Hz, 2×ArH meta to CF$_3$), 7.55 (2H, d, J 8.3Hz, 2×ArH ortho to CF$_3$), and 8.42 (2H, d, J 5.2Hz, pyridine H2, H$_6$); m/z (ESI) 443 (M$^+$+2, 24%) 442 (M$^+$+1,87), 350 (22), 349 (100), 281 (40), and 250 (30).

Treatment of the free base (1.65 g) in Et$_2$O (50 ml) with ethanolic HCl (2.5M), concentration in vacuo and recrystallisation (EtOH-Et$_2$O) afforded the title compound (1.66g as an off-whim solid m.p. 149°–152° C.; δH (d$_4$-MeOH) 1.55–1.95 (8H, br m, (CH$_2$)$_4$), 3.77 (3H, s, OMe), 3.78 (2H, d, J 7.8Hz, CHCH$_2$ pyridine), 4.60 (1H, t, J 7.8Hz, CHCH$_2$ pyridine), 4.75 (1H, br m, OCH), 6.8–6.9 (3H, m, C$_6$H$_3$), 7.5–7.65 (4H, m, C$_6$H$_4$), 7.91 (2H, d, J 5.2Hz pyridine H.3, $H_5$), and 8.68 (2H, d, J 5.2Hz, pyridine $H_2$, $H_6$). (N.B. HCl not observed).

c) (±)-4-[2-(3-Cyclopentyloxy-4-methoxyphenyl)-2-thienylethyl]pyridine hydrochloride From Intermediate 33 (566 mg, 1.25 mmol). Chromatography (SiO$_2$; EtOAc/hexane, 4:1) afforded the title compound free base (350 mg) as a colorless oil; δH (CDCl$_3$) 1.5–2.0 (8H, br m, (CH$_2$)$_4$), 3.25 (1H, dd, J 13.5, ca, 8Hz, CHCH$_A$H$_B$), 3.41 (1H, dd, J 13.5, ca. 7Hz, CHCH$_A$H$_B$), 3.80 (3H, S, OMe), 4.36 (1H, t, J ca. 8, ca. 7 Hz, CHCH$_A$H$_B$), 4.65 (1H, br m, OCH), 6.65–6.85 (4H, m, C$_6$H$_3$+thiophene H$_3$), 6.90 (1H, dd, J 5.1, 3.5Hz thiophene H$_4$), 6.94 (2H, dd, J 4.4, 1.6 Hz, pyridine H$_3$, H$_5$), 7.16 (1H, dd, J 5.1, 1.2Hz, thiophene H$_5$), and 8.40 (2H, dd, J 4.4, 1.6Hz, pyridine H$_2$, H$_6$); m/z (ESI) 381 (M$^+$+2, 13%) 381 (M$^+$+1, 65), 288 (2), and 287 (100).

Treatment of the free base (270 mg) in Et$_2$O (15 ml) with ethanolic HCl (2.5M) afforded the title compound (226 mg) as a pale yellow solid. δH (CDCl$_3$) 1.5–1.9 (8H, br m, (CH$_2$)$_4$), 3.51 (1H, dd, J 13.5, 8.6 Hz, CHCH$_A$H$_B$, 3.64 (1H, dd, J 13.5, 7.2 Hz, CHCH$_A$H$_B$), 3.81 (3H, s, OMe), 4.41 (1H, ca. t, J ca. 7.8Hz, CHCH$_A$H$_B$), 4.72 (1H, br·m, OCH), 6.64 (1H, dd, J 8.2, 2.0Hz, ArH para to OMe), 6.7–6.8 (3H, m, 2×ArH of C$_6$H$_3$+thiophene H$_3$), 6.91 (1H, dd, J 5.1 3.5 Hz, thiophene H$_4$), 7.19 (1H, dd, J 5.1, 1.0Hz, thiophene H$_5$), 7.49 (2H, d, J 6.3 Hz, pyridine H$_3$, H$_5$), and 8.55 (2H, d, J 6.3 Hz, pyridine H$_2$, H$_6$).

EXAMPLE 6

(+)-4-[2-(3-Cyclopentyloxy-4-methoxy)-2-phenylethyl]pyridine-N-oxide

A solution of a compound of Example 16 (i) (264 mg) in peracetic acid (0.5 ml) and CH$_2$Cl$_2$ (50 ml) was stirred at RT for 3 h. Additional peracetic acid (0.5 ml) was added and the mixture stirred overnight then treated with saturated aqueous sodium sulphite for 5 min. The organic phase was separated and combined with further CH$_2$Cl$_2$ extracts (2×30 ml). The extract was washed with aqueous HCl (10%; 30 ml), aqueous NaHCO$_3$ (2×30 ml), brine (30 ml), then dried (MgSO$_4$), and concentrated in vacuo. Purification by column chromatrography (SiO$_2$; 1–5% CH$_3$OH/CH$_2$Cl$_2$) gave a colorless oil which was triturated with Et$_2$O-hexane to afford the title compound (260 mg) as a white solid. m.p. 114°–116° C. δH (CDCl$_3$) 1.5–1.9 (8H, br, m, (CH$_2$)$_4$), 3.29 (2H, d, J 8 Hz, CHCH$_2$), 3.80 (3H, s, OMe), 4.06 (1H, t, J 8 Hz, CHCH$_2$), 4.67, (1H, br m, OCH), 6.65–6.8 (3H, m, ArH ortho to OMe+2×ArH meta to OMe), 6.84 (2H, d, J 7Hz, pyridine H$_3$, H$_5$), 7.1 7.35 (5H, m, C$_6$H$_5$), and 8.00 (2H, d, J 7Hz, pyridine H$_2$, H$_6$). (Optical rotation at 0.153 g/100 ml of EtOH [α]$^{22}$=+43°).

EXAMPLE 7 a) (±)-3-[2-(3-Cyclopentyloxy-4-methoxyphenyl)-2-hydroxy-2-phenylethyl]-2-methoxypyrazine n-BuLi (1.6M in hexanes; 6 ml, 12 mmol) was added dropwise at 4° C. to a solution of N,N-diisopropylamine (1.85 ml, 13 mmol) in THF (40 ml). After 0.5 h, 2-methoxy-3-methylpyrazine (1.28 ml, 11 mmol) was added dropwise at −70° C. and the mixture stirred for 2 h at this temperature. A solution of Intermediate 2 (3.26 g, 11 mmol) in THF (20 ml) was added over 10 min at −70° C. and the mixture stirred for a further 1 h and then allowed to warm to RT. The reaction mixture was partitioned between CH$_2$Cl$_2$ (75 ml) and saturated NaHCO$_3$ (100 ml). The organic layer was separated, combined with further CH$_2$Cl$_2$ extracts (2×75 ml), dried (MgSO$_4$) and concentrated in vacuo. The residue was subjected to chromatography (SiO$_2$; CH$_2$Cl$_2$) to afford the title compound (2.94 g) as a white foam. δH (CDCl$_3$) 1.5–2.0 (8H, br m, (CH$_2$)$_4$), 3.63 (1H, d, J 14 Hz, CHH pyrazine), 3.77 (1H, d, J 14Hz, CH pyrazine), 3.79 (3H, s, OMe ortho to cyclopentyloxy), 3.97 (3H, s, pyrazine OMe), 4.67 (1H, br m, OCH), 6.72 (1H, dd, J 8.4Hz, ArH ortho to OMe), 6.77 (1H, s, OH), 6.91 (1H, dd, J 8.4Hz, 2.0 Hz, ArH para to cyclopentyloxy), 7.00 (1H, d, J 2.0 Hz, ArH ortho to cyclopentyloxy), 7.1–7.5: (5H, m, C$_6$H$_5$), and 7.85–7.95 (2H, m, pyrazine H$_5$, H$_6$).

b) (±)-3-[2-(3-Cyclopentyloxy-4-methoxyphenyl)-2-hydroxy-2-phenylethyl]pyridazine From 3-methylpyridazine, (1.0 ml) and Intermediate 2 (3.98 g). Purification by chromatography (SiO$_2$; EtOH—CH$_2$Cl$_2$) afforded the title compound (4.02 g) as an off-white solid.

c) (±)-2-[2-(3-Cyclopentyloxy-4-methoxyphenyl)-2-hydroxy-2-phenylethyl]-4-methylpyridine From 2,4-dimethylpyridine (1.7 ml, 14.5 mmol) and Intermediate 2 (4.30 g, 14.5 mmol). Purification by chromatography (SiO$_2$; CH$_2$Cl$_2$) afforded the title compound (1.23 g) as a colorless oil (Found: C. 77.07; H, 7.10; N, 3.25. C$_{26}$H$_{29}$NO$_3$ requires C, 77.39; H, 7.24; N, 3.47%); δH (CDCl$_3$) 1.4–1.9 (8H, br m, (CH$_2$)$_4$), 2.25 (3H, s, pyridine Me), 3.60 (2H, s, CH$_2$ pyridine), 3.77 (3H, s, OMe), 4.68 (1H, br m, OCH), 6.72 (1H, d, J 8.5Hz, ArH ortho to OMe), 6.8–6.95 (3H, m, ArH para to cyclopentyloxy+pyridine H$_3$, H$_5$), 7.02 (1H, d, J 2.2Hz, ArH ortho to cyclopentyloxy), 7.1–7.3 (3H, m, meta and para ArH of C$_6$H$_5$), 7.46 (2H, ca. d, J 8.5Hz, ortho ArH of C$_6$H$_5$), and 8.23 (1H, ca. d, J 6 Hz, pyridine H$_6$); m/z (ESI) 404 (M$^+$+1, 72%), 387 (13), and 386 (100).

d) (+)-4-[2-(3-Cyclopentyloxy-4-methoxyphenyl)-2-hydroxy-2-phenylethyl]pyrimidine From 4-methylpyrimidine (1.0 ml) and Intermediate 2 (3.98 g). Purification by chromatography (SiO$_2$;CH$_2$Cl$_2$) afforded the title compound (2.56 g) as a white solid; δH (CDCl$_3$) 1.5–2.0 (8H, br m, (CH$_2$)$_4$), 3.66 (2H, s, CH$_2$ pyrimidine), 3.77 (3H, s, OMe), 4.65 (1H, br m, OCH), 6.58 (1H, s, OH), 6.72 (1H, d, J 8.4Hz, ArH ortho to OMe), 6.85 (1H, dd, J 8.4, 2.2Hz, ArH para to cyclopentyloxy), 6.98 (1H, d, J 2.2Hz, ArH ortho to cyclopentyloxy), 7.07 (1H, d, J 5.2Hz, pyrimidine H$_5$), 7.15–7.45 (5H, m, C$_6$H$_5$), 8.53 (1H, d, J 5.2Hz, pyrimidine H$_6$), and 8.99 (1H, s, pyrimidine H$_2$).

EXAMPLE 8

(±)-2-[2-Cyclopentyloxy-4-methoxyphenyl)-2-phenylethyl-1-methylpyrrole

CH$_3$NH$_2$ (generated front a concentrated aqueous solution of CH$_3$NH2.HCl and KOH) was bubbled into a stirred solution of Intermediate 21 (400 mg) in toluene (20 ml) containing a catalytic amount of CH$_3$NH$_2$.HCl at RT for 0.5 h. Et$_3$N (2 drops) was added and the reaction mixture concentrated in vacuo. The residue was subjected to chromatography (SiO$_2$; 20% Et$_2$O/hexane) to afford the title compound (290 mg) as a colorless oil. δH (CDCl$_3$) 1.5–1.9

(8H, br m, (CH$_2$)$_4$), 3.23 (2H, d, J 7.5Hz, CHCH$_2$CO), 3.28 (3H, s, NMe), 3.79 (3H, s, OMe), 4.19 (1H, t, J 7.5Hz, CHCH$_2$CO), 4.66 (1H, m OCH), 5.74 (1H, m, pyrrole H), 5.97 (1H, app. t, J 3.2 Hz, pyrrole H), 6.44 (1H, app. t, J 2.2 Hz, pyrrole H), 6.67 (1H, d, J 1.5 Hz, ArH ortho to cyclopentyloxy), 6.70 (1H, dd, J 8.1Hz, ArH para to cyclopentyloxy), 6.76 (1H, d, J 8Hz, ArH ortho to OMe), and 7.13–7.30 (5H, m, C$_6$H$_5$).

EXAMPLE 9

(±)-3-[2-(3-Cyclopentyloxy-4-methoxyphenyl)-2-phenylethyl-5-hydroxy-[1H]-pyrazole A solution of Intermediate 22 (503 mg, 1.2 mmol) and hydrazine monohydrate (73 mg, 1.5 mmol) in EtOH (10 ml) was heated to reflux for 1.5 h then cooled in an ice-bath. The crystalline product was filtered off, washed with cold EtOH and dried in vacuo to afford the title compound (3.5 mg) as a white solid. m.p. 189°–190° C. δH (CDCl$_3$) (indicates mixture of enol:keto forms; 2:1) 1.5–1.9 (8H, br m, (CH$_2$)$_4$), 2.85 (⅔H, s, CH$_2$CO; keto), 3.13 (4/3H, d, J 8Hz, PhCHCH$_2$; keto), 3.25 (2/3H, d, J 8Hz, PhCHCH$_2$; enol), 3.80 (3H, s, OMe), 4.12 (2/3H, t, J 8Hz, PhCHCH$_2$; enol), 4.19 (⅓H, t, J 8Hz, PhCHCH$_2$; keto), 4.68 (1H, m, OCH), 5.35 (2/3H, s, HC=COH; enol), 6.65–6.8 (3H, m, C$_6$H$_3$), and 7.15–7.35 (5H, m, C$_6$H$_5$). (N.B. ⅔H for HC=COH; enol and NH for keto and enol forms not observed).

EXAMPLE 10

(±)-2-[2-(3-Cyclopentyloxy-4-methoxyphenyl)-2-phenylethyl]thiophene

A mixture of Intermediate 19 (4.75 mg) and Lawesson's Reagent (2,4-bis(4-methoxyphenyl)-1,3-dithia-2,4-diphosphetane-2,4-disulphide) (760 mg) in toluene (10 ml) was stirred at 85° C. for 1.5 h. The reaction mixture was cooled and filtered. The filtrate was concentrated in vacuo and the residual oil subjected to chromatography (SiO$_2$; 10% Et$_2$O/hexane) to afford the title compound (380 mg) as a colorless oil (Found: C, 76.12; H,6.88. C$_{24}$H$_{26}$O$_2$S requires C, 76.15; H, 6.92%); δH (CDCl$_3$) 1.5–2.0 (8H, br m, (CH$_2$)$_4$), 3.56 (2H, d, J 7.6 Hz, PhCHCH$_2$), 3.81 (3H, s, OMe), 4.21 (1H, t, J 7.6 Hz, PhCHCH$_2$), 4.71 (1H, br m, OCH), 6.63 (1H, dd, J 3.4, 0.9 Hz, thiophene H$_3$), 6.75–6.80 (3H, M, C$_6$H$_3$), 6.82 (1H, dd, J 5.1, 3.4 Hz, thiophene H$_4$), 7.05 (1H, dd, J 5.1, 1.2 Hz, thiophene H$_5$), and 7.15–7.35 (5H, m, C$_6$H$_5$).

EXAMPLE 11

(±)-4-[2-(3-Cyclopentyloxy-4-methoxyphenyl)-2-phenylethyl]benzoic acid monohydrate Aqueous NaOH (10%; 50 ml) was added to the compound of Example 3g (2.7 g, 6.28 mmol) in CH$_3$OH (50 ml) and the mixture heated to reflux for 3 h. CH$_3$OH was removed in vacuo, the remaining aqueous phase adjusted to pH 7 with concentrated hydrochloric acid then extracted with CH$_2$Cl$_2$ (2×100 ml). The extract was dried (Na$_2$SO$_4$) and concentrated in vacuo to afford the title compound (2.41 g) as a white solid. m.p. 187°–188.5° C. (Found: C, 74.44; H,6.40. C$_{27}$H$_{28}$O$_4$. H$_2$O requires C, 74.62; H, 6.96%), δH (CDCl$_3$) 1.2–2.0 (~10H, br m, (CH$_2$)$_4$+H$_2$O), 3.3–3.45 (2H, m, PhCHCH$_2$), 3.78 (3H, s, OMe), 4.16 (1H, t, J 8.0 Hz, PhCHCH$_2$), 4.63 (1H, br m, OCH), 6.62 (1H, d, J 2.0Hz, ArH ortho to cyclopentyloxy), 6.69 (1H, dd, J 8.0, 2.0Hz, ArH para to cyclopentyloxy), 6.74 (1H, d, J 8.0Hz, ArH ortho to OMe), 7.09 (2H, d, J 8.2Hz, 2×ArH meta to CO$_2$H), 7.15–7.3 (5H, m, CH$_6$H$_5$), and 7.90 (2H, d, J 8.2Hz, 2×ArH ortho to CO$_2$H); m/z (ESI) 439 (M$^+$+Na, 100%), 415 (20), 331 (25), 302 (28), 301 (35), and 213 (70).

EXAMPLE 12

(±)-4-[2-(3-Cyclopentyloxy-4-methoxyphenyl)-2-phenylethyl]benzamide

To the compound of Example 11 (210 mg, 0.52 mmol) in CH$_2$Cl$_2$ (10 ml) was added Et$_3$N (58 mg, 0.58 mmol) followed by isobutyl chloroformate (79 mg, 0.58 mmol) at RT and stirred for 0.5 h. Ammonia was bubbled into the mixture for 10 min and stirring continued for a further 0.5 h. The reaction mixture was poured into aqueous NaHCO$_3$ (20 ml) and extracted with CH$_2$Cl$_2$ (2×20 ml). The extract was dried (MgSO$_4$), concentrated in vacuo and the residue subjected to chromatography (SiO$_2$; Et$_2$O)) to afford the title compound (150 mg) as an off-white solid m.p. 73°–75° C. δH (CDCl$_3$) 1.5–1.9 (8H, br m, (CH$_2$)$_4$), 3.35–3.79 (2H, m, PhCHCH$_2$), 3.79 (3H, s, OMe), 4.14 (1H, t, J 8.0Hz, PhCHCH$_2$), 4.65 (1H, br m, OCHD, 5.5–6.0 (2H, v.br. s, CONH$_2$), 6.65 (1H, d, J 2.0Hz, ArH ortho to cyclopentyloxy), 6.68 (1H, dd, J 8.1, 2.0Hz, ArH para to cyclopentyloxy), 6.74 (1H, d, J 8.1Hz ArH ortho to OMe), 7.07 (2H, d, J 8.3Hz, 2×ArH meta to CONH$_2$), 7.15–7.3 (5H, m, C$_6$H$_5$), and 7.62 (2H, d, J 8.3Hz, 2×ArH ortho to CONH$_2$); m/z (ESI) 439 (M$^+$+1+Na, 25%), and 438 (M$^+$+Na, 100).

EXAMPLE 13 a) (±)-tert-Butyl N-{4-[2-(3-Cyclopentyloxy-4-methoxyphenyl)-2-phenylethyl]phenyl}carbamate To the compound of Example 11 (1.5 g, 3.6 mmol) in 2-methylpropan-2-ol (50 ml) was added Et$_3$N (360 mg, 3.6mmol) followed by diphenylphosphoryl azide (990 mg, 3.6 mmol) and the mixture, heated to reflux for 3 h. The cooled reaction mixture was poured into aqueous NaHCO$_3$ (100 ml) and extracted with CH$_2$Cl$_2$ (2×100 ml). The extract was dried (MgSO$_4$), concentrated in vacuo and the residue subjected to chromatography (SiO$_2$; hexane/Et$_2$O, 2:1) to afford the title compound (510 mg) as a white solid. m.p. 123°–123° C.; δH(CDCl$_3$) 1.49, 1.50 (9H, s, (Me)$_3$), 1.5–1.95 (8H, br m, (CH$_2$)$_4$+H$_2$O), 3.25 (2H, d, J 7.5Hz, PhCHCH$_2$), 3.782, 3.790 (3H, s, OMe), 4.10 (1H, t, J 7.5Hz, PhCHCH$_2$), 4.65 (1H, br m, OCH), 6.33 (1H, br s, NH), 6.65–6.75 (3H, m, C$_6$H$_3$), 6.91 (2H, ~d, J 8.4Hz, 2×ArH ortho to NHCOCMe$_3$), and 7.1–7.45 (7H, m, CH$_6$H$_5$+2× ArH meta to NHCO$_2$CMe$_3$). [N.B. CONH conformers observed by $^1$H nmr].

b) (+)-tert-Butyl N-{3-[2-(3-cyclopentyloxy-4-methoxyphenyl)-2-phenylethyl]phenyl}-carbamate From a compound of Example 3j (1.44 g, 3.46 mmol), in 2-methylpropan-2-ol (50 ml), Et$_3$N (0.35 g, 3.46 mmol) and diphenylphosphoryl azide (0.95 g, 3.46 mmol). Purification by chromatography (SiO$_2$; hexane-EtOAc, 4:1) to afford the title compound (0.64 g) as a colorless gum; δH (CDCl$_3$) 1.4–1.9 (8H, br m, (CH$_2$)$_4$), 1.50 (9H, s, (Me)$_3$), 3.28 (2H, ca. d, J 8.0Hz, PhCHCH$_2$), 3.77 (3H, s, OMe), 4.16 (1H, t, J 8.0Hz, PhCHCH$_2$), 4.65 (1H, br m OCH), 6.39 (1H, br s, NH), and 6.6–7.4 (12H, m, C$_6$H5+C$_6$H$_4$+C$_6$H$_3$).

EXAMPLE 14

(±)-4-[2-(3-Cyclopentyloxy-4-methoxyphenyl)-2-phenylethyl]phenyl-N-ethylcarbamate Ethyl isocyanate (71 mg, 1.0 mmol) and a catalytic amount of $Et_3N$ (10 µl) was added to a compound of Example 3b (300mg, 0.8 mmol) in toluene (20 ml) and the mixture heated at 60° C. for 4 h. The reaction mixture was poured into aqueous $NaHCO_3$ (50 ml) and extracted with $CH_2Cl_2$ (2×50 ml). The extract was dried ($MgSO_4$), concentrated in vacuo, and the residue subjected to chromatography ($SiO_2$; $Et_2O$/hexane, 1:1) to afford the title compound (140mg) as a colorless gum; δH ($CDCl_3$) 1.18 (3H, t, J 7.2Hz, $NHCH_2Me$), 1.5–2.0 (8H, br m, $(CH_2)_4$), 3.2–3.35 (2H, m, $NHCH_2Me$), 3.29 (2H, d, J 7.8Hz, $PhCHCH_2$), 3.78 (3H, s, OMe), 4.11 (1H, t, J 7.8Hz, $PhCHCH_2$), 4.65 (1H, br m, OCH), 4.98 (1H, br s, NH), and 6.6–7.3 (12H, m, $C_6H_5+CH_6H_4+C_6H_3$); m/z (ESI) 483 ($M^++1+Na$, 38%), 482 (100), and 186 (23).

EXAMPLE 15

(i) (+)-4-H-(3.-Cyclopentyloxy-4-methoxyphenyl)-2-(4-pyridyl)ethyl]pyridine (ii) (−)-4-[1-(3-Cyclopentyloxy-4-methoxyphenyl)-2-(4-pyridyl)ethyl]pyridine A 60 mg/ml solution of the compound of Example 4 in EtOH was made up and prefiltered through a 45µ filter. The sample soution was injected onto a preparative chiracel OJ preparative column (mobile phase: 90:10, hexane/EtOH; flow rate 6 ml/min) in 0.5 ml aliquots (a column loading of 30 mg). The two enantiomeric peaks were collected with a typical retention time of 50 to 63 min for the first peak and 70 to 105 min for the second peak.

EXAMPLE 16

(i) (+)-4-[2-(3-Cyclopentyloxy-4-methoxyphenyl)-2-phenylethyl]pyridine (ii) (−)-4-[2-(3-Cyclopentyloxy-4-methoxyphenyl)-2-phenylethyl]pyridine The compound of Example 3a (500 mg) was made up to a 100 mg/ml solution in EtOH, filtered through a 45µ filtron. The sample solution was injected onto a preparative chiracel OJ preparative column (mobile phase; 80:20, hexane/EtOH; flow rate 6 ml/min) in 0.9 ml aliquots. The two enantiomeric peaks were collected with a typical retention time of 22 to 32 min for the first peak corresponding to title enantiomer (i) (optical rotation at 0.151 g/100 ml of EtOH $[\alpha]^{22}=+37°$) and 42 to 80 min for the second peak, corresponding to title enantiomer (ii) (optical rotation at 0.151 g/100 ml of EtOH $[\alpha]^{22}=+36°$).

CHIRACEL SEPARATION OF OTHER ENANTIOMERS OF THE INVENTION

The procedures described in Examples 15 and 16 were repeated [flow rate of 0.75 ml/min] with the following compounds, to obtain each enantiomer with the retention time shown:

| Compounds | Mobile Phase (hexane-ethanol) | Peak A (min) | Peak B (min) |
|---|---|---|---|
| Example 1b | 80:20 | 22.21 | 30.96 |
| Example 5a | 80:20 | 10.76 | 13.22 |
| Example 5b | 80:20 | 7.31 | 7.93 |
| Example 1c | 80:20 | 13.96 | 17.44 |
| Example 3e | 80:20 | 17.87 | 30.34 |
| Example 3l | 80:20 | 17.73 | 26.54 |
| Exmple 3i | 80:20 | 17.33 | 25.50 |
| Example 3f | 90:10 | 11.77 | 13.25 |
| Example 3g | 80:20 | 19.30 | 40.32 |
| Example 8 | 80:20 | 13.52 | 15.42 |
| Example 27 | 70:30 | 31.54 | 50.03 |
| Example 11 | 80:20 | 20.00 | 42.00 |
| Example 3k | 80:20 | 6.25 | 7.10 |
| Example 21 | 80:20 | 15.67 | 20.64 |
| Example 25 | 80:20 | 15.47 | 17.90 |
| Example 22 | 80:20 | 8.30 | 11.00 |
| Example 33 | 80:20 | 13.82 | 15.15 |
| Example 31 | 80:20 | 21.87 | 28.84 |

EXAMPLE 17

(±)-4-[2-(3, 4-Dimethoxyphenyl)-2-phenylethyl]pyridine

NaH (60% dispersion in oil) (235 mg, 6.09 mmol) was washed with hexane (2×20 ml). DMF (10 ml) was added followed by Intermediate 23 (500 mg, 1.46 mmol) and the mixture stirred for 0.5 h before adding methyl iodide (210 mg, 3.81 mmol). The reaction mixture was stirred overnight at RT, concentrated in vacuo and the residue subjected to chromatography ($SiO_2$) to afford the title compound as a pale yellow gum. δH ($CDCl_3$) 3.35 (2H, d, J 8.0Hz, $PhCHCH_2$), 3.80 (3H, s, OMe), 3.86 (3H, s, OMMe), 4.20 (1H, t, J 8.0Hz, $PhCHCH_2$), 6.67 (1H, d, J 2.0Hz, ArH ortho to OMe and CH), 6.7–6.8 (2H, m, ArH para to OMe+ArH ortho to OMe and meta to CH), 6.97 (2H, ca d, J ca 5.0Hz, pyridine $H_3$, $H_5$), 7.15–7.35 (5H, m, $C_6H_5H$), and 8.42 (2H, ca d, J ca 5.0Hz, pyridine $H_2$, $H_6$); m/z (ESI) 342 ($M^++Na$, 21%), 320 (30), 228 (40), 227 (100), 213 (12), and 196 (12).

EXAMPLE 18

(±)-2-[2-[(3-Cyclopentyloxy-4-methoxyphenyl)-2-phenylethyl]benzo[d]thiazole

Intermediate 19 (1.26 g, 3.5 mmol) in $CH_2Cl_2$ (6 ml) was added to a stirred solution of 2-aminothiophenol (0.44 g, 3.51 mmol) in $CH_2Cl_2$ (8 ml) and pyridine (2 ml) at −70° C. The reaction mixture was stirred at −70° C. for 20 h, warmed to RT, concentrated in vacuo and the residual brown oil subjected to chromatography ($SiO_2$; EtOAc-hexane, 1:1) to afford the title compound (826 mg) as a pale green oil (Found: C, 75.15; H, 6.31; N, 3.30. $C_{27}H_{27}NO_2S$ requires C, 75.49; H, 6.34; N, 3.26%); SH ($CDCl_3$) 1.5–1.9 (8H, br m, $(CH_2)_4$), 3.78 (3H, s, OMe), 3.83 (2H, ca d, J ca 8Hz, $PhCHCH_2$), 4.60 (1H, t, J 8.0Hz, $PhCHCH_2$), 4.63 (1H, br m, OCH), 6.7–6.85 (3H, m, $C_6H_3$), 7.1–7.45 (7H, m, $C_6H_5$+benzothiazole $H_5$, $H_6$), 7.74 (1H, ca d, J 8Hz, benzothiazole $H_4$ or $H_7$), and 7.95 (1H, ca d, J ca 8Hz, benzothiazole $H_4$ or $H_7$).

EXAMPLE 19

(±)-4-[1-(3-Cyclopentyloxy-4-methoxyphenyl)-2-(4-pyridyl)ethyl]benzaldehyde

NaOH (800 mg, 20 mmol) in water (20 ml) was added to a solution of Intermediate 24 (2.46 g, 4.87 mmol) in EtOH (50 ml) and the mixture heated to reflux for 1.5 h. Concentrated hydrochloric acid was added to pH 4.5 and the mixture heated to reflux for 18 h to complete the decarboxylation. The reaction mixture was concentrated to half-volume and partitioned between NaOH solution (0.5M; 100 ml) and Et$_2$O (100 ml). The organic layer was separated, washed with brine (25 ml), dried (MgSO$_4$), and concentrated in vacuo to afford the title compound (1.80 g) as a pale orange gum; δH (CDCl$_3$) 1.5–2.0 (8H, br m, (CH$_2$)$_4$), 3.35 (2H, ca d, J 7.8Hz, CHCH$_2$ pyridine), 3.80 (3H, s, OMe), 4.25 (1H, t, J 7.8Hz, CHCH$_2$ pyridine), 4.65 (1H, br m, OCH), 6.63 (1H, d, J 1.8Hz, ArH ortho to cyclopentyloxy), 6.70 (1H, dd, J 7.8, 1.8Hz, ArH para to OMe), 6.78(1H, d, J 7.8Hz, ArH ortho to OMe), 6.92 (2H, ca d, J 6.7Hz, pyridine H$_3$, H$_5$), 7.35 (2H, d, J 8.3Hz, 2×ArH meta to CHO), 7.79 (2H, d, J 8.3Hz, 2×ArH ortho to CHO), 8.40 (2H, ca d, J 6.7Hz, pyridine H$_2$, H$_6$) and 9.97 (1H, s, CHO); m/z (ESI) 402 (M$^+$+1, 38%), 310 (22), and 309 (100). Treatment of the title compound (400 mg) in Et$_2$O (40 ml) with ethanolic HCl (2.5M) and concentration in vacuo afforded the title compound hydrochloride (420 mg) as a yellow solid.

EXAMPLE 20

(±)-4-[2-(3-Cyclopentyloxy-4-methoxyphenyl)-2-(4-hydroxymethylphenyl)ethyl]pyridine Sodium borohydride (235 mg, 6.21 mmol) was added portionwise to the compound of Example 19 (1.11 g, 2.85 mmol) in EtOH (35 ml) at −20° C. The suspension was allowed to warm to RT and stirred for 18 h then treated dropwise with glacial acetic acid. The reaction mixture was concentrated in vacuo and the residue partitioned between Et$_2$O (50 ml) and NaOH solution (1M; 50 ml). The organic phase was separated, dried (MgSO$_4$) and concentrated in vacuo to afford the title compound (1.03 g) as a colorless gum; m.p. 179°–182° C.; δH (CDCl$_3$) 1.5–2.0 (8H, br m, (CH$_2$)$_4$), 2.4 (1H, v.br.s, CH$_2$OH), 3.31 (2H, d, J 7.9Hz, CHCH$_2$ pyridine), 3.80 (3H, s, OMe), 4.15 (1H, t, J 7.9 Hz, CHCH$_2$ pyridine), 4.65 (3H, sl.br.s, OCH+CH$_2$OH), 6.6–6.8 (3H, m, C$_6$H$_3$), 6.92 (2H, ca d, J 6.5Hz, pyridine H$_3$, H$_5$), 7.19 (2H, d, J 8.1Hz, 2×ArH of CH$_6$H$_4$), 7.26 (2H, d, J 8.1Hz, 2×ArH of CH$_6$H$_4$), and 8.35 (2H, ca d, J 6.5Hz, pyridine H$_2$,H$_6$); m/z (ESI)$_{404}$ (M$^+$+1, 35%), 312 (30), and 311 (100).

Treatment of the title compound (600 mg) in Et$_2$O (50 ml) with ethanolic HCl (2.5M), concentration in vacuo followed by recrystallisation (EtOH-Et$_2$O) afforded the title compound hydrochloride (602 mg) as a white solid; δH (d$_4$-MeOH) 1.5–2.0 (8H, br m, (CH$_2$)$_4$), 3.72 (2H, d, J 8.1 Hz, CHCH$_2$ pyridine), 3.76 (3H, s, OMe), 4.44 (1H, t, J 8.1 Hz, CHCH$_2$ pyridine), 4.55 (2H, s, CH$_2$OH), 4.74 (1H, br m, OCH), 6.8–6.85 (3H, m, C$_6$H$_3$), 7.25–7.35 (4H, m, C$_6$H$_4$), 7.87 (2H, ca d, J 6.8Hz, pyridine H$_3$, H$_5$), and 8.62 (2H, ca d, J 6.8Hz, pyridine H$_2$, H$_6$) (N.B. CH$_2$OH and HCl not observed).

EXAMPLE 21

(±)-4-[2-(3 Cyclopentyloxy-4-methoxyphenyl)-2-(4-methoxymethylphenyl)ethyl]pyridine The compound of Example 20 (400 mg, 1.02 mmol) in THF (10 ml) was added to a suspension of NaH (60% dispersion in oil) (124 mg, 3.09 mmol) in THF (10 ml) at 0° C. then allowed to warm at RT over 0.5 h. The mixture was cooled to −20° C., treated with a solution of methyl iodide (98.4 μl, 1.58 mmol) in THF (5 ml) and allowed to warm to RT. A further portion of methyl iodide (300 μl, 4.8 mmol) was added and the mixture allowed to stir at RT overnight then concentrated in vacuo. The residue was subjected to chromatography (SiO$_2$; EtOAc-hexane) to afford the title compound (125 mg) as a pale yellow gum; δH (CDCl$_3$) 1.5–2.0 (8H, br m, (CH$_2$)$_4$), 3.29 (2H, d, J 8.3Hz, CHCH$_2$ pyridine), 3.38 (3H, s, CH$_2$OMe), 3.80 (3H, s, OMe), 4.14 (1H, t, J 8.3Hz, CHCH$_2$ pyridine), 4.40 (2H, s, CH$_2$OMe), 4.63 (1H, br m, OCH), 6.6–6.8 (3H, m, C$_6$H$_3$), 6.92 (2H, ca d, J 6.5Hz, pyridine H$_3$, H$_5$), 7.18 (2H, d, J 8.2 Hz, 2×ArH of C$_6$H$_4$), 7.25 (2H, d, J 8.2Hz, 2×ArH of C$_6$H$_4$), and 8.39 (2H, ca d, J 6.5 Hz, pyridine H$_2$, H$_6$); m/z (ESI) 419 (M$^+$+2, 15%), 418 (M$^+$+1, 45), 326 (33), and 325 (100).

Treatment of the title compound (100 mg) in Et$_2$O (25 ml) with ethanolic HCl (2.5M) then concentration in vacuo and recrystallisation (EtOH-Et$_2$O) afforded the title compound hydrochloride (102mg) as an off-white solid m.p. 182°–185° C.; δH (d$_4$-MeOH) 1.5–1.9 (8H, br m, (CH$_2$)$_4$), 3.34 (3H, s, CH$_2$OMe), 3.71 (2H, d, J 8.3Hz, CHCH$_2$ pyridine), 3.75 (3H, s, OMe), 4.39 (2H, s, CH$_2$OMe), 4.43 (1H, t, J 8.3Hz, CHCH$_2$ pyridine), 4.73 (1H, br m, OCH), 6.75–6.85 (3H, m, C$_6$H$_3$), 7.25 (2H, d, J 8.3Hz, 2×ArH of CH$_6$H$_4$), 7.32 (2H, d. J 8.3HZ, 2×ArH of C$_6$H$_4$), 7.84 (2H, ca d, J 6.7Hz, pyridine H$_3$, H$_5$), and 8.61 (2H, ca d, J 6.7Hz, pyridine H$_2$, H$_6$).

EXAMPLE 22

(±)-4-[2-(3-Cyclopentyloxy-4-methoxyphenyl)-2-(4-dimethylaminomethylphenyl)ethyl]pyridine Ethanolic HCl (2.5M) was added dropwise to dimethylamine (3.6 ml of a 14% w/v solution in CH$_3$OH, 11.1 mmol, 7.6 eq) followed by the compound of Example 19 (570 mg, 1.46 mmol) in CH$_3$OH (5 ml) and sodium cyanoborohydride (92 mg, 1.46 mmol) in one portion. The reaction mixture was stirred at RT for 24 h then concentrated in vacuo and partitioned between EtOAc (25 ml) and NaOH solution (2M). The organic layer was separated, dried (K2CO$_3$), and concentrated in vacuo to give a pale brown gum which was subjected to chromatography (SiO$_2$; CH$_3$OH—CH$_2$Cl$_2$, 1:19) to afford the title compound (310mg) as a pale yellow gum; δH (CDCl$_3$; 250MHz) 1.5–2.0 (8H, br m, (CH$_2$)$_4$), 2.21 (6H, s, NMe2), 3.29 (2H, d, J 7.9Hz, CHCH$_2$ pyridine), 3.37 (2H, s, CH$_2$NMe$_2$), 3.79 (3H, s, OMe), 4.13 (1H, t, J 7.9Hz, CHCH$_2$ pyridine), 4.64 (1H, br m, OCH), 6.63 (1H, d, J 1.9Hz, ArH Ortho to cyclopentyloxy), 6.68 (1H, dd, J 8.2, 1.9Hz, ArH para to OMe), 6.74 (1H, d, J 8.2Hz, ArH ortho to OMe), 6.92 (2H, ca d, J 6.0Hz, pyridine H$_3$, H$_5$), 7.13 (2H, d, J 8.2Hz, 2×ArH of C$_6$H$_4$H), 7.24 (2H, d, J 8.2Hz, 2×ArH of C$_6$H$_4$), and 8.37 (2H, ca d, J 6.0Hz, pyridine H$_2$, H$_6$); m/z (ESI) 432 (M$^+$+2, 30%), 431 (M$^+$+1, 100), 338 (31), 294 (16), 226 (16), and 136 (9).

Treatment of the title compound (310 mg) in Et$_2$O (25 ml) with ethanolic HCl (2.5M) and concentration in vacuo afforded the title compound dihydrochloride (360 mg) as a pale yellow solid; δH (d$_4$-MeOH) 1.5–2.0 (8H, br m, (CH$_2$)$_4$), 2.82 (6H, s, CH$_2$NMe$_2$), 3.75 (5H, sl.br.s, OMe+ CHCH$_2$ pyridine), 4.27 (2H, s, CH$_2$NMe$_2$), 4.52 (1H, t, J ca 8.0Hz, CHCH$_2$ pyridine), 4.78 (1H, br m, OCH), 6.8–6.9 (3H, m, C$_6$H$_3$), 7.4–7.6 (4H, m, C$_6$H$_4$H), 7.88 (2H, ca d, J 6.7Hz, pyridine H$_3$, H$_5$), 8.63 (2H, ca d, J 6.7Hz, pyridine H$_2$, H$_6$) (N.B. HCl not observed).

EXAMPLE 23

(±)-4-[1-(3-Cyclopentyloxy-4-methoxyphenyl)-2-(4-pyridyl)ethyl]benzoic acid

Aqueous sodium dihydrogen phosphate (5%; 15 ml), then KMnO$_4$ (2.0 g, 12.7 mmol) in water (20 ml), were added to a solution of the compound of Example 19 (1.50 g, 3.85 mmol) in t-butanol (25 ml) at RT. After 0.25 h, aqueous sodium sulphite solution (20 ml) was added, the reaction mixture filtered through Celite®, the filter pad washed well with NaOH solution (0.5M), and the filtrate concentrated in vacuo. The residue was partitioned between $Et_2O$ (50 ml) and water (50 ml), the aqueous phase separated and acidified to pH 4 with concentrated hydrochloric acid. The mixture was cooled overnight at about 4° C., the precipitate filtered off and washed with water then $Et_2O$ and dried in vacuo to afford the title compound (950 mg, 61%) as a white solid; m.p. 161°–163° C.; $^1H$ ($d_4$-MeOH) 1.5–1.9 (8H, br m, $(CH_2)_4$), 3.42 (2H, d, J 8.0Hz, $CHCH_2$ pyridine), 3.75 (3H, s, OMe), 4.35 (1H, t, J 8.0Hz, $CHCH_2$ pyridine), 4.70 (1H, br m, OCH), 6.7–6.85 (3H, m, $C_6H_3$), 7.18 (2H, d, J 6.7Hz, pyridine $H_3$, $H_5$), 7.38 (2H, d, J 8.3Hz, 2×ArH meta to $CO_2H$), 7.93 (2H, d, J 8.3Hz, 2×ArH ortho to $CO_2H$), and 8.30 (2H, d, J 6.7Hz, pyridine $H_2$, $H_6$) (N.B. $CO_2H$ not observed); m/z (ESI) 419 ($M^++2$, 12%), 418 ($M^++1$, 40), 326 (23) and 325 (100).

Treatment of the title compound (235 mg) in $Et_2O$ (25 ml) with ethanolic HCl (2.5M), concentration in vacuo and recrystallisation (EtOH-$Et_2O$) afforded the title compound hydrochloride (224 mg) as a white solid; δH ($d_4$-MeOH) 1.5–1.9 (8H, br m, $(CH_2)_4$) 3.75 (2H, d, J 8.0Hz, $CHCH_2$ pyridine), 3.75 (3H, s, OMe), 4.52 (1H, t, J 8.0Hz, $CHCH_2$ pyridine), 4.74 (1H, br m, OCH), 6.8–6.9 (3H, m, $C_6H_3$), 7.43 (2H, d, J 8.3Hz, 2×ArH meta to $CO_2H$), 7.80 (2H, d, J 8.3Hz, 2×ArH ortho to $CO_2H$), 7.88 (2H, d, J 6.7Hz, pyridine $H_3$, $H_5$), and 8.62 (2H, d, J 6.7Hz, pyridine $H_2$, $H_6$) (N.B. $CO_2H$ and HCl not observed).

EXAMPLE 24

(±)-4-[1-(3-Cyclopentyloxy-4-methoxyphenyl)-2-(4-pyridyl)ethyl]benzamide

N-Methylmorpholine (163 μL, 1.48 mmol, 1.5 eq) then isobutyl chloroformate (142 μL, 1.09 mmol, 1.1 eq) were added to the compound of Example 23 (400 mg, 1.00 mmol) in THF-DMF (20 ml; 3:1) at −20° C. Concentrated aqueous ammonia solution (1.0 ml) was added, the mixture allowed to warm to RT overnight then concentrated in vacuo. The residue was partitioned between EtOAc (25 ml) and NaOH solution (1M; 20 ml). The organic layer was separated, washed with phosphate buffer (pH 7), dried ($MgSO_4$), and concentrated in vacuo. The residue was subjected to chromatography ($SiO_2$; $CH_3OHCH_2Cl_2$, 1:19) to afford the title compound (245 mg) as a pale yellow gum; m.p. 180°–182° C.; δH ($CDCl_3$; 250MHz) 1.5–2.0 (8H, br m, $(CH_2)_4$), 3.32 (2H, d, J 7.9H $CHCH_2$ pyridine), 3.80 (3H, s, OMe), 4.20 (1H, t, J 7.9Hz, $CHCH_2$ pyridine), 4.64 (1H, br m, OCH), 5.6 (1H, v.br.s. $CONH$), 6.0 (1H, v.br.s. $CONH$), 6.63 (1H, d, J 2Hz, ArH ortho to cyclopentyloxy), 6.68 (1H, dd, J 8.2, 2.0Hz, ArH para to OMe), 6.76 (1H, d, J 8.2Hz, ArH ortho to OMe), 6.92 (2H, ca d, J 6.0Hz, pyridine $H_3$, $H_5$), 7.26 (2H, ca d, J 8.3Hz, 2×ArH meta to $CONH_2$), 7.71 (2H, ca d J 8.3Hz, 2×ArH, 2×ArH ortho to $CONH_2$) and 8.40 (2H, ca d. J 6.0Hz, pyridine $H_2$, $H_6$); m/z (ESI) 418 ($M^++2$, 15%), 417 ($M^++1$, 48), 325 (22), and 324 (100).

Treatment of the title compound (240 mg) in $Et_2O$ (25 ml) with ethanolic HCl (2.5M), concentration in vacuo, and recrystallisation (EtOH-$Et_2O$) afforded the title compound hydrochloride (245 mg) as a white solid; δH ($d_4$-MeOH) 1.5–2.0 (8H, br m, $(CH_2)_4$), 3.75 (2H, d, J 8.2Hz, $CHCH_2$ pyridine), 3.75 (3H, s, OMMe), 4.54 (1H, t, J 8.2Hz, $CHCH_2$ pyridine), 4.76 (1H, br m, OCH), 6.8–6.9 (3H, M, $C_6H_3$), 7.44 (2H, d, J 8.4Hz, 2×ArH meta to $CONH_2$), 7.88 (2H, d, J 6.7Hz, pyridine $H_3$, $H_5$), 7.94 (2H, d, J 8.4Hz, 2×ArH ortho to $CONH_2$), and 8.63 (2H, d, J 6.7Hz, pyridine $H_2$, $H_6$) (N.B. $CONH_2$ and HCl not observed).

EXAMPLE 25

(±)-Ethyl 4-[1-(3-Cyclopentyloxy-4-methoxyphenyl)-2-(4-pyridyl)ethyl]benzoate

Acetyl chloride (500 μL) was added to EtOH (10 ml) followed by the compound of Example 23 (385 mg, 0.95 mmol) and the resulting solution heated to reflux for 18 h. The reaction mixture was concentrated in vacuo and the residue partitioned between aqueous sodium carbonate solution (2M; 10 ml) and $Et_2O$ (25 ml). The organic layer was separated, dried ($MgSO_4$), concentrated in vacuo and the residue subjected to chromatography ($SiO_2$; EtOAc-hexane, 1:1 to 3:2) to afford the title compound (300 mg) as a pale yellow gum; m.p. 170°–173° C.; δH ($CDCl_3$) 1.39 (3H, t, J 7.5 Hz, $COCH_2Me$), 1.5–2.0 (8H, br m, $(CH_2)_4$), 3.32 (2H, d, J 8.0Hz, $CHCH_2$ pyridine), 3.80 (3H, s, OMe), 4.20 (1H, t, J 8.0Hz, $CHCH_2$ pyridine), 4.30 (2H, q, J 7.5Hz, $COCH_2Me$), 4.62 (1H, br m, OC.H), 6.65 (1H, d, J 2.0Hz, ArH ortho to cyclopentyloxy), 6.68 (1H, dd, J 7.8, 2.0Hz, ArH para to OMe), 6.78 (1H, d, J 7.8Hz, ArH ortho to OMe), 6.92 (1H, dd, J 5.2, 0.8Hz, pyridine $H_3$, $H_5$) 7.25 (2H, d, J 8.5Hz, 2×ArH meta to $CO_2Et$), 7.94 (2H, d, J 8.5Hz, 2×ArH ortho to $CO_2Et$), and 8.40 (2H, dd. J 5.2, 0.8Hz, pyridine $H_2$, $H_6$); m/z (ESI) 447 ($M^++2$, 20%), 446 ($M^++1$, 63), 354 (27), 353 (100), and 285 (35).

Treatment of the title compound (295 mg) in $Et_2O$ (25 ml) with ethanolic HCl (2.5M), concentration in vacuo and recrystallisation (EtOH-$Et_2O$) afforded the title compound hydrochloride (300 mg) as an off-white solid; δH ($d_4$-MeOH) 1.36 (3H, t, J 7.2Hz, $COCH_2Me$), 1.5–1.9 (8H, br m, $(CH_2)_4$), 3.73 (2H, d, J 8.2Hz, $CHCH_2$ pyridine), 3.76 (3H, s, OMe), 4.33 (2H, q, J 7.2Hz, $COCH_2Me$), 4.53 (1H, t, J 8.2Hz, $CHCH_2$ pyridine), 4.75 (1H, br m, OCH), 6.8–6.9 (3H, m, $C_6H_3$), 7.45 (2H, d, J 8.4Hz, 2×ArH meta to $CO_2Me$), 7.84 (2H, d, J 6.5Hz, pyridine $H_3$, $H_5$), 7.94 (2H, d, J 8.4Hz, pyridine $H_2$, $H_6$), and 8.61 (2H, d, J 6.5Hz, pyridine $H_2$, $H_6$).

EXAMPLE 26

(±)-2-Chloro-4-[2-(3-cyclopentyloxymethoxyphenyl)-2-phenylethyl]pyridine

A mixture of the compound of Example 6 (2.39 g, 6.16 mmol) and phosphorus oxychloride (25 ml) was heated to reflux overnight. The reaction mixture was cooled to RT then carefully added to saturated potassium carbonate solution (250 ml). Potassium hydroxide (2M) was added to pH 7.5 and the yellow-orange mixture extracted with EtOAc (3×50 ml). The extract was washed with brine (30 ml), dried ($MgSO_4$), and concentrated in vacuo to give a red-brown gum which was subjected to chromatography ($SiO_2$; $Et_2O$-hexane, 1:1) to afford the title compound (1. 16 g, 46%) as a pale yellow gum; δH ($CDCl_3$) 1.5–2.0 (8H, br m, $(CH_2)_4$), 3.30 (2H, d, J 8.0Hz, $PhCHCH_2$), 3.80 (3H, s, OMe), 4.14 (1H, t, J 8.0Hz, $PhCHCH_2$), 4.66 (1H, br m, OCH), 6.68 (1H, d, J 2.0 Hz, ArH ortho to cyclopentyloxy), 6.69 (1H, dd, J 8.0, 2.0 Hz, ArH ortho to OMe), 6.76 (1H, d, J 8.0Hz, ArH ortho to OMe), 6.84 (1H, d, J 6.5Hz, pyridine $H_5$), 7.00 (1H, s, pyridine $H_3$), 7.05–7.3 (5H, m, $C_6H_5$), and 8.17 (1H, d, J 6.5Hz, pyridine H6).

EXAMPLE 27

(±)-3-[2-(3-Cyclopentyloxy-4-methoxyphenyl)-2-phenylethyl]aniline

Sodium iodide (210 mg, 1.4 mmol) and trimethylsilyl chloride (152 mg, 1.4 mmol) was added to the compound of Example 13b (620 mg, 1.27 mmol) in acetonitrile (20 ml) and the mixture stirred at RT for 1 h. The reaction mixture was poured into 10% sodium thiosulphate solution (50 ml) and extracted with $CH_2Cl_2$ (2×50 ml). The extract was dried ($MgSO_4$), concentrated in vacuo and the residue subjected to chromatography ($SiO_2$; $Et_2O$) to afford the title compound (210 mg) as a colorless gum; δH ($CDCl_3$) 1.5–1.9 (8H, br m, $(CH_2)_4$), 3.21 (2H, d, J 7.6Hz, $PhCHCH_2$), 3.44 (2H, br s, $NH_2$), 3.75 (3H, s, OMe), 4.14 (1H, t, J 7.6Hz, $PhCHCH_2$), 4.65 (1H, br m OCH), 6.3–6.45 (3H, m, $C_6H_3$), and 6.6–7.4 (9H, m, $C_6H_5+C_6H_4$); m/z (ESI) 410 ($M^++Na$, 30%), 388 ($M^++1$, 60), 320 (58), 213 (23), and 196 (100).

EXAMPLE 28

(±)-Sodium 3-[2-(3 Cyclopentyloxy-4-methoxyphenyl)-2-phenylethyl]-1, 2, 4-triazolyl-5-thiolate A mixture of thiosemicarbazide (0.43 g, 4.7 mmol) and Intermediate 19 (1.70 g, 4.7 mmol) in toluene (30 ml) was heated to reflux for 4 h. The reaction mixture was cooled, diluted with $Et_2O$ (30 ml) and the precipitate collected by filtration. The precipitate was washed with $Et_2O$ then water to give a white solid, a portion of which (0.41 g) was suspended in aqueous $Na_2CO_3$ (2M; 30 ml) and heated to reflux for 4 h. The cooled reaction mixture was diluted with water (20 ml), acidified with 10% hydrochloric acid to pH 5 and extracted with $CH_2Cl_2$ (2×40 ml). The extract was dried ($MgSO_4$), concentrated in vacuo and the residue recrystallised ($CH_3OH$) to afford the title compound (0.31 g) as a white solid (Found: C, 62.97; H, 5.98; N, 10.02. $C_{22}H_{24}N_3NaO_3S$ requires C, 63.29; H, 5.79; N, 10.07%); $^1H$ (250MHz; $DMSO$-$d_6$) 1.5–2.0 (8H, br m, $(CH_2)_4$), 3.26 (2H, d, J 8.2Hz, $PhCHCH_2$), 3.67 (3H, s, OMe), 4.45 (1H, t, J 8.2Hz, $PhCHCH_2$), 4.72 (1H, br m, OCH), 6.7–6.85 (3H, m, $C_6H_3$), 7.1–7.35 (5H, m, $C_6H_5$), and 13.09 (1H, br s, NH); m/z (ESI) 419 ($M^++1+Na$, 35%), 418 ($M^++Na$, 67), 397 ($M^++1$, 95), 396 (M+, 100), 328 (15), 204 (25), and

EXAMPLE 29

2-[2-(3-Cyclopentyloxy-4-methoxyphenyl-2-phenylethyl]benzimidazole

Intermediate 19 (2.47 g, 6.9 mmol) in THF (10 ml) was added dropwise to a solution of 1,2-diaminobenzene (3.72 g, 34.4 mmol) in THF (40 ml) at 0° C. and the mixture stirred for 2 h. The reaction mixture was concentrated in vacuo and the residue washed with $Et_2O$ (5×50 ml). The extract was washed with 10% hydrochloric acid (50 ml), sodium hydrogen carbonate solution (50 ml), brine (50 ml), then concentrated in vacuo. The residue was subjected to chromatography ($SiO_2$; EtOAc-hexane, 1:1) to give a pale brown glassy solid (1.02 g), a portion of which (0.44 g) was heated neat at 150° C. for 60 h then subjected to chromatography ($SiO_2$; $Et_2O$-hexane 1:1) to afford the title compound (273 mg) as an off-white solid; m.p. 97.5°–98° C.; $δ_H$($CDCl_3$) 1.4–1.9 (8H, br m, $(CH_2)_4$), 3.6–3.7 (2H, m, $PhCHCH_2$), 3.78 (3H, s, OMe), 4.55 (1H, br m, OCH), 4.57 (1H, t, J 8Hz, $PhCHCH_2$), 6.7–6.8 (3H, m, $C_6H_3$), and 7.15–7.5 (9H, m, $C_6H_5$+benzimidazole $H_4$, $H_5$, $H_6$, $H_7$); m/z (ESI) 413 ($M^++1$, 100%), 186 (48). (Optical rotation at 0.151 g/100 ml of EtOH $[α]^{22}$=–1).

EXAMPLE 30 a) (±)-4-[1-(3-Cyclopentyloxy-4-methoxyphenyl)-2-(4-pyridyl)ethyl]aniline, Dihydrochloride, Hemihydrate A mixture of Intermediate 26 (3.80 g), ammonium formate (1.63 g), and 10% Pd/C (about 100 mg) in EtOH (50 ml) was heated to reflux for 2 h then stirred at room temperature for 2 days. The reaction mixture was then filtered through Celite® and the filtrate concentrated in vacuo. The residue was partitioned between aqueous NaOH (1M; 50 ml) and $CH_2Cl_2$ (50 ml). The organic layer was separated, dried ($Na_2SO_4$), and concentrated in vacuo. The residue was dissolved in $Et_2O$ (50 ml) and treated with ethanolic HCl (2.5M) then concentrated in vacuo. The residue was recrystallised (EtOH-$Et_2O$) to afford the title compound (3.4 g) as an off-white solid (Found: C, 63.97; H, 6.52; N, 5.77. $C_{25}H_{28}N_2O_2.2HCl.5H_2O$ requires C, 63.83; H, 6.64; N, 5.96%; $δ_H$ ($d_4$-MeOH) 1.5–1.9 (8H, br m, $CH_2)_4$), 3.7–3.85 (2H, m, $CHCH_2$ pyridine), 3.74 (3H, s, OMe), 4.56 (1H, t, J, 8.8Hz, $CHCH_2$ pyridine), 4.75 (1H, br m OCH), 6.8–6.85 (3H, m, $C_6H_3$), 7.35 (2H, ca. d, J 8.5Hz, ArH of $C_6H_4$), 7.55 (2H, d, J 8.5Hz, ArH of $C_6H_4$), 7.91 (2H, d, J 6.6Hz, pyridine $H_3$, $H_5$) and 8.65 (2H, d, J 6.6Hz, pyridine $H_2$, $H_6$)(N.B.N. $NH_2$ and 2HCl not observed); m/z (ESI) 389 ($M^++1$, 11%), 297 (26), 296 (100), and 228 (11).

The following compound was prepared in a manner similar to the compound of Example 28a.

b) (±)-2-[4-(1-(3-Cyclopentyloxy-4-methoxyphenyl)-2-(4-pyridyl)ethyl)phenyl]-4,4-dimethyl-1,3-oxazoline, Dihydrochloride Dihydrate From Intermediate 28b (0.27 g, 0.56 mmol), ammonium formate (0.70 g, 11.2 mmol) and 10% Pd/C (50mg). Chromatography ($SiO_2$; EtOAc) gave the title compound free base (180 mg) as a clear gum.

Dissolution of the title compound free base in $Et_2O$ and treatment with ethereal HCl (1M) furnished the title compound as a white solid. (Found: C, 61.98; H, 6.53; N, 4.61. $C_{30}H_{34}N_2O_3.2HCl$ $2H_2O$ requires C, 62.17; H. 6.96; N, 4.83%) δH ($d_4$-MeOH) 1.59 (6H, s $CMe_2$), 1.6–1.9 (8H, br m, $(CMe_2)_4$), 3.75 (3H, s, OMe), 3.7–3.9 (2H, m, $CH_2$-pyridine), 4.64 (1H, t, $CHCH_2$-pyridyl), 4.73 (1H, m, OCHD, 4.77 (2H, s, CH oxazolinyl), 6.8–6.9 (3H, m, $C_6H_3$), 7.68 (2H, d, J 8.4Hz, ArH meta to oxazoline), 7.90 (2H, d, J 6.6Hz, pyridine $H_3$, $H_5$), 8.01 (2H, d, J 8.4Hz, ArH ortho to oxazoline), and 8.65 (2H, d, J 6.5Hz, pyridine $H_2$, $H_2$); m/z (ESI) 471 ($M^++1$, 100%), 378 (67), and 245 (20).

EXAMPLE 31

(±)-Ethyl N-{4-[1-(3-Cyclopentyloxy-4-methoxyphenyl)-2-(4-pyridyl)ethyl]phenyl}carbamate Ethyl chloroformate (81 mg, 0.74 mmol, 1.3 eq) was added dropwise to a mixture of the compound of Example 30 (221 mg, 0.57 mmol) and triethylamine (75 mg, 0.74 mmol, 1.3 eq) in $CH_2Cl_2$ (20 ml). The reaction mixture was stirred overnight at RT, then concentrated in vacuo and the residue subjected to chromatography ($SiO_2$; hexane/EtOAc, 1:1) to afford the title compound (170mg) as a white solid; δH ($CDCl_3$) 1.29 (3H, t, J 7.1Hz, $OCH_2Me$), 1.5–2.0 (8H, br m, $(CH_2)_4$), 3.27 (2H, d, J 7.9Hz, $CHCH_2$ pyridine), 3.79

(3H, s, OMe), 4.10 (1H, t, J 7.9Hz, CHCH$_2$ pyridine), 4.20 (2H, q, J 7.1Hz, OCH$_2$Me), 4.64 (1H, br m OCH), 6.51 (1H, br s, NH), 6.6–6.8 (3H, m, C$_6$H$_3$), 6.92 (2H, d, J 5.9 Hz, pyridine H$_3$, H$_5$), 7.11 (2H, d, J 8.4 Hz, ArH of C$_6$H$_4$), 7.27 (2H, d, J 8.4 Hz, ArH of C$_6$H$_4$), and 8.38 (2H, d, J 5.9 Hz, pyridine H$_2$, H$_6$); m/z (ESI) 461 (M$^+$+1, 90%), 369 (25), and 368 (100).

EXAMPLE 32

(±)-N-{4-[1-(3-Cyclopentyloxy-4-methoxyphenyl)-2-(4-pyridyl)ethyl]phenyl}-N'-ethylurea A mixture of the compound of Example 30 (246 mg, 0.63 mmol) and ethyl isocyanate (68 mg, 0.95 mmol, 1.5eq) in CH$_2$Cl$_2$ (20 ml) was stirred at RT for 2 days. A further portion of ethyl isocyanate (68 mg, 0.95 mmol, 1.5 eq) was added and the mixture allowed to stir for 20 h. The reaction mixture was concentrated in vacuo and the residue subjected to chromatography (SiO$_2$; EtOAc) to afford the title compound (221 mg) as a white solid; δH (CDCl$_3$) 1.14 (3H, t, J 7.2Hz, OCH$_2$MMe), 1.5–2.0 (8H, br m, (CH$_2$)$_4$), 3.2–3.35 (4H, m, CHCH$_2$ pyridine+OCH$_2$Me), 3.79 (3H, s, OMe), 4.11 (1H, t, J 7.8Hz, CHCH$_2$ pyridine), 4.59 (1H, br m, NHCONH), 4.66 (1H, br m OCH), 6.16 (1H, br s, NHCONH), 6.65–6.7 (2H, m, ArH meta to OMe), 6.75 (1H, d, J 8.2Hz, ArH ortho to OMe), 6.93 (2H, br m, pyridine H$_3$, H$_5$), 7.12 (2H, d, J 8.6Hz, ArH of C$_6$H$_4$), 7.18 (2H, d, J 8.6Hz, ArH of C$_6$H$_4$), and 8.39 (2H, br s, pyridine H$_2$, H$_6$); m/z (ESI) 460 (M$^+$+1, 100%), and 117 (16).

EXAMPLE 33

(±)-N-[4-{1-(3-Cyclopentyloxy-4-methoxyphenyl)}-2-(4-pyridyl)ethyl]phenylacetamide Acetyl chloride (62 mg, 0.79 mmol, 1.3 eq) was added dropwise to the compound of Example 30 (235 mg, 0.60 mmol) in CH$_2$Cl$_2$ (20 ml) at 0° C. and the mixture allowed to stir at RT overnight. The reaction mixture was concentrated in vacuo and the residue subjected to chromatography (SiO$_2$; CH$_2$Cl$_2$/MeOH, 9:1) to afford the title compound (140 mg) as a white solid; δH (d$_4$-MeOH) 1.5–2.0 (8H, br m, (CH$_2$)$_4$), 2.09 (3H, s, COMe), 3.37 (2H, d, J 8.2Hz, CHCH$_2$ pyridine), 3.75 (3H, s, OMe), 4.23 (1H, t, J 8.2Hz, CHCH$_2$ pyridine), 4.69 (1H, br m OCH), 6.73 (1H, d, J 1.9Hz, ArH ortho to cyclopentyloxy), 6.77 (1H, dd, J 8.2, 1.9Hz, ArH para to OMe), 6.82 (1H, d, J 8.2Hz, ArH ortho to OMe), 7.15 (2H, d, J 5.7Hz, pyridine H$_3$, HO, 7.21 (2H, d, J 8.6Hz, ArH of C$_6$H$_4$), 7.42 (2H, d, J 8.6Hz, ArH of C$_6$H$_4$), and 8.27 (2H, br s, pyridine H$_2$, H$_6$) (N.B. NH not observed); m/z (ESI) 431 (M$^+$+1, 100%), and 338 (22).

EXAMPLE 34

(±)-4-[2-(3-Cyclopentyloxymethoxyphenyl)-2-(2-furyl)-2-hydroxyethyl]pyridine n-Butyllithium (1.6M solution in hexane; 16.9 ml, 27 mmol) was added to a stirred solution of furan (1.84 g, 1.96 ml, 27 mmol) in THF (25 ml) at –70° C. After 1 h at –70° C., a solution of Intermediate 1 (4.0 g, 18 mmol) in THF (10 ml) was added over 10 min. The reaction mixture was stirred at –70° C. for 0.75 h, warmed to RT over 0.75 h, then quenched with water (10 0 ml) and extracted with Et$_2$O (3×60 ml). The extract was washed with brine (100 ml), dried (MgSO$_4$), and concentrated in vacuo. The residual orange-yellow oil was subjected to chromatography (SiO$_2$; CH$_2$Cl$_2$/hexane, 3:1, then Et$_2$O/hexane, 1:1) to give (3-cyclopentyloxy-4-methoxyphenyl)(2-furyl)methanol (3.2 g, 61%) as a colorless unstable oil; ν$_{max}$ (neat) 3500 cm$^{-1}$.

The alcohol (3.2 g) was stirred with manganese (IV) oxide (10 g) in CH$_2$Cl$_2$ (100 ml) at RT for 3 h. The mixture was filtered through Celite® and the filtrate concentrated in vacuo. The residual dark oil was subjected to chromatography (SiO$_2$) to give (3-cyclopentyloxy-4-methoxyphenyl)-(2-furyl)ketone (1.9 g); ν$_{max}$ (neat) 1620cm$^{-1}$. n-Butyllithium (1.6M solution in hexanes; 4.2 ml, 6.64 mmol) was added to a solution of a 4-methylpyridine (0.62 g, 0.65 ml, 6.64 mmol) in THF (25 ml) at –70° C. After 0.5 h, a solution of the crude ketone (1.9 g, ca 6.6 mmol) in THF (5 ml) was added, stirred for 1 h at –70° C., then at RT fix 0.25 h. The reaction mixture was quenched with water (50 ml) and extracted with EtOAc (3×50 ml). The extract was dried (MgSO$_4$), concentrated in vacuo, and the residual red oil subjected to chromatography (SiO$_2$; EtOAc/hexane, 3:2) to afford the title compound (1.23 g, 49%) as a pale yellow oil; δH (CDCl$_3$) 1.5–1.9 (8H, br m, (CH$_2$)$_4$), 2.84 (1H, br s, OH), 3.30 (1H, d, J 13.2 Hz, CH$_A$H$_B$ pyridine), 3,59 (1H, d, J 13.2 Hz, CH$_A$H$_B$ pyridine), 3.82 (3H, s, OMe), 4.65 (1H, br m OCH), 6.24 (1H-[, dd, J 3.3, 0.7Hz, furan H$_3$), 6.35 (1H, dd, J 3.3, 1.8Hz, furan H$_4$), 6.75–6.85 (3H, m, C$_6$H$_3$), 6.85 (2H, dd, J 4.5, 1.6Hz, pyridine H$_3$,H$_5$), 7.43 (1H, dd, J 1.8, 0.7Hz, furan H$_5$), and 8.33 (2H, dd, J 4.5, 1.6Hz, pyridine H$_2$, H$_6$); m/z (ESI) 402 (M$^+$+23, 20%), 380 (M$^+$+1, 35), 287 (100), 95 (28), and 94 (97).

EXAMPLE 35

(R)-4-[2-(3-Cyclopentyloxy-4-methoxyphenyl)-2-phenylethyl]pyridine hydrogen sulphate salt The compound of Example 16(i) (14.5 g, 39 mmol) was dissolved in warm ethanol (150 ml) and the clear solution was cooled to room temperature. Concentrated sulphuric acid (3.3 ml, 60 mmol) was added with swirling over one minute, followed by the addition of a few seed crystals. The solution was allowed to stand at room temperature for 1.5 hours during which time needle-like crystals steadily developed. The solution was then left at 40° C. overnight to maximize yield. The resulting product was warmed to room temperature and the crystalline product was collected by suction filtration with t-butylmethyl ether washing. Once sufficiently dry, the product was transferred to a vacuum oven and heated in vacuo to dryness overnight (65° C., ~0.05 mbar) to afford the title salt as a white crystalline powder (16.2 g); m.p. 144°–140° C.; Found C, 63.72; H, 6.15; N, 2.97. C$_{25}$H$_{29}$NO$_6$S requires C, 63.68; H, 6.20; N, 2.97%.

The title salt (3.3 g) was recrystallized (with slow cooling to room temperature, then leaving at room temperature for 2 hours) from absolute ethanol (~40 ml). The resulting white needles we, re filtered, washed with diethyl ether and dried at 75° C. at 0.05 mbar overnight.

FORMULATION EXAMPLES

The compounds of the invention may be formulated for pharmaceutical use in a number of forms using any suitable excipients. Thus, for example, for oral use, the compounds of the invention, such as the compounds of the Examples, may be formulated as a solid dosage form, by mixing an appropriate weight of compound, for example, 50 mg, with maize starch (50–99% w/w), anhydrous colloidal silica (0–10% w/w) and inorganic acid (up to 1% w/w), to fill capsules of an appropriate size, for example, white opaque hard gelatine capsules size 3. If desired, the same mixture may be compressed into tablets.

FORMULATION EXAMPLE 1

This example shows the formulation of granules containing (R)-4-[2-(3-cyclopentyloxy-4-methoxyphenyl)-2-phenylethyl]pyridine hydrogen sulphate salt from Example 34 (referred to in this example as "Active Ingredient"):

|  | Unit Quantity | Batch Quantity |
|---|---|---|
| Active Ingredient | 0.1263 mg | 0.2210 g |
| Maize Starch BP | 112.7 mg | 197.2 g |
| Purified Water | — | 110 ml |
| Colloidal silica (Aerosil 200) | 1.71 mg | 2.993 g |

The granules were used to fill capsules, or were compressed into tablets.

BIOLOGICAL ACTIVITY

The activity and selectivity of compounds according to the invention was demonstrated in the following tests. In these tests, the term "FMLP" refers to the peptide N-formyl-met-leu-phe.

1. Isolated Enzyme

The potency and selectivity of the compounds of the invention were determined using a battery of distinct PDE isoenzymes as follows:

i. PDE I, rabbit heart ii. PDE II, rabbit heart iii. PDE III, rabbit heart, Jurkat cells iv. PDE IV, HL60 cells, rabbit brain, rabbit kidney and human recombinant PDE IV v. PDE V, HL60 cells, rabbit lung, guinea pig lung The enzymes were purified to kinetic homogeneity using standard chromatographic techniques.

Phosphodiesterase activity was assayed as follows. The reaction was conducted in 150 µl of standard mixture containing (final concentrations): 50 mM 2-[[tris(hydroxymethyl)methyl]amino]-1-ethanesulphonic acid (TES)-NaOH buffer (pH 7.5), 10 mM $MgCl_2$, 0.1 µM [$^3$H]-cAMP and vehicle or various concentrations of the test compounds. The reaction was initiated by addition of enzyme and conducted at 30° C. for between 5 to 30 mins. The reaction was terminated by addition of 50 µl 2% trifluoroacetic acid containing [$^{14}$C]-5'AMP for determining recovery of the product. An aliquot of the sample was then applied to a column of neutral alumina and the [$^3$H]-cAMP eluted with 10 ml 0.1 TES-NaOH buffer (pH 8). The [$^3$H]-5'-AMP product was eluted with 2 ml 2M NaOH into a scintillation vial containing 10 ml of scintillation cocktail. Recovery of [$^3$H]-5'AMP was determined using the [$^{14}$C]-5'AMP and all assays were conducted in the linear range of the reaction.

A gene encoding human PDE IV has been cloned from human monocytes (Livi, et al., 1990, *Molecular and Cellular Biology*, 10, 2678). Using similar procedures, human PDE IV genes have been cloned from a number of sources, including eosinophils, neutrophils, lymphocytes, monocytes, brain and neuronal tissues. These genes have been transfected into yeast using an inducible vector and various recombinant proteins have been expressed which have the biochemical characteristics of PDE IV (Beavo and Reifsnyder, 1990, *TIPS*, 11, 150). These recombinant enzymes, particularly the human eosinophil recombinant PDE IV, have been used as the basis of a screen for potent, selective PDE IV inhibitors.

Compounds according to the invention, such as the compounds of the Examples herein, cause a concentration-dependent inhibition of recombinant PDE·IV at 0.1–1000 nM with little or no activity against PDE I, II, III or V at concentrations up to 100 µM.

2. The Elevation of cAMP In Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 rain and then stimulated with FMLP. Guinea pig eosinophils were harvested by peritoneal lavage of animals previously treated with intraperitoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the Examples induced a concentration-dependent elevation of cAMP in neutrophils and/or eosinophils at concentrations of 0.1 nM to 1 µM. The compound of Example 35 [(R)-4-[2-(3-Cyclopentyloxy-4-methoxyphenyl)-2-phenylethyl]pyridine hydrogen sulphate salt] induced a concentration-dependent elevation of cAMP in neutrophils and/or eosinophils at concentrations of 0.1 nM.

3. Suppression of Leukocyte Function

Compounds of the invention were investigated for their effects on superoxide generation and chemotaxis of human neutrophils. Neutrophils were separated from peripheral blood, incubated with dihydrocytochalasin B for superoxide generation only and test compound prior to stimulation with FMLP. The most potent compounds of the Examples caused a concentration-dependent inhibition of superoxide generation and chemotaxis at concentrations of 0.1 nM to 1 µM. The compound according to Example 35 caused a concentration-dependent inhibition of superoxide generation, chemotaxis and adhesion at a concentration of 0.1 nM.

Lipopolysaccharide (LPS)-induced synthesis of tumor necrosis factor (TNF) by human peripheral blood monocytes (PBM) is inhibited by compounds of the Examples at concentrations of 0.01 nM to 10 µM.

4. Relaxation of Constricted Airway Smooth Muscle in vitro

The effects of compounds of the invention on guinea-pig isolated tracheal smooth muscle were investigated. Isolated tracheal rings were suspended in organ baths and immersed in oxygenated Krebs' solution. The smooth muscle was contracted with submaximal concentrations of histamine or carbachol prior to the addition of increasing concentrations of test compound to the organ baths. The most potent compounds of the Examples caused a concentration-dependent reversal of both histamine and carbachol-induced contractions at concentrations of 1 nM to 100 µM. The compounds were generally more potent in reversing histamine-induced tone than carbachol-induced tone.

5. Effects on Cardiac Muscle in vitro

Compounds of the invention have been tested for their effects on isolated cardiac muscle. Right atrial and papillary muscles were dissected out from the hearts of guinea pigs and suspended in organ baths for measuring the rate (chronotropic) of spontaneously beating atria and force (inotropic) of the electrically stimulated papillary muscle. In these preparations, selective PDE IV inhibitors, such as rolipram, do not have any direct effects, whereas selective PDE III inhibitors, such as milrinone, have positive chronotropic and inotropic effects. The non-specific PDE inhibitor theophylline, which is used in asthma as a bronchodilator, also causes significant cardiovascular changes, such as tachycardia. Selective PDE IV inhibitors have advantage over theophylline, therefore, through reduced cardiovascular side effects. The most potent and selective compounds of the Examples had no direct effects on the atrial and papillary muscles in vitro at concentrations up to 10 μM, but in combination with PDE III inhibitors, these inhibitors showed an enhancement of chronotropic and inotropic activity, typical of selective type IV inhibitors.

6. Anti-inflammatory Activity in vivo

Interleukin-5 (IL-5)-induced pleural eosinophilia in the rat (Lisle, et al. 1993, *Br. J. Pharmacol.* 108 230p) is inhibited by compounds of the Examples given orally at doses of 0.0001 to 10.0 mg/kg. The most potent compounds cause a dose-dependent reduction in migrating eosinophils with $ED_{50}$s of 0.003 to 0.03 mg/kg p.o.

Compounds of the invention also reduce the inflammatory responses induced in rats by platelet activating factor (PAF).

7. Anti-allergic Activity in vivo

Compounds of the invention have been tested for effects on an lgE-mediated allergic pulmonary inflammation induced by inhalation of antigen by sensitised guinea pigs. Guinea pigs were initially sensitised to ovalbumin under mild cyclophosphamide-induced immunosuppression, by intraperitoneal injection of antigen in combinations with aluminium hydroxide and pertussis vaccine. Booster doses of antigen were given two and four weeks later and at six weeks, animals were challenged with aerosolised ovalbumin whilst under cover of an intraperitoneally administered anti-histamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examaples (0.001–10 mg/kg i.p. or p.o.), up to three times during the 48 h following antigen challenge, led to a significant reduction in the eosinophilia and the accumulation of other inflammatory leukocytes. There was also less inflammatory damage in the lungs of animals treated with compounds of the Examples.

8. Effects on Pulmonary Dynamics

Compounds of the invention have been tested for their effects on ozone-induced hyperreactivity of the airways of guinea pigs. Following the inhalation of ozone, guinea pigs become very much more sensitive to the bronchoconstrictor effects of inhaled histamine than naive animals. (Yeadon et al. 1992, Pulmonary Pharm., 5, 39). There is a pronounced shift to the left (10–30 fold) of the dose response curve to histamine and a highly significant increase in the maximum increase in pulmonary resistance. Compounds of the Examples administered 1 h prior to ozone by the intraperitoneal or oral (0.001–10 mg/kg) route caused a dose-dependent inhibition of ozone-induced hyperreactivity.

Compounds of the invention are free from adverse effects following repeated overdosage to rats or dogs. For example, over administration of 125 mg/kg/day of active compounds of the Examples to rats for 30 days is not associated with adverse toxicity.

The disclosures of each patent, patent application and publication cited or described in this document are hereby incorporated by reference, in their entirety.

Various modifications of the invention, in addition to those described herein, will be apparent to those skilled in the art from the foregoing description. Such modifications are also intended to fall within the scope of the appended claims.

We claim:

1. A compound of formula (1)

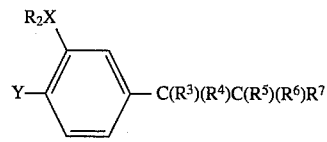

wherein

Y is halogen or —$OR^1$, where $R^1$ is substituted or unsubstituted $C_{1-6}$alkyl, said $R^1$ substituent being halogen;

X is —O—, —S— or —$N(R^8)$—, where $R^8$ is hydrogen or $C_{1-6}$alkyl;

$R^2$ is substituted or unsubstituted $C_{3-8}$cycloalkyl or substituted or unsubstituted $C_{3-8}$cycloalkenyl, said $R^2$ substituents being halogen, $C_{1-6}$alkyl, hydroxyl or $C_{1-6}$alkoxy;

$R^3$ is hydrogen, halogen or —$OR^9$, where $R^9$ is hydrogen or substituted or unsubstituted $C_{1-6}$alkyl, substituted or unsubstituted $C_{2-6}$alkenyl, substituted or unsubstituted $C_{1-3}$alkoxy$C_{1-3}$alkyl, substituted or unsubstituted $C_{1-6}$alkanoyl, HC(=O)—, —$CONR^{11}R^{12}$ or —$CSNR^{11}R^{12}$; where each of $R^{11}$ and $R^{12}$ is hydrogen or substituted or unsubstituted $C_{1-6}$alkyl; said $R^3$ substituents being halogen, $C_{1-6}$alkyl, hydroxyl or $C_{1-6}$alkoxy;

each of $R^4$ and $R^5$ is independently —$(CH_2)_n$Ar, where n is an integer of 0 to 3, and Ar is monocyclic or bicyclic, substituted or unsubstituted $C_{6-12}$aryl, or monocyclic or bicyclic, substituted or unsubstituted heteroaryl selected from the group consisting of pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl, said $R^4$ and $R^5$ substituents being $R^{13}$ or —$Alk^1(R^{13})_m$;

each of $R^6$ and $R^7$ is independently hydrogen or substituted or unsubstituted $C_{1-6}$alkyl, said $R^6$ and $R^7$ substituents being halogen, hydroxyl or $C_{1-6}$alkoxy;

$R^{13}$ is halogen, —$NH_2$, substituted —$NH_2$, nitro, cyano, —OH, —$OAlk^1(R^{13a})_m$, cycloalkoxy, HC(=O)—, —$CO_2H$, esterified —$CO_2H$, —SH, —$SAlk^1(R^{13a})_m$, —C(=O)$Alk^1$, —$SO_3H$, —$SO_2Alk^1$, —$SO_2NH_2$, —$SO_2NHAlk^1$, —$SO_2N(Alk^1)_2$, —$CONH_2$, —CONHAlk$^1$, —CON(Alk$^1$)$_2$, —$NHSO_2H$, —$NHSO_2Alk^1$, —N(SO$_2$Alk$^1$)$_2$, —$NHSO_2NH_2$, —$NHSO_2NHAlk^1$, —$NHSO_2N(Alk^1)_2$, —NHC(=O)Alk$^1$ or —NHC(=O)OAlk$^1$;

$R^{13a}$ is halogen, —$NH_2$, nitro, cyano, —OH, cycloalkoxy, HC(=O)—, —$CO_2H$, esterified —$CO_2H$, —SH, —C(=O)Alk$^1$, —$SO_3H$, —$SO_2Alk^1$, —$SO_2NH_2$, —$SO_2NHAlk^1$, —$SO_2N(Alk^1)_2$, —$CONH_2$, —CONHAlk$^1$, —CON(Alk$^1$)$_2$, —$NHSO_2H$, —$NHSO_2Alk^1$, —N(SO$_2$Alk$^1$)$_2$, —NHSO$_2$NH$_2$, —NHSO$_2$NHAlk$^1$, —NHSO$_2$N(Alk$^1$)$_2$, —NHC(—O)Alk$^1$ or —NHC(=O)OAlk$^1$;

Alk$^1$ is straight or branched C$_{1-6}$alkylene, C$_{2-6}$alkenylene or C$_{2-6}$alkynylene, optionally interrupted with up to three —O—, —S—, —N(R$^8$)— or —S(O)$_p$— groups or, when Alk$^1$ is a substituent, Alk$^1$ is straight or branched C$_{1-6}$alkyl, C$_{2-6}$alkenyl or C$_{2-6}$alkynyl, optionally interrupted with up to three —O—, —S—, —N(R$^8$)— or —S(O)$_p$— groups;

m is an integer of 0 to 3; and p is 1 or 2;

or the salt, solvate, hydrate or N-oxide thereof.

2. A compound according to claim 1 wherein X is —O—.

3. A compound according to claim 1 or claim 2, wherein Y is methoxy.

4. A compound according to claim 1 wherein R$^2$ is substituted or unsubstituted cyclopentyl.

5. A compound according to claim 1 wherein R$^3$ is hydrogen.

6. A compound according to claim 1 wherein each of R$^6$ and R$^7$ is independently hydrogen or methyl.

7. A compound according to claim 6 wherein each of R$^6$ and R$^7$ is hydrogen.

8. A compound according to claim 1 wherein Y is methoxy, X is —O—, R$^2$ is substituted or unsubstituted cyclopentyl, each of R$^3$, R$^6$ and R$^7$ is hydrogen, and each of R$^4$ and R$^5$ is independently substituted or unsubstituted Ar.

9. A compound according to claim 8 wherein each of R$^4$ and R$^5$ is independently substituted or unsubstituted monocyclic aryl or substituted or unsubstituted monocyclic heteroaryl.

10. A compound according to claim 9 wherein said monocyclic aryl is substituted or unsubstituted phenyl and said monocyclic heteroaryl is substituted or unsubstituted furyl, thienyl, pyridyl, pyridazinyl, pyrimidinyl or pyrazinyl.

11. A compound according to claim 10 wherein said heteroaryl is substituted or unsubstituted pyridyl.

12. A compound selected from the group consisting of:
(±)-4-[2-(3-cyclopentyloxy-4-methoxyphenyl)-2-(2-furyl)ethyl]pyridine;
(±)-4-[2-(3-cyclopentyloxy-4-methoxyphenyl)-2-(2-thienyl)ethyl]pyridine;
(±)-4-[2-(3-cyclopentyloxy-4-methoxyphenyl)-2-phenylethyl]-3-methylimidazole;
(±)-4-[2-(3-cyclopentyloxy-4-methoxyphenyl)-2-phenylethyl]pyridine;
(±)-4-[1-(3-cyclopentyloxy-4-methoxyphenyl)-2-(4-pyridyl)ethyl]pyridine;
(±)-4-[2-(3-cyclopentyloxy-4-methoxyphenyl)-2-(4fluorophenyl)ethyl]pyridine;
(±)-4-[2-(3-cyclopentyloxy-4-methoxyphenyl)-2-(4trifluoromethylphenyl)ethyl]-pyridine;
(±)-4-[2-(3-cyclopentyloxy-4-methoxyphenyl)-2-(2-methoxyphenylethyl)]pyridine;
(±)-4-[2-(3-cyclopentyloxy-4-methoxyphenyl)-2-(4-methoxyphenyl)ethyl]pyridine;
(±)-4-[2-(3-cyclopentyloxy-4-methoxyphenyl)-2-(4-methylphenyl)ethyl]pyridine;
(±)-4-[2-(3-cyclopentyloxy-4-methoxyphenyl)-2-(3-methylphenyl)ethyl]pyridine;
(±)-4-[2-(3-cyclopentyloxy-4-methoxyphenyl)-2-(3-cyclopentyloxy-4-methoxyphenyl)ethyl]pyridine;
(±)-4-[2-(3-cyclopentyloxy-4-methoxyphenyl)-2-phenylethyl]-3,5-dichloropyridine;
(±)-2-[2-(3-cyclopentyloxy-4-methoxyphenyl)-2-phenylethyl]pyridine;
(±)-4-[1-(3-cyclopentyloxy-4-methoxyphenyl)-2-(4-pyridyl)ethyl]aniline;
(±)-4-[1-(3-cyclopentyloxy-4-methoxyphenyl)-2-(4-pyridyl)ethyl]benzoic acid;
(±) Ethyl N-[4-[1-(3-cyclopentyloxy-4-methoxyphenyl)-2-(4-pyridyl)ethyl]phenyl]carbamate;
(±)-N-(4-[1-(3-cyclopentyloxy-4-methoxyphenyl)-2-(4-pyridyl)ethyl]phenyl)-N'-ethylurea;
(±)-N-(4-[1-(3-cyclopentyloxy-4-methoxyphenyl)-2-(4-pyridyl)ethyl)phenyl]acetamide;
(±)-3-[2-(3-cyclopentyloxy-4-methoxyphenyl)-2-phenylethyl]pyridine;
(±)-4-[2-(3-cyclopentyloxy-4-methoxyphenyl)-2-phenylethyl]pyrimidine;
(±) -4-[2-(3-cyclopentyloxy-4-methoxyphenyl)-2-(4-hydroxymethylphenyl)ethyl]pyridine;
(±)-4-[1-(3-cyclopentyloxy-4-methoxyphenyl)-2-(4-pyridyl)ethyl]benzamide;
(±) Ethyl-4-[1-(3-Cyclopentyloxy-4-methoxyphenyl)-2-(4-phenylethyl]benzoate; and
(±) N-(4-[1-(3-cyclopentyloxy-4-methoxyphenyl)-2-(4-pyridyl)ethyl]phenyl)methanesulphonamide; or
the resolved enantiomers thereof, and the salts, solvates, hydrate and N-oxides thereof.

13. A compound according to claim 12 which is (±)-4-[2-(3-cyclopentyloxy-4-methoxyphenyl)-2-phenylethyl]pyridine; and the salt, solvate, hydrate and N-oxide thereof.

14. A compound according to claim 13 which is (±)-4-[2-(3-cyclopentyloxy-4-methoxyphenyl)-2-phenylethyl]pyridine hydrogen sulphate salt.

15. A compound according to claim 12 which is (R)-4-[2-(3-cyclopentyloxy-4-methoxyphenyl)-2-phenylethyl]pyridine; and the salt, solvate, hydrate and N-oxide thereof.

16. A compound according to claim 15 which is (R)-4-[2-(3-cyclopentyloxy-4-methoxyphenyl)-2-phenylethyl]pyridine hydrogen sulphate salt.

17. A compound according to claim 12 which is (+)-4-[1-(3-cyclopentyloxy-4-methoxyphenyl)-2-(4-pyridyl)ethyl]pyridine.

18. A compound according to claim 12 which is (−)-4-[1-(3-cyclopentyloxy-4-methoxyphenyl)-2-(4-pyridyl)ethyl]pyridine.

19. A compound according to claim 13 which is (±)-4-[2-(3-cyclopentyloxy-4-methoxyphenyl)-2-phenylethyl]pyridine.

20. A compound according to claim 12 which is (+)-4-[2-(3-cyclopentyloxy-4-methoxyphenyl)-2-phenylethyl]pyridine.

21. A compound according to claim 12 which is (−)-4-[2-(3-cyclopentyloxy-4-methoxyphenyl)-2-phenylethyl]pyridine.

22. A pharmaceutical composition comprising a compound of formula (1)

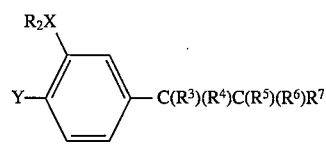

wherein

Y is halogen or —OR$^1$, where R$^1$ is substituted or unsubstituted C$_{1-6}$alkyl, said R$^1$ substituent being halogen;

X is —O—, —S— or —N(R$^8$)—, where R$^8$ is hydrogen or C$_{1-6}$alkyl;

R$^2$ is substituted or unsubstituted C$_{3-8}$cycloalkyl or substituted or unsubstituted C$_{3-8}$cycloalkenyl, said R$^2$ substituents being halogen, $C_{1-6}$alkyl, hydroxyl or $C_{1-6}$alkoxy;

$R^3$ is hydrogen, halogen or —$OR^9$, where $R^9$ is hydrogen or substituted or unsubstituted $C_{1-6}$alkyl, substituted or unsubstituted $C_{2-6}$alkenyl, substituted or unsubstituted $C_{1-3}$alkoxy$C_{1-3}$alkyl, substituted or unsubstituted $C_{1-6}$alkanoyl, HC(=O)—, —$CONR^{11}R^{12}$ or —$CSNR^{11}R^{12}$ where each of $R^{11}$ and $R^{12}$ is hydrogen or substituted or unsubstituted $C_{1-6}$alkyl; said $R^3$ substituents being halogen, $C_{1-6}$alkyl, hydroxyl or $C_{1-6}$alkoxy;

each of $R^4$ and $R^5$ is independently —$(CH_2)_n$Ar, where n is an integer of 0 to 3, and Ar is monocyclic or bicyclic, substituted or unsubstituted $C_{6-12}$aryl, or monocyclic or bicyclic, substituted or unsubstituted heteroaryl selected from the group consisting of pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl, said $R^4$ and $R^5$ substituents being $R^{13}$ or —$Alk^1(R^{13})_m$;

each of $R^6$ and $R^7$ is independently hydrogen or substituted or unsubstituted $C_{1-6}$alkyl, said $R^6$ and $R^7$ substituents being halogen, hydroxyl or $C_{1-6}$alkyl;

$R^{13}$ is halogen, —$NH_2$, substituted —$NH_2$, nitro, cyano, —OH, —$OAlk^1(R^{13a})_m$, cycloalkoxy, HC(=O)—, —$CO_2H$, esterified —$CO_2H$, —SH, —$SAlk^1(R^{13a})_m$, —C(=O)$Alk^1$, —$SO_3H$, —$SO_2Alk^1$, —$SO_2NH_2$, —$SO_2NHAlk^1$, —$SO_2N(Alk^1)_2$, —$CONH_2$, —$CONHAlk^1$, —$CON(Alk^1)_2$, —$NHSO_2H$, —$NHSO_2Alk^1$, —$N(SO_2Alk^1)_2$, —$NHSO_2NH_2$, —$NHSO_2NHAlk^1$, —$NHSO_2N(Alk^1)_2$, —NHC(=O)$Alk^1$ or —NHC(=O)$OAlk^1$;

$R^{13a}$ is halogen, —$NH_2$, nitro, cyano, —OH, cycloalkoxy, HC(=O)—, —$CO_2H$, esterified —$CO_2H$, —SH, —C(=O)$Alk^1$, —$SO_3H$, —$SO_2Alk^1$, —$SO_2NH_2$, —$SO_2NHAlk^1$, —$SO_2N(Alk^1)_2$, —$CONH_2$, —$CONHAlk^1$, —$CON(Alk^1)_2$, —$NHSO_2H$, —$NHSO_2Alk^1$, —$N(SO_2Alk^1)_2$, —$NHSO_2NH_2$, —$NHSO_2NHAlk^1$, —$NHSO_2N(Alk^1)_2$, —NHC(=O)$Alk^1$ or —NHC(=O)$OAlk^1$;

$Alk^1$ is straight or branched $C_{1-6}$alkylene, $C_{2-6}$alkenylene or $C_{2-6}$alkynylene, optionally interrupted with up to three —O—, —S—, —$N(R^8)$— or —$S(O)_p$— groups or, when $Alk^1$ is a substituent, $Alk^1$ is straight or branched $C_{1-6}$alkyl, $C_{2-6}$alkenyl or $C_{2-6}$alkynyl, optionally interrupted with up to three —O—, —S—, —$N(R^8)$— or —$S(O)_p$— groups;

m is an integer of 0 to 3; and p is 1 or 2;

or the salt, solvate, hydrate or N-oxide thereof; together with one or more pharmaceutically acceptable carriers, excipients or diluents.

23. A pharmaceutical composition comprising, in combination with one or more pharmaceutically acceptable carriers, excipients or diluents, (±)-4-[2-(3-cyclopentyloxy-4-methoxyphenyl)-2-phenylethyl]pyridine or a resolved enantiomer thereof, and the salt, solvate, hydrate and N-oxide thereof.

24. A composition according to claim 23 which comprises (+)-4-[2-(3-cyclopentyloxy-4-methoxyphenyl)-2-phenylethyl]pyridine hydrogen sulphate salt.

25. A composition according to claim 23 which comprises (R)-4-[2-(3-cyclopentyloxy-4-methoxyphenyl)-2-phenylethyl]pyridine; and the salt, solvate, hydrate and N-oxide thereof.

26. A composition according to claim 25 which comprises (R)-4-[2-(3-cyclopentyloxy-4-methoxyphenyl)-2-phenylethyl]pyridine hydrogen sulphate salt.

27. A method of preventing or treating an inflammatory disease in a patient comprising administering to said patient, in combination with a pharmaceutically acceptable carrier, a selective inhibitor of a phosphodiesterase (PDE) IV isoenzyme in an amount sufficient to elevate intracellular levels of adenosine 3',5'-cyclic monophosphate (cAMP), said inhibitor being selected from a compound of the formula:

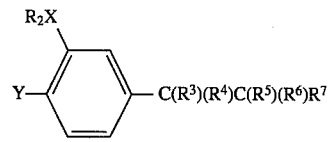

wherein

Y is halogen or —$OR^1$, where $R^1$ is substituted or unsubstituted $C_{1-6}$alkyl, said $R^1$ substituent being halogen;

X is —O—, —S— or —$N(R^8)$—, where $R^8$ is hydrogen or $C_{1-6}$alkyl;

$R^2$ is substituted or unsubstituted $C_{3-8}$cycloalkyl or substituted or unsubstituted $C_{3-8}$cycloalkenyl, said $R^2$ substituents being halogen, $C_{1-6}$alkyl, hydroxyl or $C_{1-6}$alkoxy;

$R^3$ is hydrogen, halogen or —$OR^9$, where $R^9$ is hydrogen or substituted or unsubstituted $C_{1-6}$alkyl, substituted or unsubstituted $C_{2-6}$alkenyl, substituted or unsubstituted $C_{1-3}$alkoxy$C_{1-3}$alkyl, substituted or unsubstituted $C_{1-6}$alkanoyl, HC(=O)—, —$CONR^{11}R^{12}$ or —$CSNR^{11}R^{12}$; where each of $R^{11}$ and $R^{12}$ is hydrogen or substituted or unsubstituted $C_{1-6}$alkyl; said $R^3$ substituents being halogen, $C_{1-6}$alkyl, hydroxyl or $C_{1-6}$alkoxy;

each of $R^4$ and $R^5$ is independently —$(CH_2)_n$Ar, where n is an integer of 0 to 3, and Ar is monocyclic or bicyclic, substituted or unsubstituted $C_{6-12}$aryl, or monocyclic or bicyclic, substituted or unsubstituted heteroaryl selected from the group consisting of pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl, said $R^4$ and $R^5$ substituents being $R^{13}$ or —$Alk^1(R^{13})_m$;

each of $R^6$ and $R^7$ is independently hydrogen or substituted or unsubstituted $C_{1-6}$alkyl, said $R^6$ and $R^7$ substituents being halogen, hydroxyl or $C_{1-6}$ alkoxy;

$R^{13}$ is halogen, —$NH_2$, substituted —$NH_2$, nitro, cyano, —OH, —$OAlk^1(R^{13a})_m$, cycloalkoxy, HC(=O)—, —$CO_2H$, esterified —$CO_2H$, —SH, —$SAlk^1(R^{13a})_m$, —$C(=O)Alk^1$, —$SO_3H$, —$SO_2Alk^1$, —$SO_2NH_2$, —$SO_2NHAlk^1$, —$SO_2N(Alk^1)_2$, —$CONH_2$, —$CONHAlk^1$, —$CON(Alk^1)_2$, —$NHSO_2H$, —$NHSO_2Alk^1$, —$N(SO_2Alk^1)_2$, —$NHSO_2NH_2$, —$NHSO_2NHAlk^1$, —$NHSO_2N(Alk^1)_2$, —$NHC(=O)Alk^1$ or —$NHC(=O)OAlk^1$;

$R^{13a}$ is halogen, —$NH_2$, nitro, cyano, —OH, cycloalkoxy, HC(=O)—, —$CO_2H$, esterified —$CO_2H$, —SH, —$C(=O)Alk^1$, —$SO_3H$, —$SO_2Alk^1$, —$SO_2NH_2$, —$SO_2NHAlk^1$, —$SO_2N(Alk^1)_2$, —$CONH_2$, —$CONHAlk^1$, —$CON(Alk^1)_2$, —$NHSO_2H$, —$NHSO_2Alk^1$, —$N(SO_2Alk^1)_2$, —$NHSO_2NH_2$, —$NHSO_2NHAlk^1$, —$NHSO_2N(Alk^1)_2$, —$NHC(=O)Alk^1$ or —$NHC(=O)OAlk^1$;

$Alk^1$ is straight or branched $C_{1-6}$alkylene, $C_{2-6}$alkenylene or $C_{2-6}$alkynylene, optionally interrupted with up to three —O—, —S—, —$N(R^8)$— or —$S(O)_p$— groups or, when $Alk^1$ is a substituent, $Alk^1$ is straight or branched $C_{1-6}$alkyl, $C_{2-6}$alkenyl or $C_{2-6}$alkynyl, optionally interrupted with up to three —O—, —S—, —$N(R^8)$— or —$S(O)_p$— groups;

m is an integer of 0 to 3; and p is 1 or 2;

or the salt, solvate, hydrate or N-oxide thereof; together with one or more pharmaceutically acceptable carriers, excipients or diluents.

28. A method according to claim 1 wherein said inflammatory disease asthma.

29. A method according to claim 1 wherein said inflammatory disease is selected from the group consisting of inflammatory airway disease, chronic bronchitis, eosinophilic granuloma, inflammatory arthritis, atopic dermatitis, urticaria, allergic rhinitis, adult respiratory distress syndrome, and allergic conjunctivitis.

* * * * *

UNITED STATES PATENT AND TRADEMARK OFFICE
CERTIFICATE OF CORRECTION

PATENT NO. : 5,622,977
DATED : April 22, 1997
INVENTOR(S) : Warrellow et al.

Page 1 of 2

It is certified that error appears in the above-indentified patent and that said Letters Patent is hereby corrected as shown below:

Column 5, line 57, delete "At" and insert therefor --AR--.
Column 21, line 67, delete "pate" and insert therefor --pale--.
Column 24, line 30, delete "(3lt,s,OMe)" and insert therefor --(3H,s,OMe)--.
Column 25, line 39, delete "CH$_2$)$_4$)$_4$)" and insert therefor --CH$_2$)$_4$)--.
Column 26, line 48, delete "5H" and insert therefor --δH--.
Column 27, line 5, delete "(ESI)$_{429}$" and insert therefor --(ESI)429--.
Column 27, line 60, delete "At)" and insert therefor --Ar)--.
Column 27, line 60 delete "C$_2$H" to --(2H--.
Column 28, line 7, delete "1.:3)" and insert therefor --1:3)--.
Column 33, line 59, delete "rifle" and insert therefor --title--.
Column 38, line 19, delete "7.2-7.3" and insert therefor --7.1-7.3--.
Column 40, line 63, delete "off-whim" and insert therefor --off white--.
Column 42, line 60, delete "front" and insert therefor --from--.
Column 44, line 47, delete "123°-123°" and insert therefor --123°-125°--.
Column 45, line 33, delete "soution" and insert therefor --solution--.
Column 49, line 66, delete "OMMe" and insert therefor --OM$_e$--.
Column 51, line 38, delete "$^1$H" and insert therefor --δH--.
Column 51, line 45, after the word "and" insert --60(81)--.
Column 52, line 29, delete "(N.B.N.NH$_2$" and insert therefor --N.B. NH$_2$--.
Column 52, line 48, delete "OCHD" and insert therefor --OCH--.
Column 53, line 64, delete "(10 0 ml)" and insert therefor --(100 ml)--.
Column 54, line 55, delete "we, re" and insert therefor --were--.

UNITED STATES PATENT AND TRADEMARK OFFICE
CERTIFICATE OF CORRECTION

PATENT NO. : 5,622,977

DATED : April 22, 1997

INVENTOR(S) : Warrellow et al.

It is certified that error appears in the above-identified patent and that said Letters Patent is hereby corrected as shown below:

Column 57, line 39, delete "Examaples" and insert therefor --Examples--.

Signed and Sealed this

Sixteenth Day of December, 1997

Attest:

BRUCE LEHMAN

Attesting Officer

Commissioner of Patents and Trademarks